(12) United States Patent
Kim et al.

(10) Patent No.: US 9,761,813 B2
(45) Date of Patent: Sep. 12, 2017

(54) ORGANIC LIGHT-EMITTING COMPOUND AND ORGANIC ELECTROLUMINESCENT DEVICE USING SAME

(71) Applicant: DOOSAN CORPORATION, Seoul (KR)

(72) Inventors: Hoe Moon Kim, Suwon-si (KR); Young Mi Beak, Yongin-si (KR); Tae Hyung Kim, Yongin-si (KR); Ho Cheol Park, Suwon-si (KR); Chang Jun Lee, Ansan-si (KR); Jin Yong Shin, Yongin-si (KR)

(73) Assignee: DOOSAN CORPORATION, Seoul (KR)

( * ) Notice: Subject to any disclaimer, the term of this patent is extended or adjusted under 35 U.S.C. 154(b) by 197 days.

(21) Appl. No.: 14/420,569

(22) PCT Filed: Mar. 27, 2013

(86) PCT No.: PCT/KR2013/002526
§ 371 (c)(1),
(2) Date: Apr. 6, 2015

(87) PCT Pub. No.: WO2014/025114
PCT Pub. Date: Feb. 13, 2014

(65) Prior Publication Data
US 2015/0214490 A1  Jul. 30, 2015

(30) Foreign Application Priority Data

Aug. 10, 2012 (KR) .................. 10-2012-0087997
Sep. 19, 2012 (KR) .................. 10-2012-0103937

(51) Int. Cl.
| | | |
|---|---|---|
| H01L 51/50 | (2006.01) |
| H01L 51/00 | (2006.01) |
| C07D 471/14 | (2006.01) |
| C07D 471/22 | (2006.01) |
| C09K 11/06 | (2006.01) |
| C07D 495/14 | (2006.01) |

(52) U.S. Cl.
CPC ........ *H01L 51/0072* (2013.01); *C07D 471/14* (2013.01); *C07D 471/22* (2013.01); *C07D 495/14* (2013.01); *C09K 11/06* (2013.01); *H01L 51/0058* (2013.01); *H01L 51/0061* (2013.01); *H01L 51/0067* (2013.01); *H01L 51/0071* (2013.01); *H01L 51/0074* (2013.01); *C09K 2211/1007* (2013.01); *C09K 2211/1011* (2013.01); *C09K 2211/1029* (2013.01); *C09K 2211/1044* (2013.01); *C09K 2211/1048* (2013.01); *C09K 2211/1051* (2013.01); *C09K 2211/1055* (2013.01); *C09K 2211/1059* (2013.01); *C09K 2211/1062* (2013.01); *C09K 2211/1074* (2013.01); *C09K 2211/1092* (2013.01); *H01L 51/0085* (2013.01); *H01L 51/5016* (2013.01); *H01L 51/5056* (2013.01); *H01L 51/5088* (2013.01)

(58) Field of Classification Search
None
See application file for complete search history.

(56) References Cited

U.S. PATENT DOCUMENTS

2002/0117662 A1  8/2002  Nii
2011/0062429 A1  3/2011  Kai et al.

FOREIGN PATENT DOCUMENTS

| JP | 2012-01513 | * | 1/2012 | ............. H01L 51/50 |
|---|---|---|---|---|
| JP | 2012-001513 A | | 1/2012 | |
| KR | 10-2011-0134923 A | | 12/2011 | |
| WO | 2011/102573 A1 | | 8/2011 | |

OTHER PUBLICATIONS

Bosch, Joan et al., Rearrangement under alkaline conditions of compounds related to tetracyclic Strychnos indole alkaloids Heterocycles (1984), 22(3), 561-4 (STN Abstract Only).*
International Searching Authority, International Search Authority for PCT/KR2013/002526 dated Jul. 30, 2013 [PCT/ISA/210].
Peng, H., et al., "Solvent-Free Synthesis of δ-carbolines/carbazoles from 3-nitro-2-phenylpyridines/2-nitrobiphenyl derivatives using DPPE as a reducing agent", Tetrahedron, 2011, vol. 67, No. 32, p. 5725-5731 (7 pages).
Zhang, Y., et al., "Synthesis of pyrimido [4,5-b]indoles and benzo[4,5]furo[2,3-d]pyrimidines via palladium-catalyzed intramolecular arylation", Tetrahedron Letters, 2002, vol. 43, No. 46, p. 8235-8239 (5 pages).
Japan Patent Office, Communication dated Jun. 21, 2016, issued in counterpart Japanese application No. 2015-526456.

* cited by examiner

*Primary Examiner* — Gregory Clark
(74) *Attorney, Agent, or Firm* — Sughrue Mion, PLLC

(57) ABSTRACT

The present invention relates to a novel indole-based compound having excellent hole injection and transport capabilities, light-emission, and other properties, and to an organic electroluminescent device the luminous efficiency, driving voltage, service life, and other characteristics of which are improved due to containing the compound in one or more organic material layers.

14 Claims, No Drawings

ORGANIC LIGHT-EMITTING COMPOUND AND ORGANIC ELECTROLUMINESCENT DEVICE USING SAME

CROSS REFERENCE TO RELATED APPLICATIONS

This application is a National Stage of International Application No. PCT/KR2013/002526 filed Mar. 27, 2013, claiming priority based on patent application Ser. No. KR10-2012-0087997 filed Aug. 10, 2012, the contents of all of which are incorporated herein by reference in their entirety.

TECHNICAL FIELD

The present disclosure relates to a novel organic light-emitting compound and an organic electroluminescent device using the same, and more particularly, to a novel indole-based compound having excellent hole injection and transport capabilities, light-emitting capabilities, and the like, and an organic electroluminescent device which contains the indole-based compound in one or more organic material layers thereof so as to improve characteristics such as light-emitting efficiency, driving voltage, and a lifespan.

BACKGROUND ART

In a study on an organic electroluminescent (EL) device (hereinafter, simply referred to as 'organic EL device'), which has continued from the start point of observing an organic thin film light emission by Bernanose in the 1950s to blue electric light emission using an anthracene single crystal in 1965, an organic EL device having a lamination structure, which is divided into functional layers of a hole layer and a light-emitting layer, was proposed by Tang in 1987. Until now, the organic EL device has been developed in the form of introducing each characteristic organic material layer into a device in order to manufacture the organic EL device having high efficiency and a long service life (lifespan), thereby leading to the development of specialized materials used therein.

When voltage is applied between two electrodes of the organic EL device, holes are injected into the organic material layer at the anode and electrons are injected into the organic material layer at the cathode. When the injected holes and electrons meet each other, an exciton is formed, and when the exciton falls down to a bottom state, light is emitted. Materials used as the organic material layer may be classified into a light-emitting material, a hole injection material, a hole transporting material, an electron transporting material, an electron injection material, and the like according to the function.

Materials for forming the light-emitting layer of the organic EL device may be divided into blue, green, and red light-emitting materials according to the light-emitting color. In addition, yellow and orange light-emitting materials are also used as a light-emitting material for implementing a much better natural color. Further, a host/dopant system may be used as a light-emitting material in order to enhance color purity and light-emitting efficiency through an energy transfer. Dopant materials may be divided into a fluorescent dopant using an organic material and a phosphorescent dopant in which a metal complex compound including heavy atoms such as Ir and Pt is used. Since the development of the phosphorescent material may theoretically enhance light-emitting efficiency by up to 4 times compared to the development of the fluorescent material, interests in not only phosphorescent dopant, but also phosphorescent host materials have come into focus.

As the hole transporting layer, the hole blocking layer and the electron transporting layer, NPB, BCP, Alq$_3$ and the like represented by the following Formulae have been widely known until now, and for the light-emitting material, anthracene derivatives have been reported as a fluorescent dopant/host material. In particular, for the phosphorescent material having a great advantage in terms of enhancing the efficiency, metal complex compounds including Ir, such as Firpic, Ir(ppy)$_3$ and (acac)Ir(btp)$_2$, have been used as blue, green and red dopant materials. Until now, CBP have exhibited excellent characteristics as a phosphorescent host material.

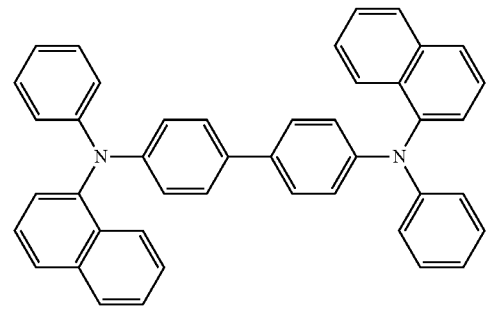

NPB

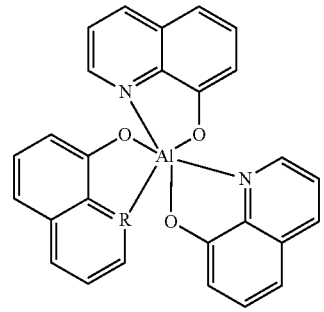

Alq3

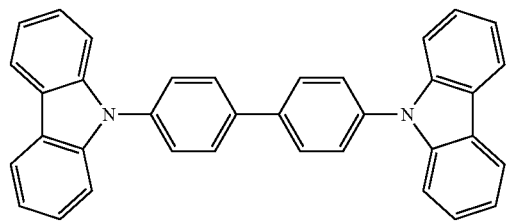

CBP

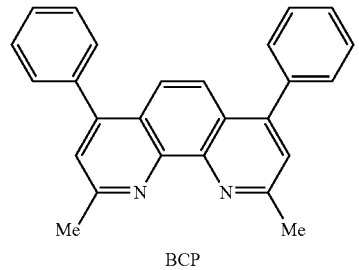

BCP

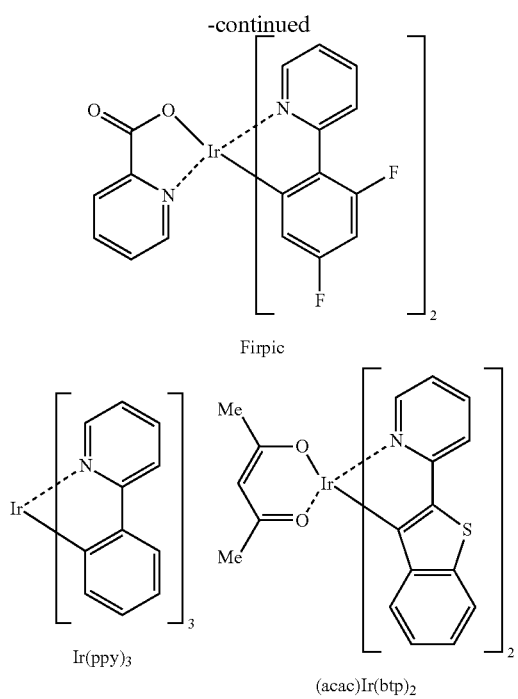

Firpic

Ir(ppy)₃     (acac)Ir(btp)₂

However, the existing materials are advantageous in terms of light-emitting characteristics, but have a low glass transition temperature and very poor thermal stability, and thus fall short of a level that sufficiently satisfies the lifespan in the organic EL device.

DISCLOSURE

Technical Problem

The present disclosure has been contrived to solve the problem, and an object of the present disclosure is to provide a novel indole-based material which is used as a light-emitting layer, and thus may enhance driving voltage, light-emitting efficiency, and the like of a device, and an organic electroluminescent device using the same.

Further, other technical problems which the present disclosure intends to solve are not limited to the technical problems which have been mentioned above, and still other technical problems which have not been mentioned will be apparently understood to those skilled in the art to which the present disclosure pertains from the following description.

Technical Solution

In order to achieve the object, the present disclosure provides a compound represented by the following Formula 1.

[Formula 1]

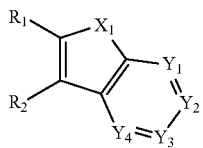

In the formula,
$Y_1$ to $Y_4$ are the same as or different from each other, and are each independently selected from N and $CR_3$, and at least one of $Y_1$ and $Y_2$, $Y_2$ and $Y_3$, or $Y_3$ and $Y_4$ is $CR_3$, and forms a fused ring represented by the following Formula 2;

[Formula 2]

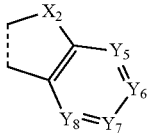

the dotted line means a site where a fusion (condensation) with the compound of Formula 1 occurs;
$Y_5$ to $Y_8$ are the same as or different from each other, and are each independently selected from N and $CR_4$,
$X_1$ and $X_2$ are the same as or different from each other, and are each independently selected from O, S, Se, $N(Ar_1)$, $C(Ar_2)(Ar_3)$, and $Si(Ar_4)(Ar_5)$, and here, at least one of $X_1$ and $X_2$ is $N(Ar_1)$, and
$R_1$ to $R_4$ are the same as or different from each other, and are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these form or do not form a fused ring with an adjacent group;
$Ar_1$ to $Ar_5$ are the same as or different from each other, and are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and
provided that $Y_1$ to $Y_8$ include at least one N.

Furthermore, the present disclosure provides an organic EL device including (i) an anode, (ii) a cathode, and (iii) an organic material layer including one or more layers interposed between the anode and the cathode, in which at least one organic material layer comprises one or more of the compounds represented by Formula 1.

Here, it is preferred that the compound represented by Formula 1 is used as a phosphorescent host of a light-emitting layer.

Advantageous Effects

The novel indole-based compound represented by Formula 1 according to the present disclosure may exhibit excellent heat resistance, hole injection and transport capabilities, light-emitting capabilities, and the like.

Therefore, an organic EL device including the compound represented by Formula 1 as a phosphorescent/fluorescent host, a dopant, and the like of a hole injection/transporting layer or a light-emitting layer may be greatly enhanced in terms of light-emitting performance, driving voltage, a lifespan, efficiency, and the like, and thus may be effectively applied to a full-color display panel, and the like.

BEST MODE

The present disclosure provides a novel indole-based compound having a molecular weight larger than that of a material for an organic EL device [for example: 4,4-dicarbazolybiphenyl (hereinafter, represented as CBP)] in the related art, and excellent driving voltage characteristics and efficiency.

The novel indole-based compound represented by Formula 1 according to the present disclosure has a wide band-gap (sky blue to red) because a fused carbon ring or a fused heterocyclic moiety, preferably a fused heterocyclic moiety, is connected to an indole-based basic structure, and the energy level is controlled by various substituents. Accordingly, since phosphorescent characteristics of the device may be improved, and simultaneously, electron and/or hole transporting capabilities, light-emitting efficiency, driving voltage, lifespan characteristics, and the like may be improved, the indole-based compound may be applied to not only a light-emitting layer but also a hole transporting layer, an electron transporting layer, a light-emitting host, and the like by introducing various substituents. In particular, due to the indole-based basic structure, the indole-based compound may exhibit excellent characteristics as a light-emitting host material compared to the existing CBP.

Further, the molecular weight of the compound is significantly increased due to various aromatic ring substituents to be introduced into the indole-based backbone structure, so that the glass transition temperature is enhanced, and accordingly, the indole-based compound may have higher thermal stability than that of the CBP in the related art. Therefore, a device including the novel compound represented by Formula 1 according to the present disclosure may greatly enhance durability and lifespan characteristics.

Furthermore, when the compound represented by Formula 1 according to the present disclosure is adopted as a hole injection/transporting layer, a blue, green, and/or red phosphorescent host material, or a fluorescent host material of an organic EL device, much better effects may be exhibited in terms of efficiency and a lifespan compared to the CBP. Therefore, the compound according to the present disclosure may greatly contribute to the improvement of performance and the enhancement of lifespan, of the organic EL device.

Meanwhile, in $R_1$ to $R_4$ and $Ar_1$ to $Ar_5$ of the above-described Formula 1, the substituent in which the term 'substituted or unsubstituted' is described, for example, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group may be each independently substituted with one or more substituents selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group.

In the compound represented by Formula 1 according to the present disclosure, it is preferred that $R_1$ to $R_4$ are the same as or different from each other, and are each independently selected from the group consisting of hydrogen, deuterium, halogen, a cyano group, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group. In this case, when a wide band-gap and thermal stability are considered, it is more preferred that $R_1$ to $R_4$ are each independently hydrogen, a $C_6$ to $C_{60}$ aryl group (for example: phenyl, naphthyl, and bisphenyl), or a heteroaryl group having 5 to 60 nuclear atoms (for example: pyridine).

Further, in the compound represented by Formula 1 according to the present disclosure, $X_1$ and $X_2$ may be each independently selected from O, S, Se, N(Ar$_1$), C(Ar$_2$)(Ar$_3$), and Si(Ar$_4$)(Ar$_5$), herein, at least one of $X_1$ and $X_2$ may be N(Ar$_1$), and preferably, both $X_1$ and $X_2$ are N(Ar$_1$).

In addition, $Y_1$ to $Y_8$ are each independently selected from N and CR$_4$, and include at least one N. Preferred is the case where N is 1.

Furthermore, in the compound represented by Formula 1 according to the present disclosure, $Ar_1$ to $Ar_5$ may be each independently selected from the group consisting of a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group. Preferably, $Ar_1$ to $Ar_5$ may be each independently a $C_1$ to $C_{40}$ alkyl group, a $C_6$ to $C_{60}$ aryl group, a heteroaryl group having 5 to 60 nuclear atoms, or a $C_6$ to $C_{60}$ arylamine group, and in this case, the $C_6$ to $C_{60}$ aryl group, the heteroaryl group having 5 to 60 nuclear atoms, and the $C_6$ to $C_{60}$ arylamine group may be each substituted with a $C_1$ to $C_{40}$ alkyl group, a $C_6$ to $C_{60}$ aryl group, and a heteroaryl group having 5 to 60 nuclear atoms.

It is preferred that the substituents of the compound of Formula 1 according to the present disclosure, $Ar_1$ to $Ar_5$ are each independently selected from the group of the following substituents (function groups), for example, S1 to S177. However, the selection is not particularly limited thereto.

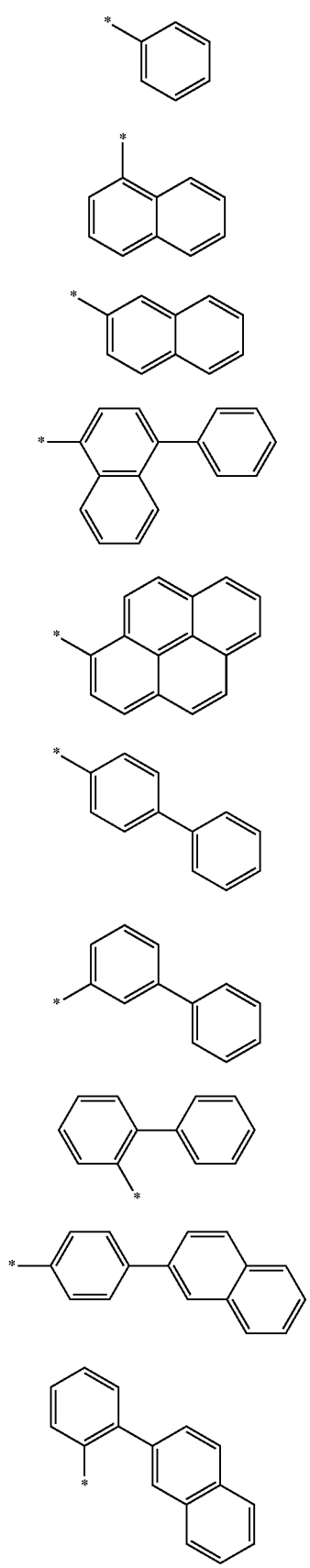

-continued
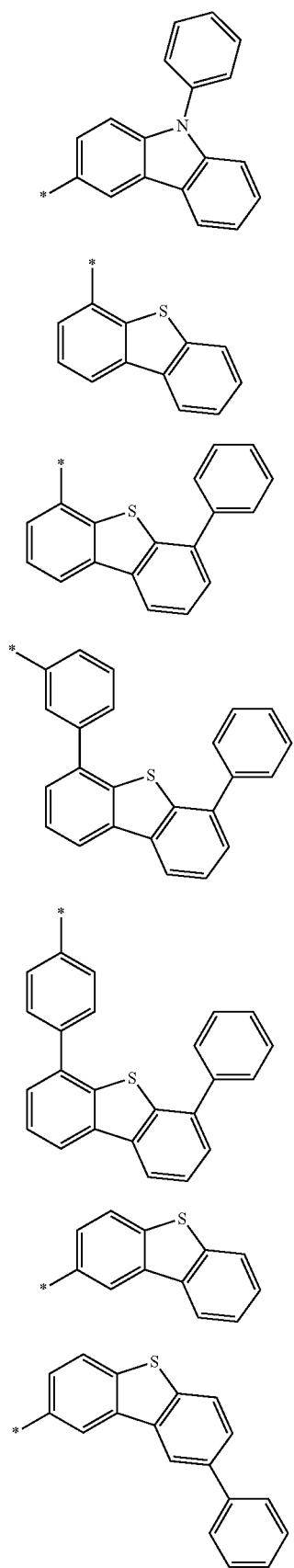
S19
S20
S21
S22
S23
S24
S25
-continued
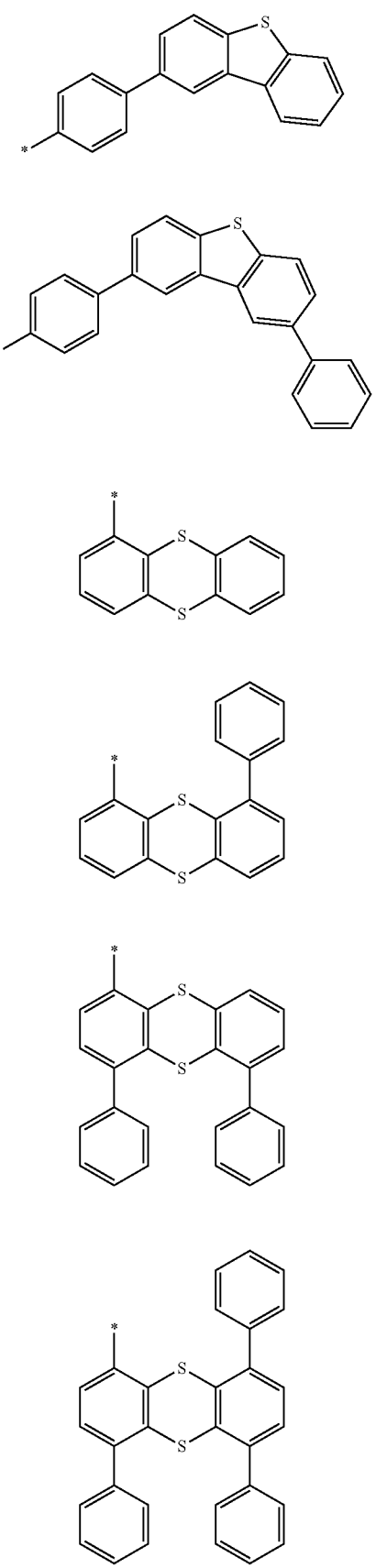
S26
S27
S28
S29
S30
S31

S32 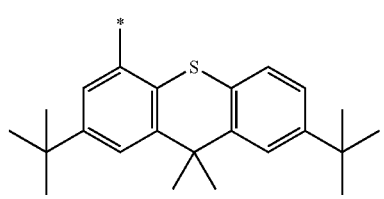
S33 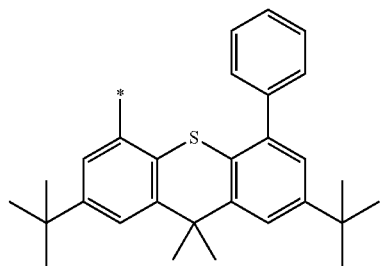
S34 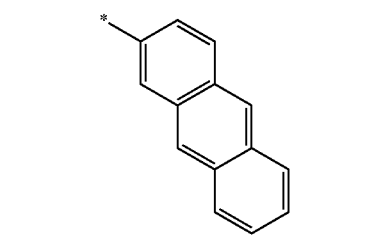
S35 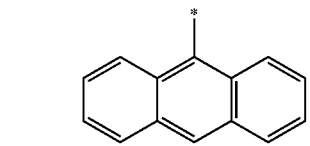
S36 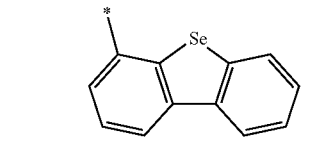
S37 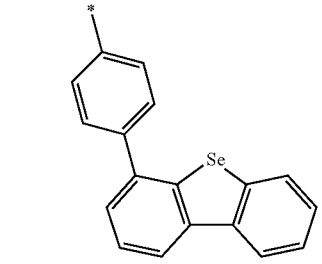
S38 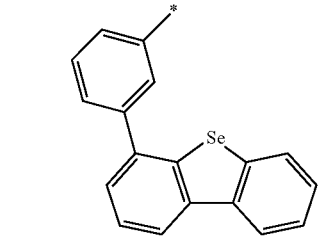
S39 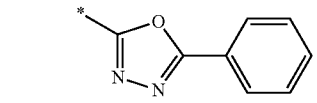
S40 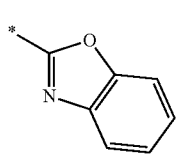
S41 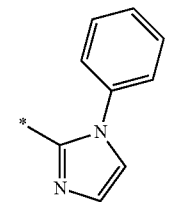
S42 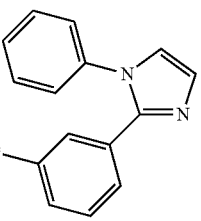
S43 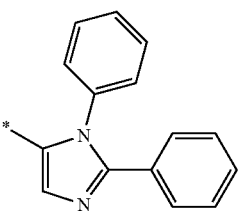
S44 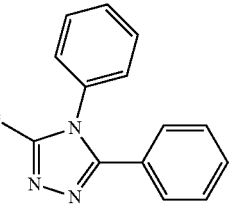
S45 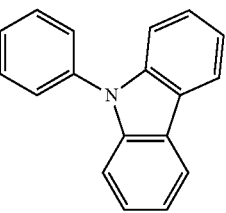
S46 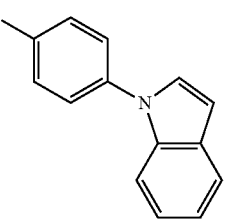

| | |
|---|---|
| 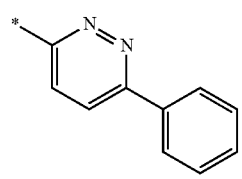 | S47 |
| 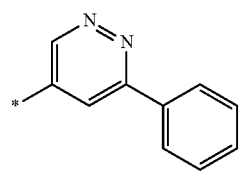 | S48 |
| 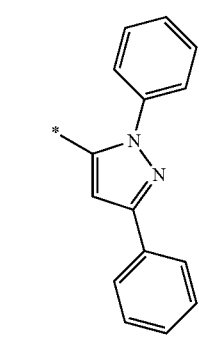 | S49 |
| 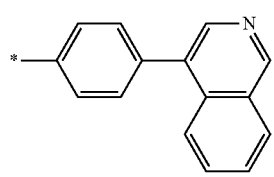 | S50 |
| 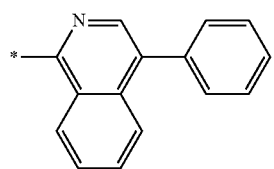 | S51 |
| 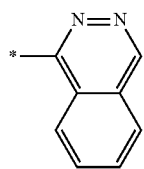 | S52 |
| 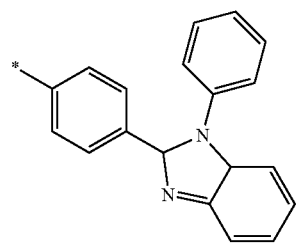 | S53 |
| 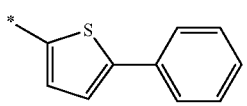 | S54 |
| 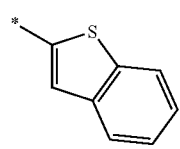 | S55 |
| 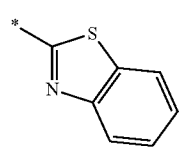 | S56 |
| 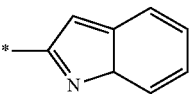 | S57 |
| 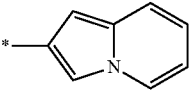 | S58 |
| 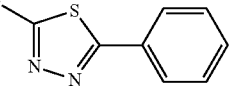 | S59 |
| 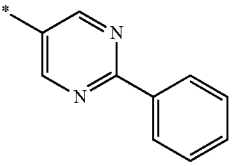 | S60 |
| 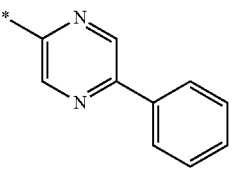 | S61 |
| 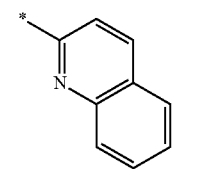 | S62 |
| 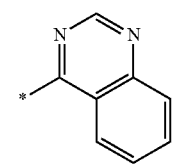 | S63 |
| 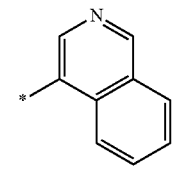 | S64 |

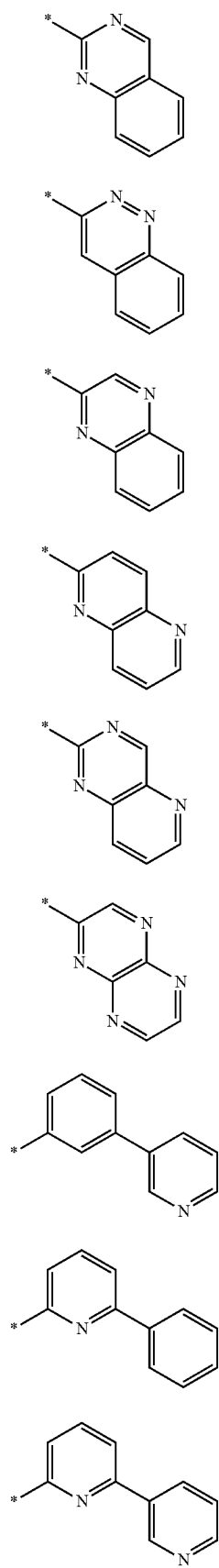
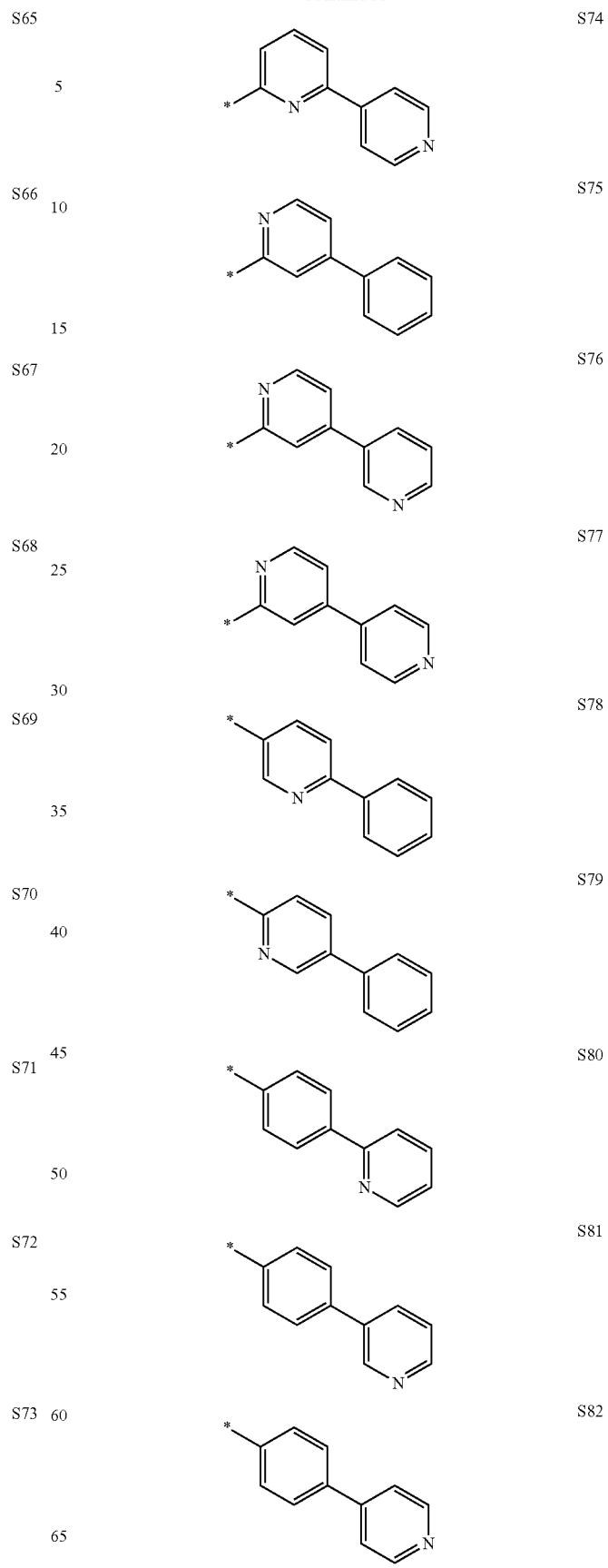

S83 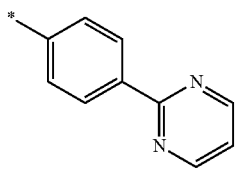
S84 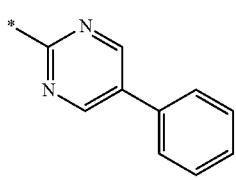
S85 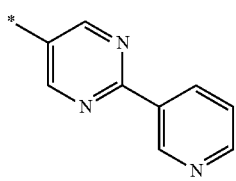
S86 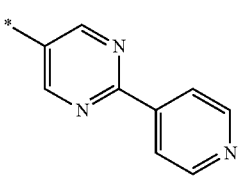
S87 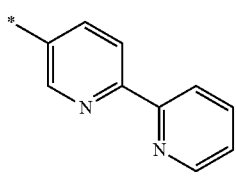
S88 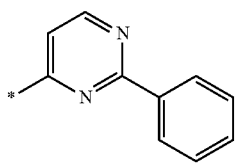
S89 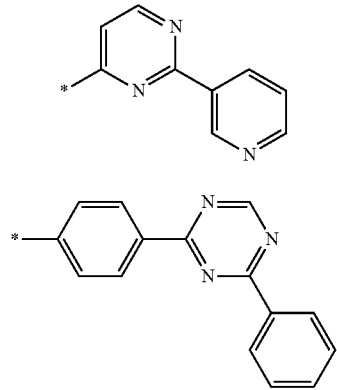
S90
S91 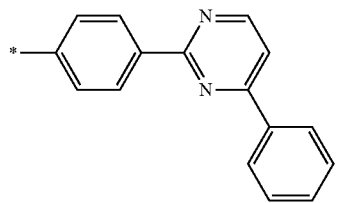
S92 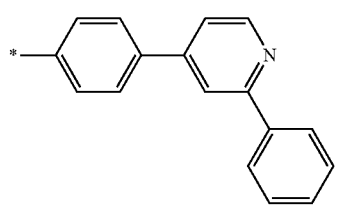
S93 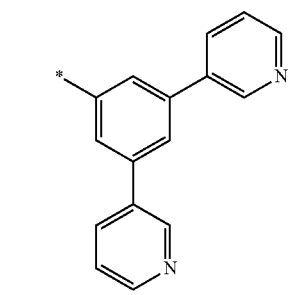
S94 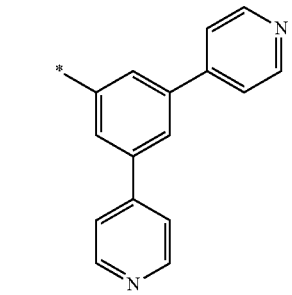
S95 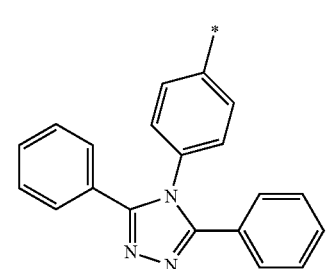
S96 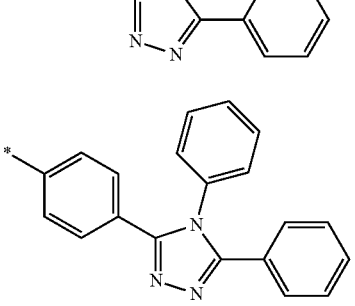

S97

S98

S99

S100

S101

S102

S103

S104

S105

S106

S107
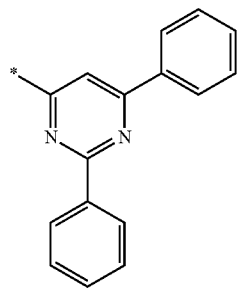
S108
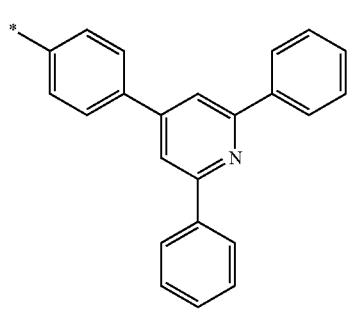
S109
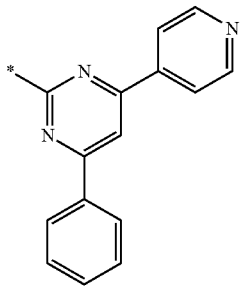
S110
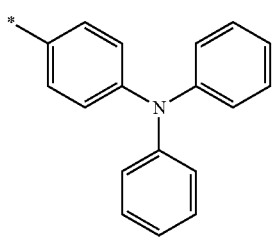
S111
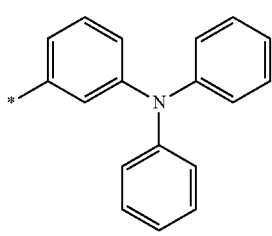
S112
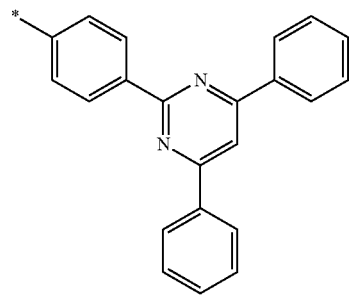
S113
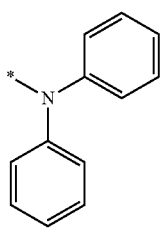
S114
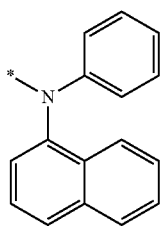
S115
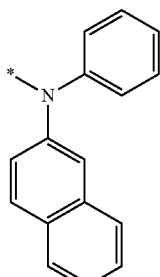
S116
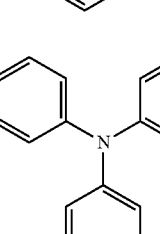
S117
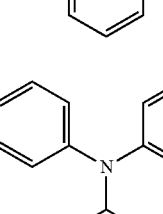
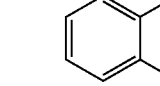

-continued

S118

S119

S120

S121

S122

-continued

S123

S124

S125

S126

S127

S128 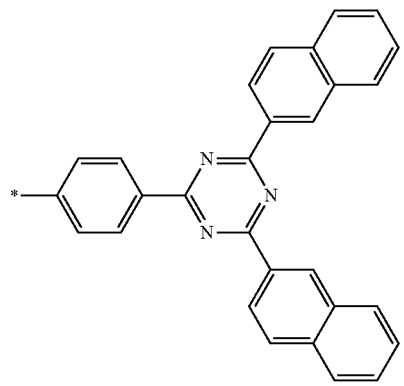
S129 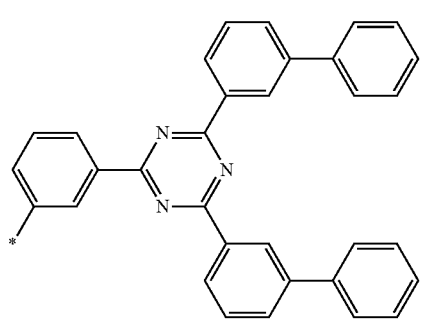
S130 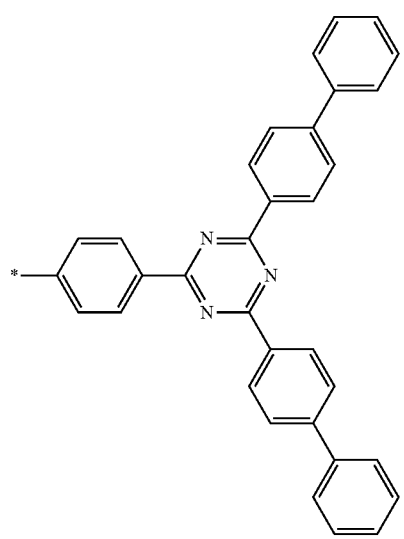
S131 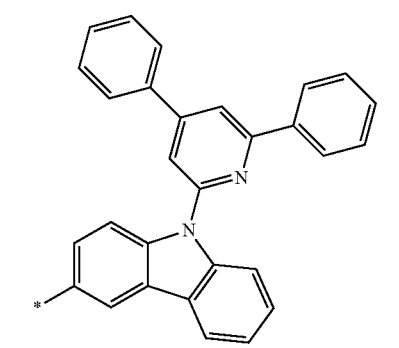
S132 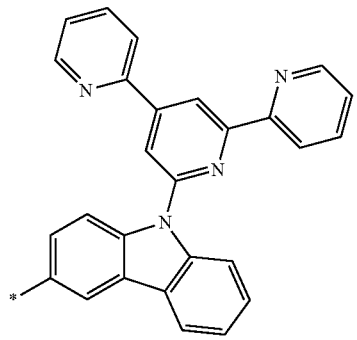
S133 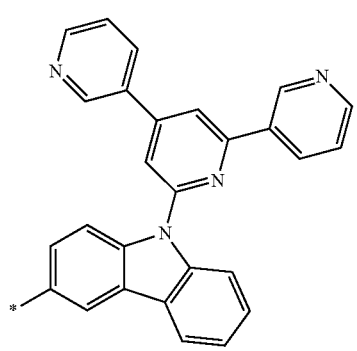
S134 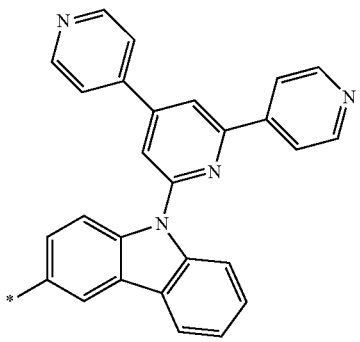
S135 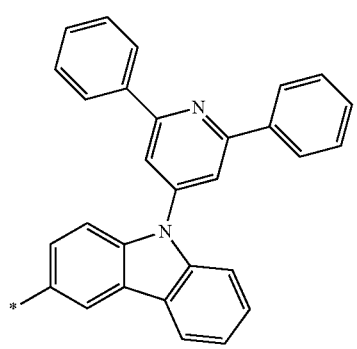

-continued
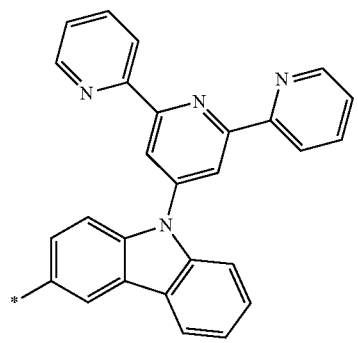
S136
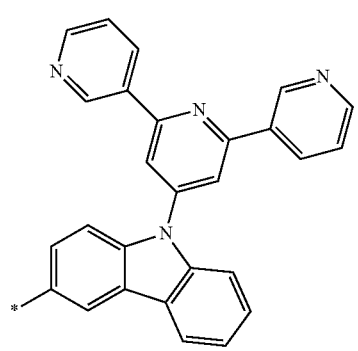
S137
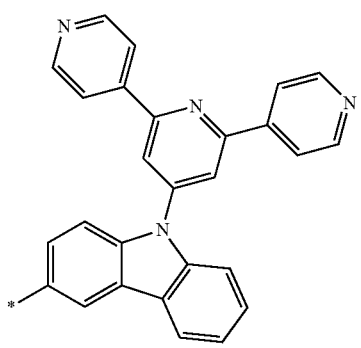
S138
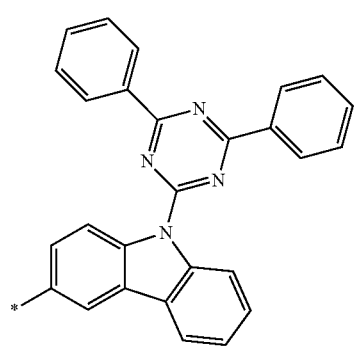
S139
-continued
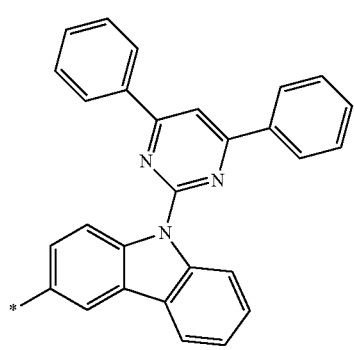
S140
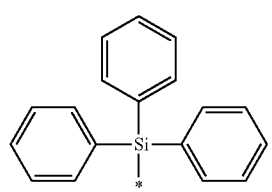
S141
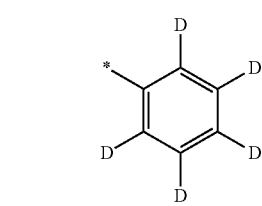
S142
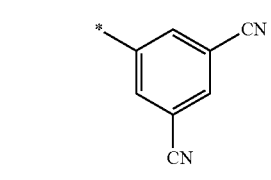
S143
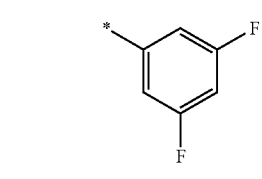
S144
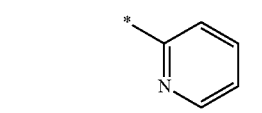
S145
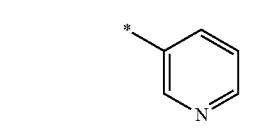
S146
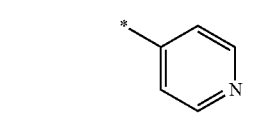
S147
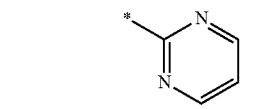
S148

-continued
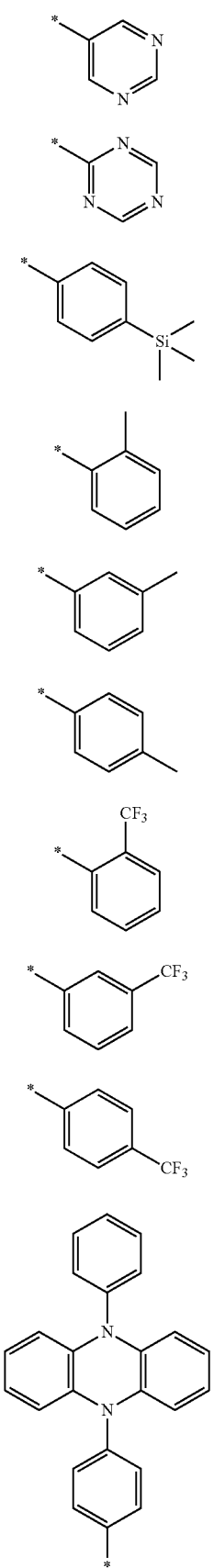
S149
S150
S151
S152
S153
S154
S155
S156
S157
S158
-continued
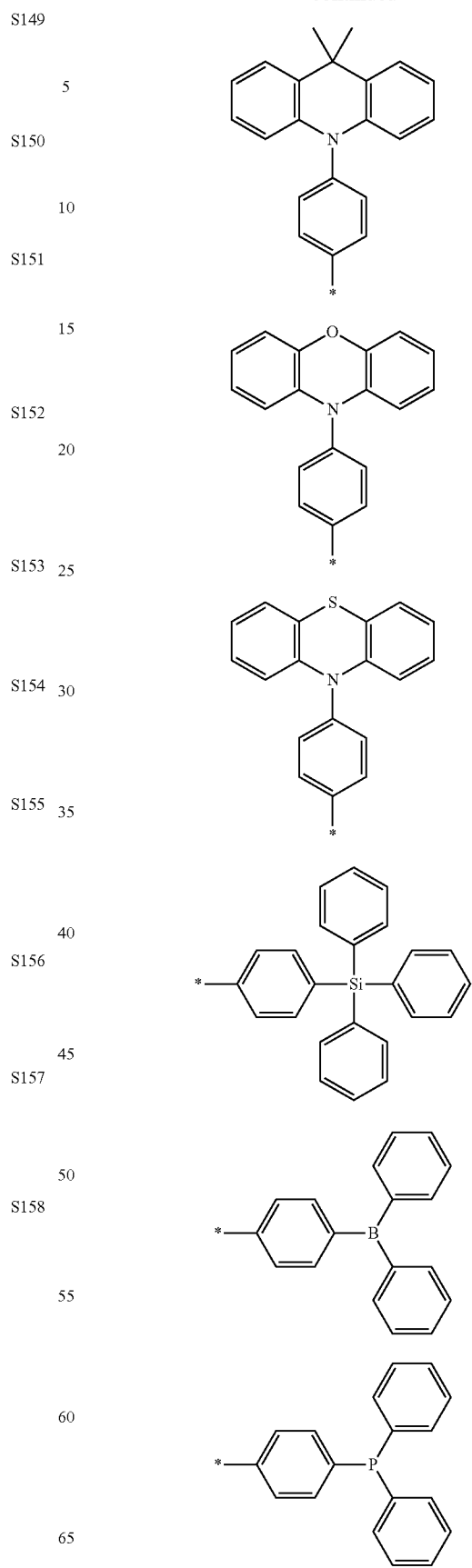
S159
S160
S161
S162
S163
S164

S165
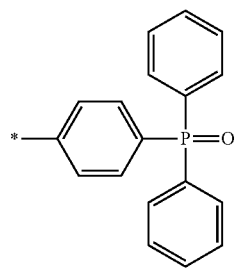
S166
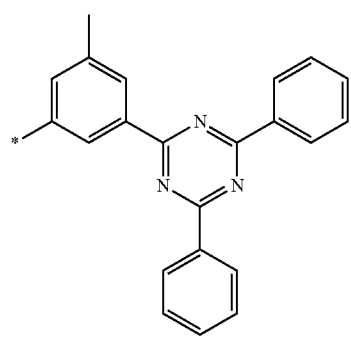
S167
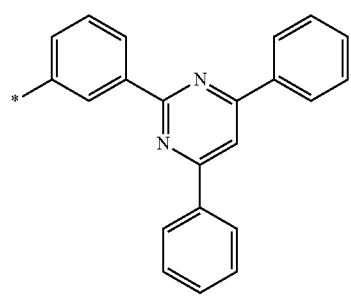
S168
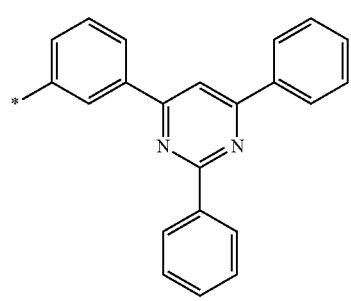
S169
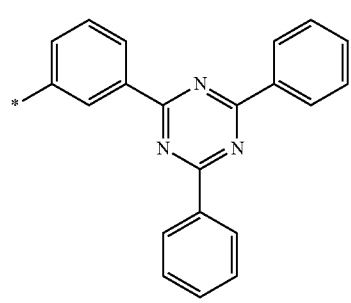
S170
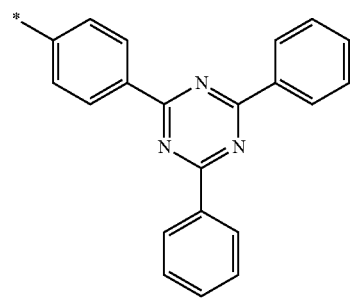
S171
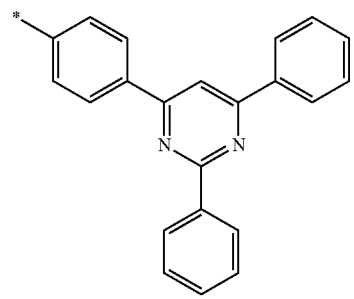
S172
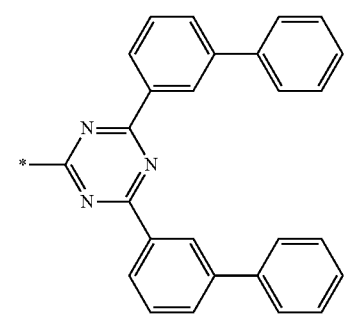
S173
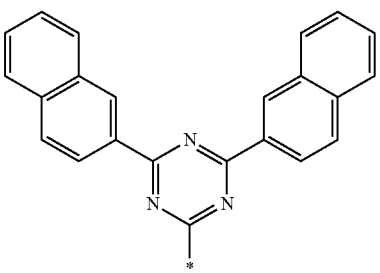
S174
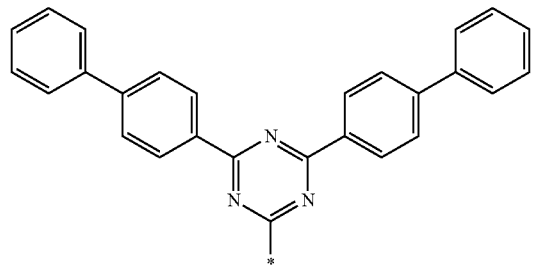

-continued

S175 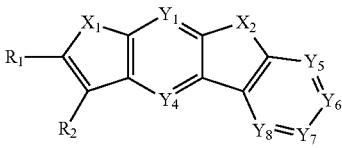

[Formula 4]

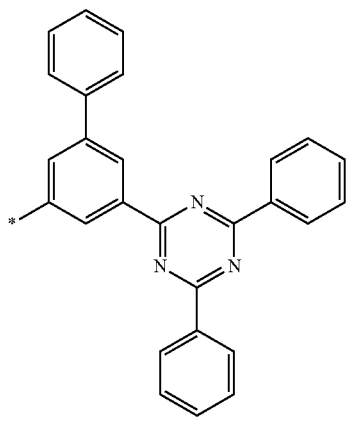

S176 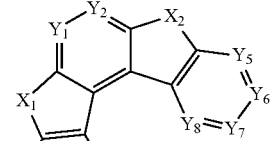

[Formula 5]

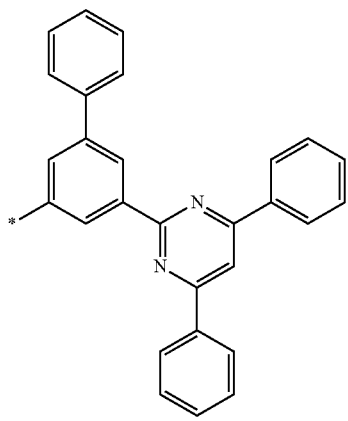

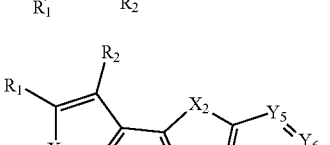

[Formula 6]

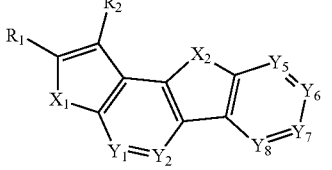

[Formula 7]

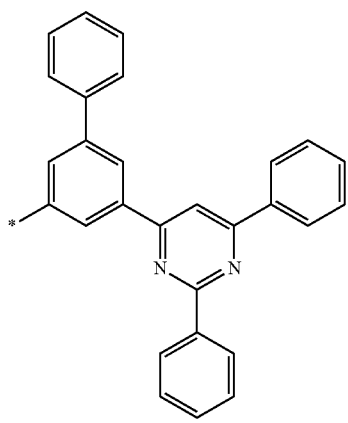

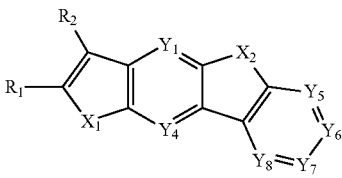

[Formula 8]

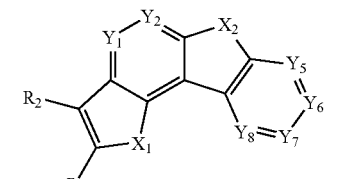

S177

In the formulae, $X_1$ and $X_2$, $Y_1$ to $Y_8$, $R_1$, and $R_2$ are the same as those defined in Formula 1.

More specifically, $X_1$ and $X_2$ are each independently selected from O, S, Se, $N(Ar_1)$, $C(Ar_2)(Ar_3)$, and $Si(Ar_4)(Ar_5)$, here, at least one of $X_1$ and $X_2$ may be $N(Ar_1)$, and preferably, both $X_1$ and $X_2$ are $N(Ar_1)$.

Further, $Y_1$ to $Y_8$ are each independently selected from N and $CR_4$, and include at least one N. Preferred is the case where N is 1.

The "unsubstituted alkyl" used in the present disclosure is a straight or branched saturated hydrocarbon having 1 to 40 carbon atoms, and examples thereof include methyl, ethyl, propyl, isobutyl, sec-butyl, pentyl, iso-amyl, hexyl, and the like.

The "unsubstituted aryl" means an aromatic site having 6 to 60 carbon atoms, which is a single ring or a combination of two or more rings. Two or more rings may be simply pendant to each other or pendant to each other in a fused form.

The "unsubstituted heteroaryl" means a monoheterocyclic or polyheterocyclic aromatic site having 5 to 60 nuclear atoms, and one or more carbons in the ring, preferably 1 to 3 carbons, are substituted with a hetero atom such as N, O, S, or Se. Two or more rings may be simply pendant to each other or pendant to each other in a fused form, and furthermore, it is interpreted that a form that is fused with an aryl group is also included.

The compound represented by Formula 1 according to the present disclosure may be more embodied as any one compound of the following Formulae 3 to 8.

[Formula 3]

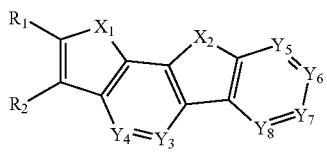

The "fused ring (condensed ring)" means a fused aliphatic ring, a fused aromatic ring, a fused heteroaliphatic ring, a fused heteroaromatic ring, or a combined form thereof.

The aforementioned compound represented by Formula 1 according to the present disclosure may be more embodied as the formulae exemplified below, for example, Formulae C-1 to C-291. However, the compound represented by Formula 1 according to the present disclosure is not limited by those exemplified below.

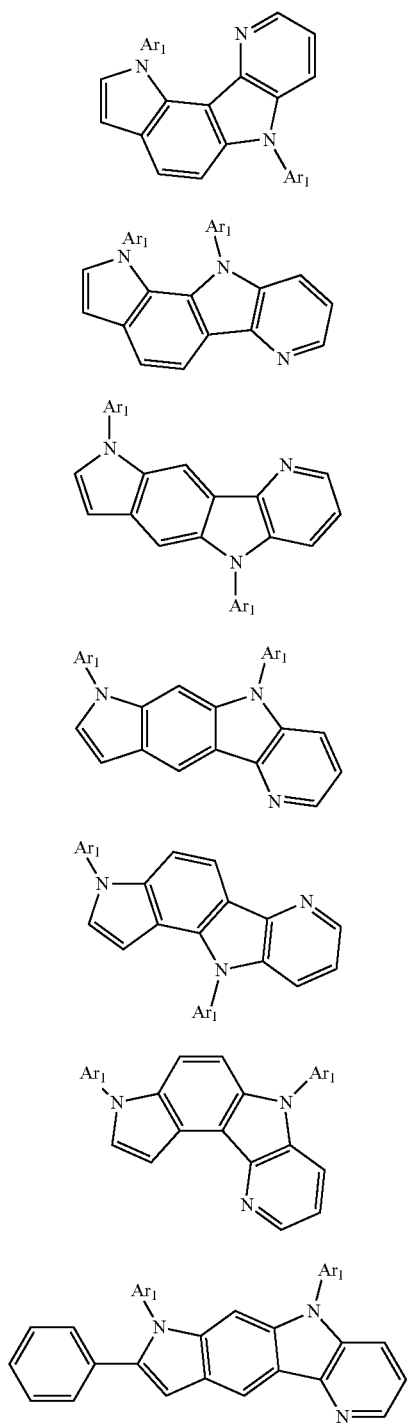

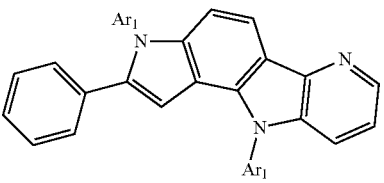

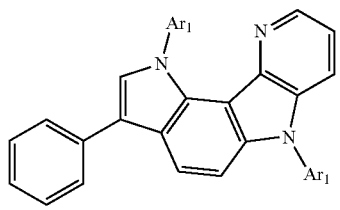

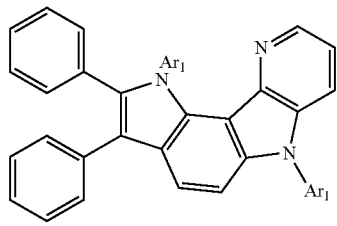

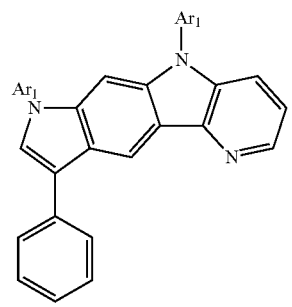

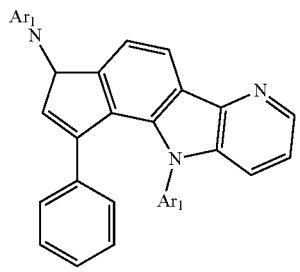

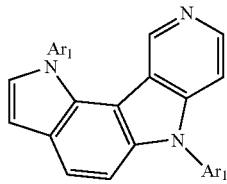

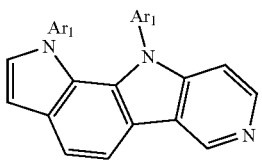

C-15
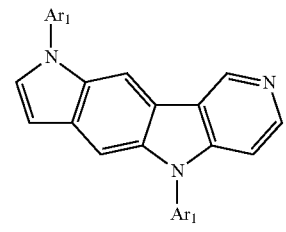
C-16
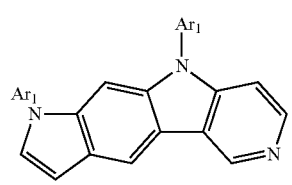
C-17
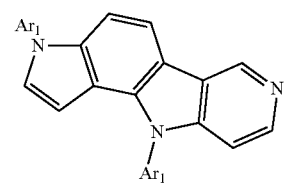
C-18
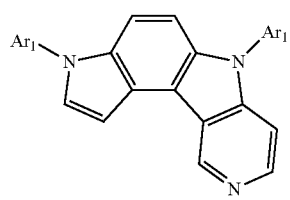
C-19
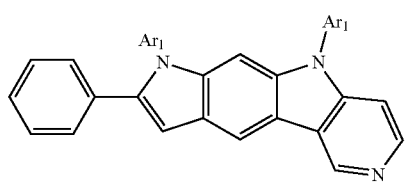
C-20
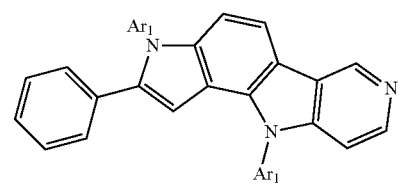
C-21
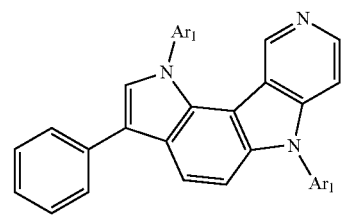
C-22
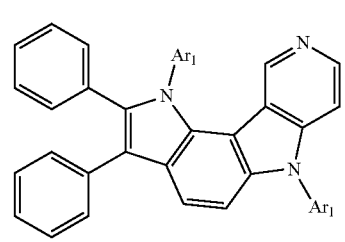
C-23
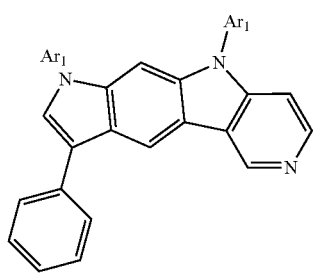
C-24
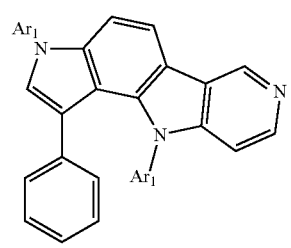
C-25
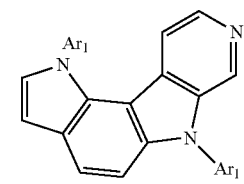
C-26
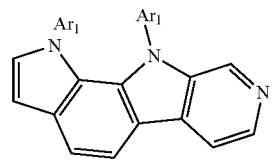
C-27
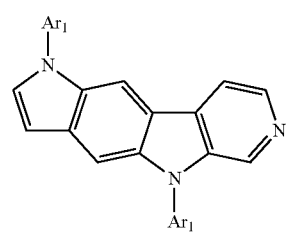
C-28
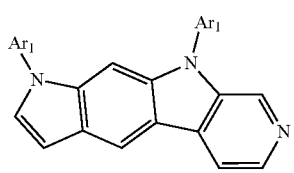
C-29
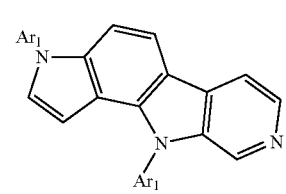

C-30 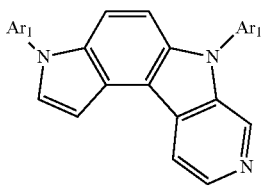
C-31 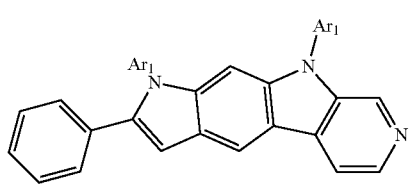
C-32 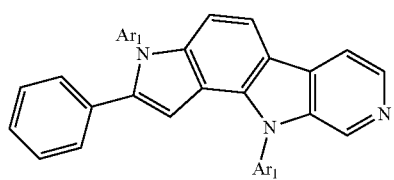
C-33 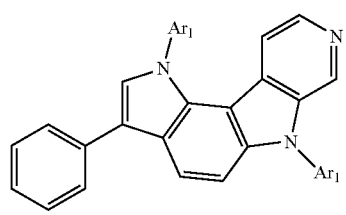
C-34 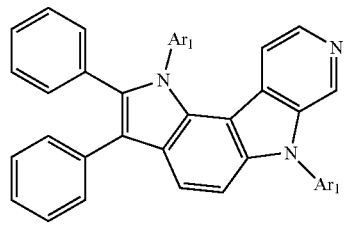
C-35 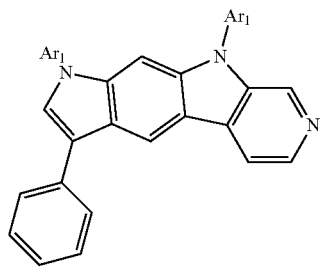
C-36 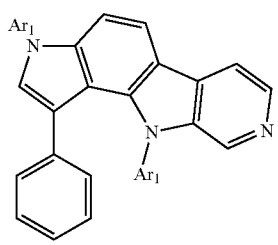
C-37 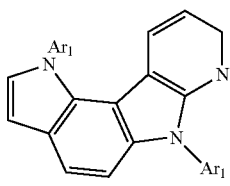
C-38 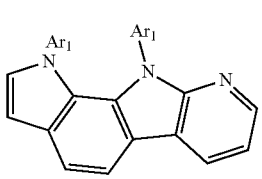
C-39 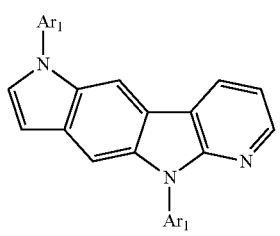
C-40 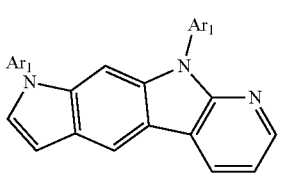
C-41 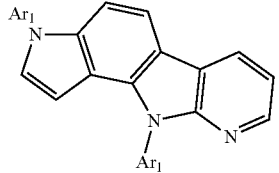
C-42 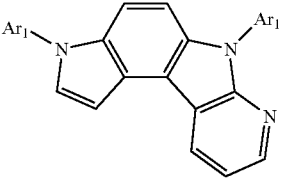
C-43 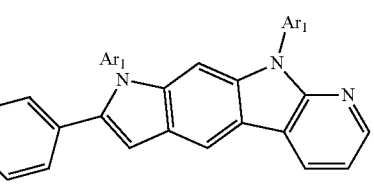
C-44 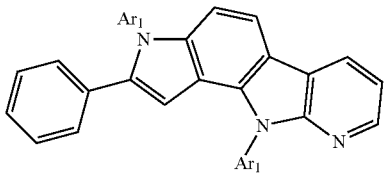

-continued
C-45
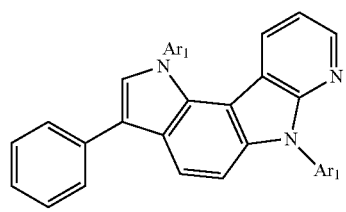
C-46
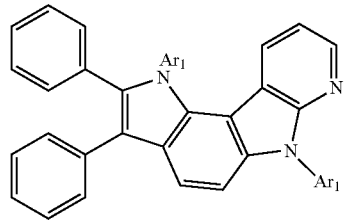
C-47
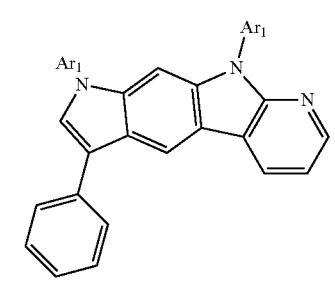
C-48
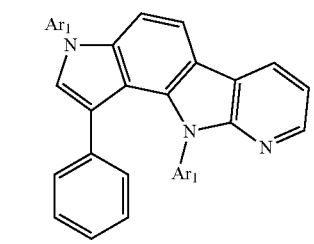
C-49
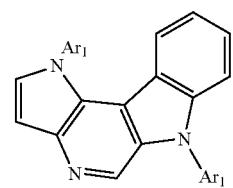
C-50
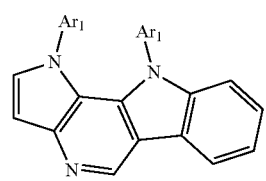
C-51
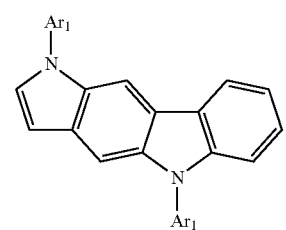
-continued
C-52
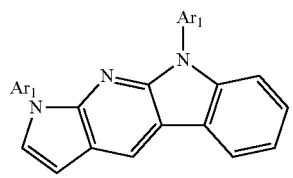
C-53
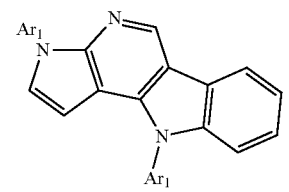
C-54
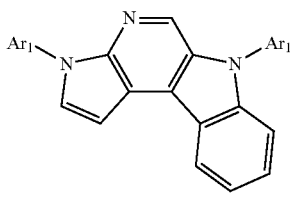
C-55
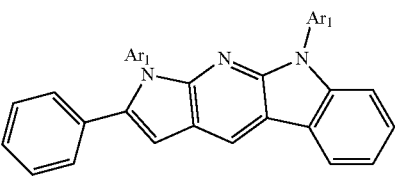
C-56
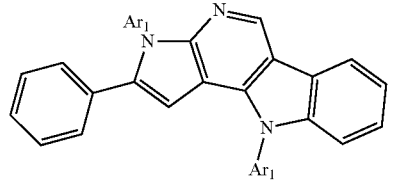
C-57
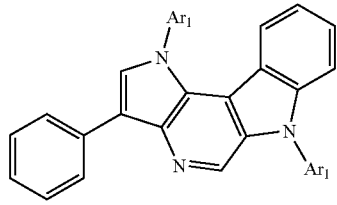
C-58
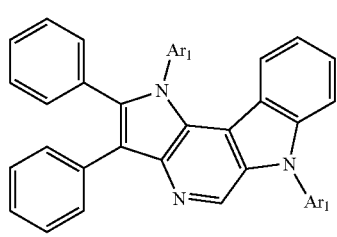

C-59
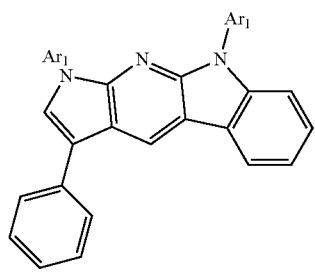
C-60
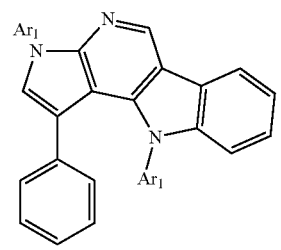
C-61
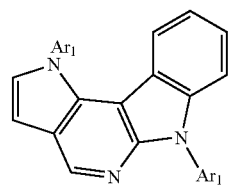
C-62
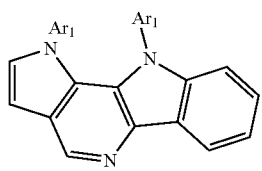
C-63
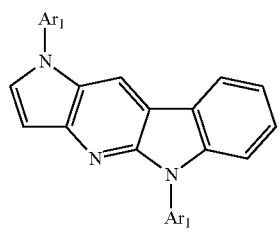
C-64
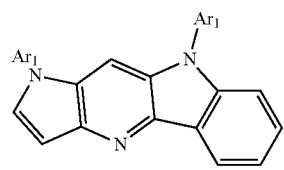
C-65
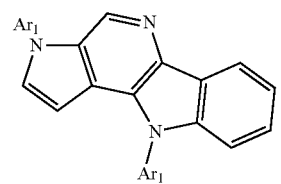
C-66
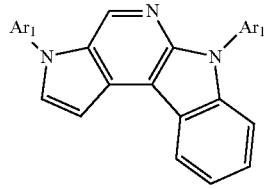
C-67
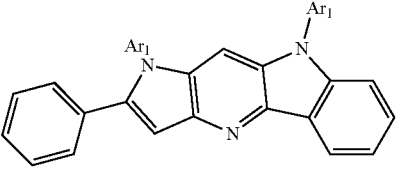
C-68
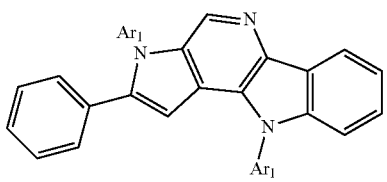
C-69
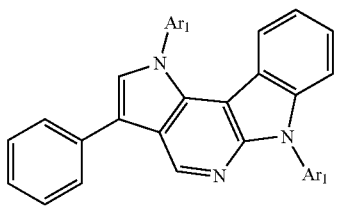
C-70
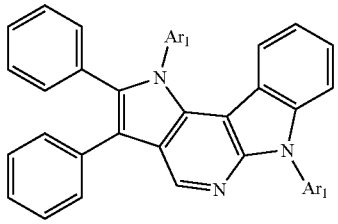
C-71
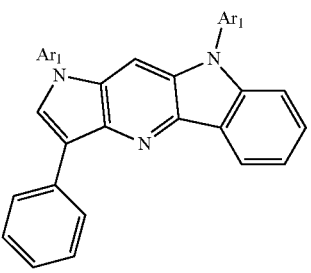
C-72
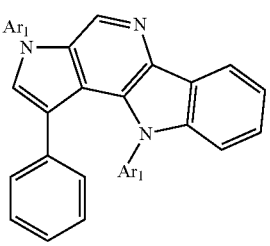

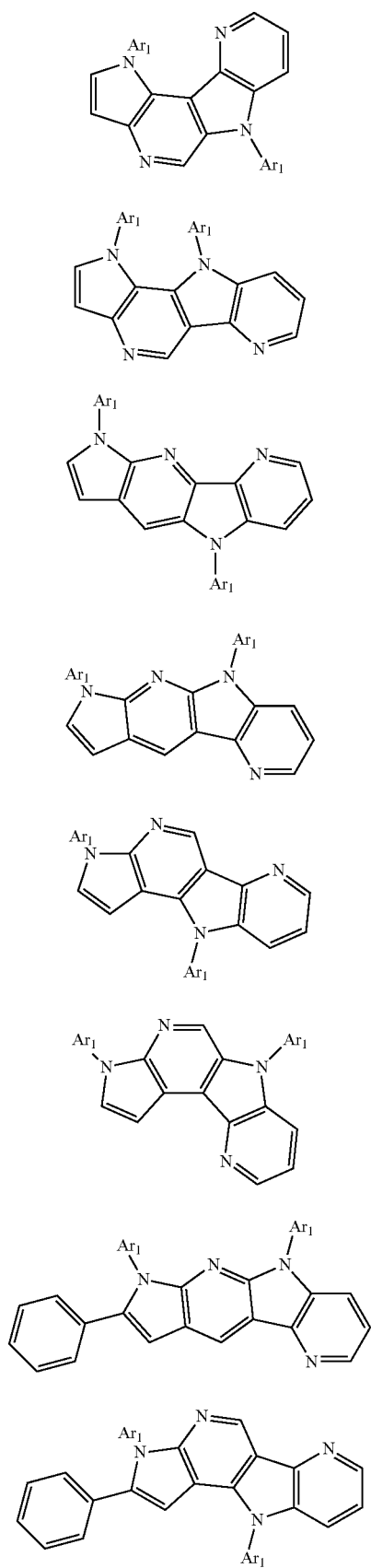
C-73
C-74
C-75
C-76
C-77
C-78
C-79
C-80
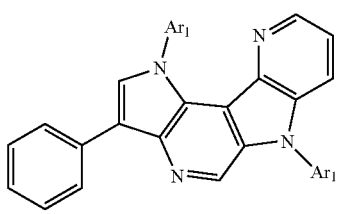
C-81
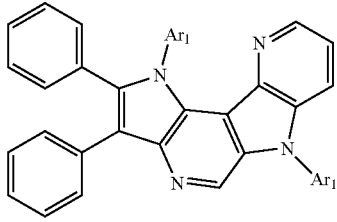
C-82
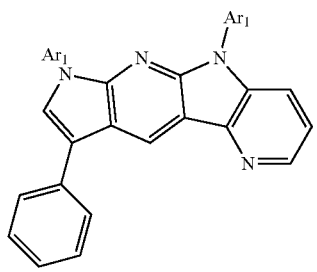
C-83
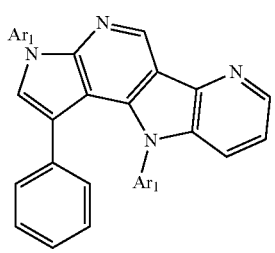
C-84
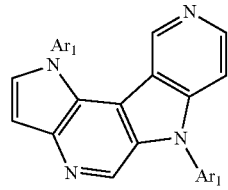
C-85
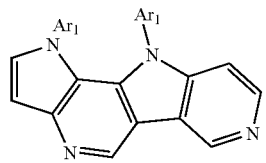
C-86
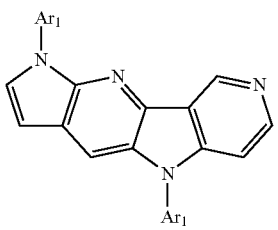
C-87

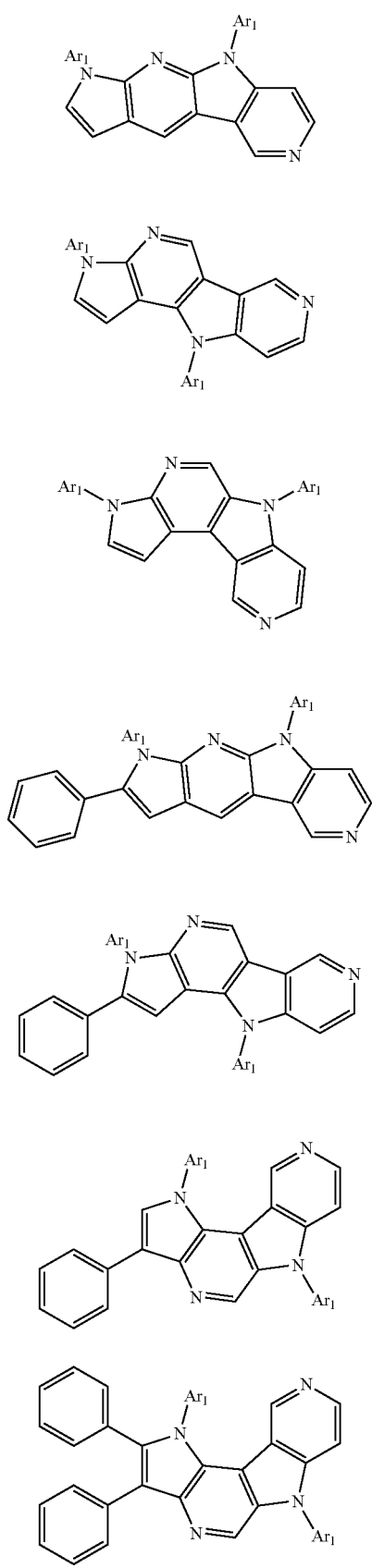
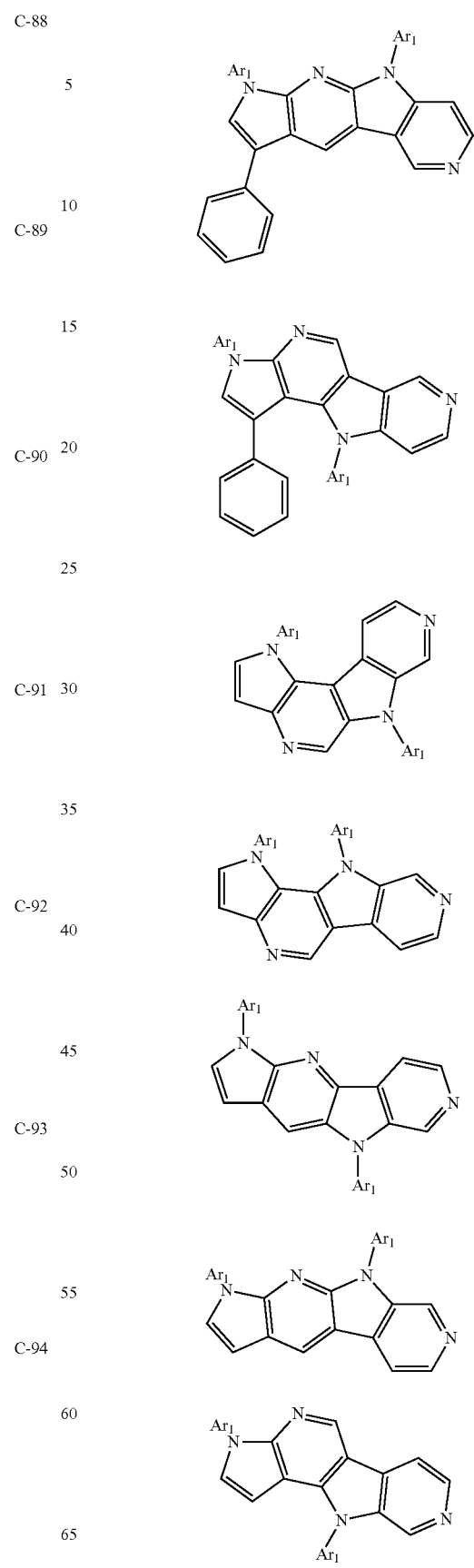

C-102, C-103, C-104, C-105, C-106, C-107, C-108, C-109, C-110, C-111, C-112, C-113, C-114, C-115, C-116

C-117
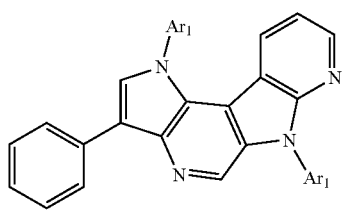
C-118
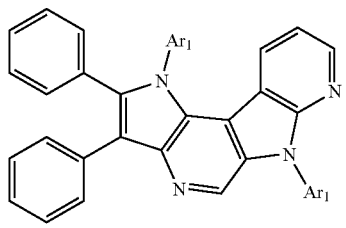
C-119
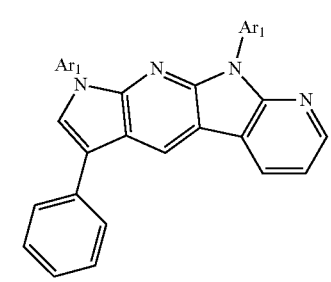
C-120
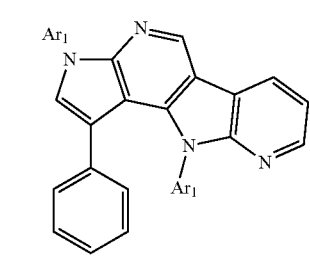
C-121
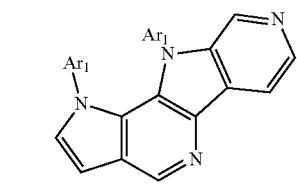
C-122
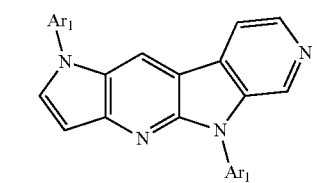
C-123
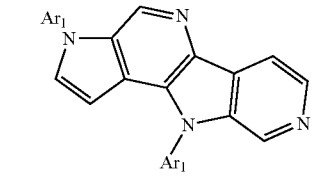
C-124
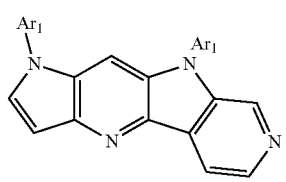
C-125
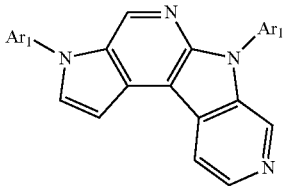
C-126
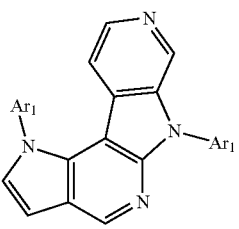
C-127
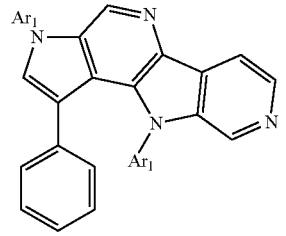
C-128
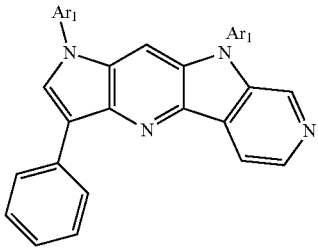
C-129
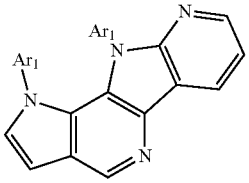
C-130
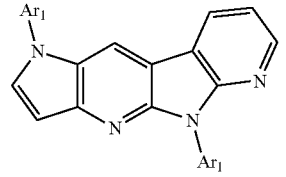

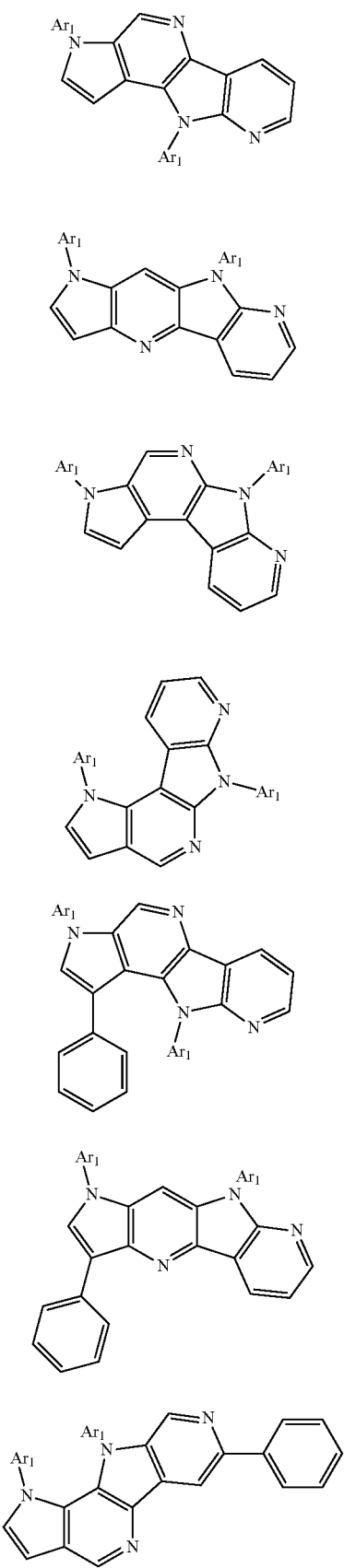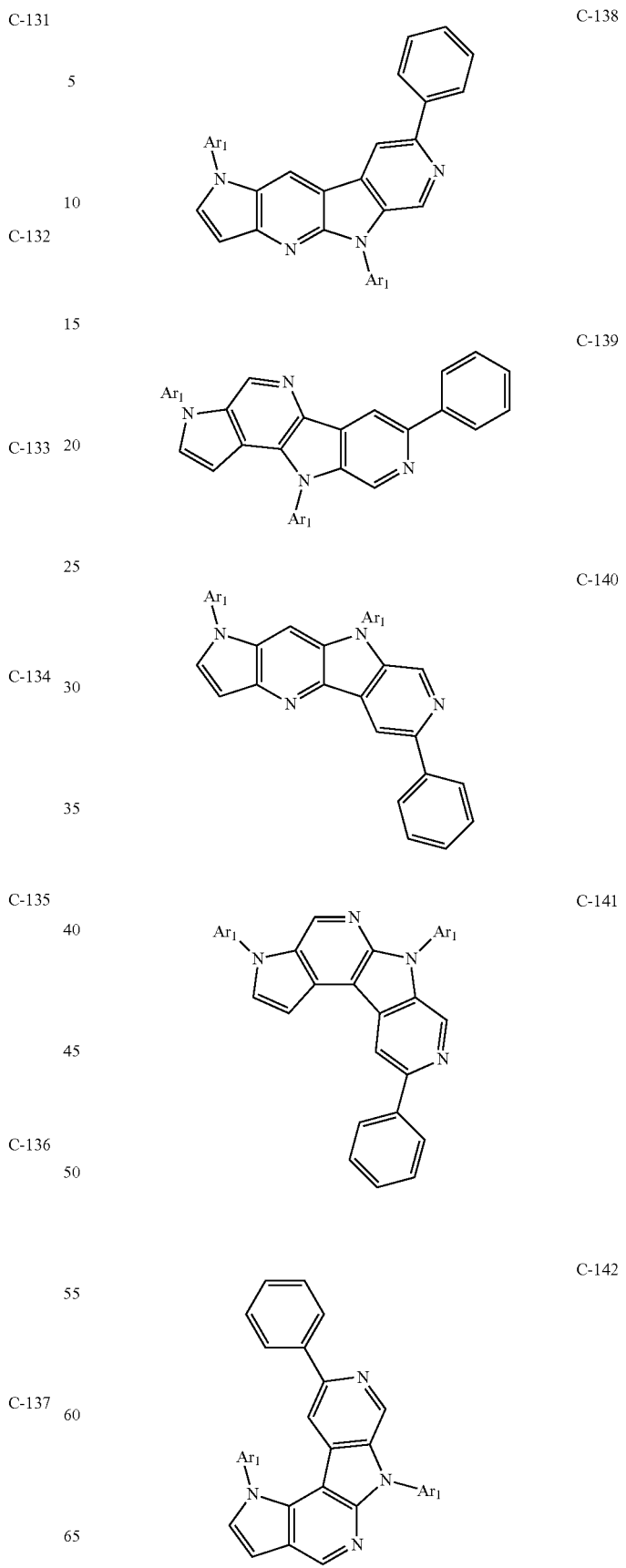

C-143
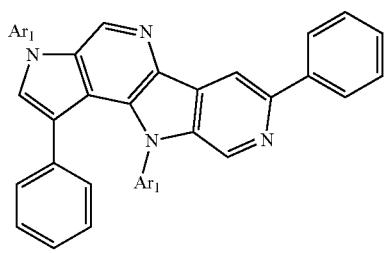
C-144
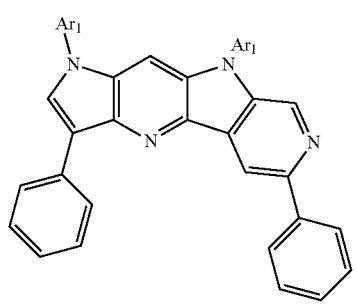
C-145
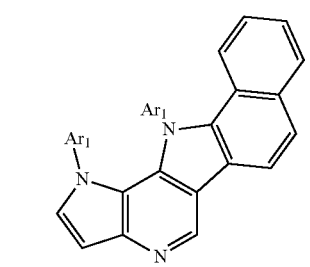
C-146
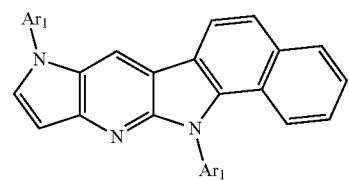
C-147
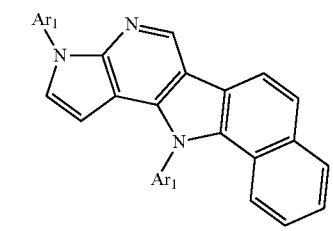
C=148
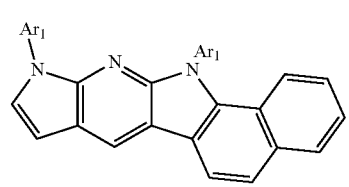
C-149
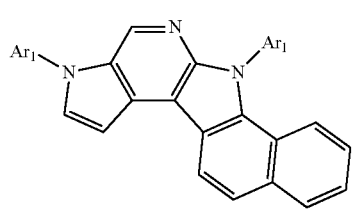
C-150
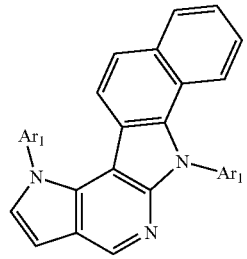
C-151
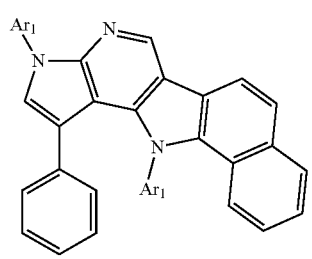
C-152
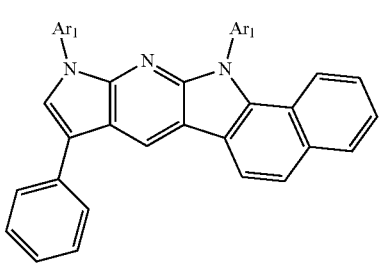
C-153
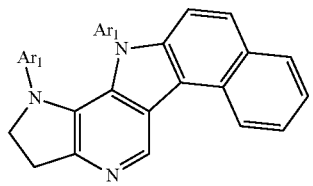
C-154
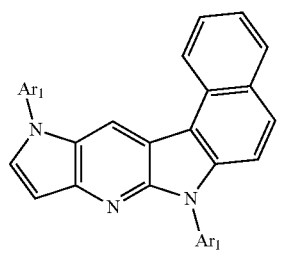
C-155
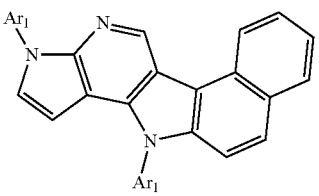

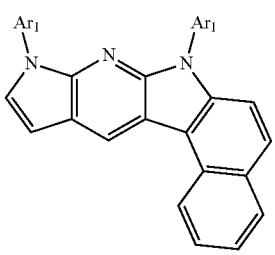
C-156
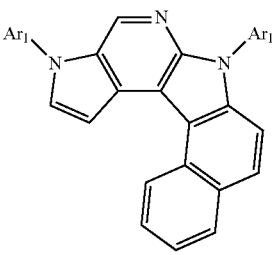
C-157
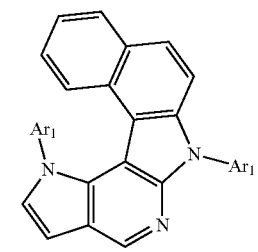
C-158
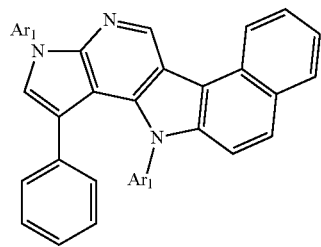
C-159
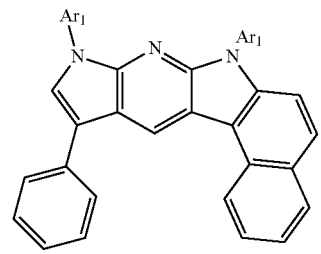
C-160
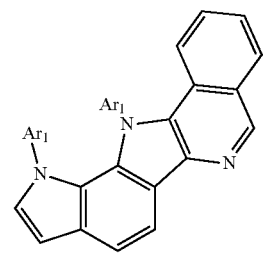
C-161
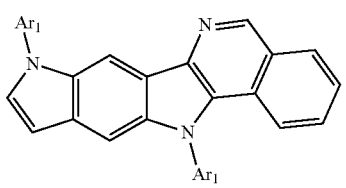
C-162
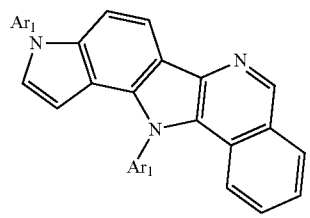
C-163
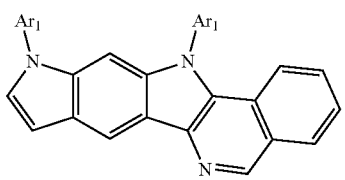
C-164
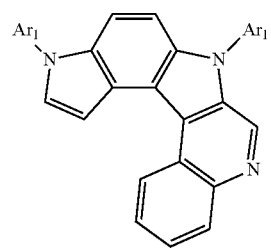
C-165
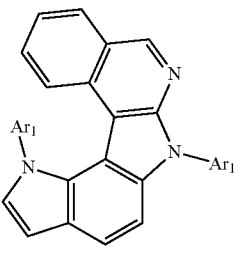
C-166
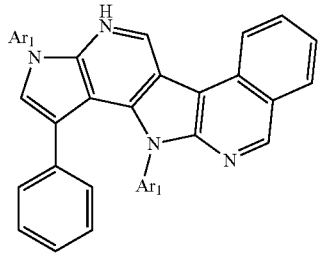
C-167
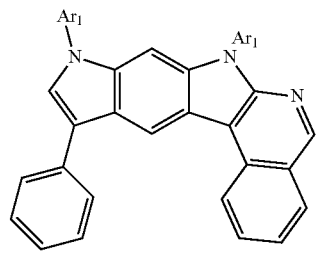
C-168

C-169 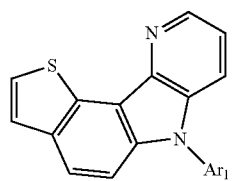
C-170 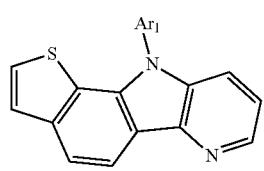
C-171 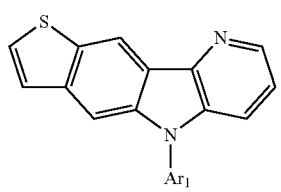
C-172 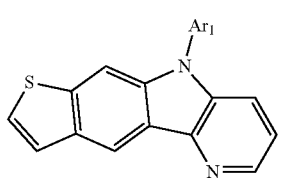
C-173 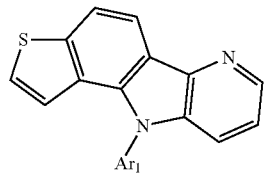
C-174 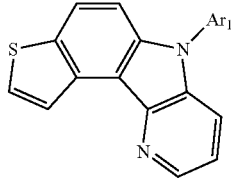
C-175 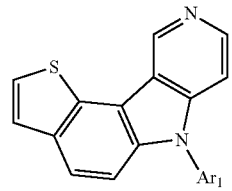
C-176 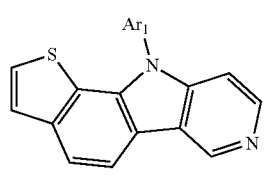
C-177 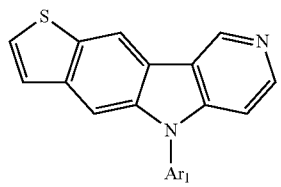
C-178 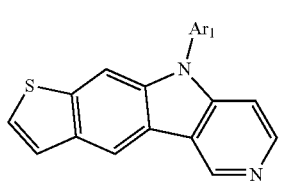
C-179 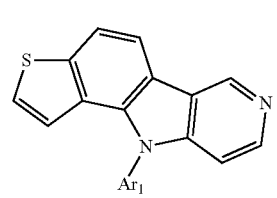
C-180 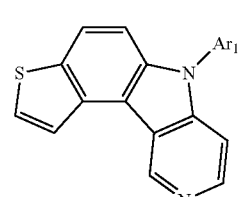
C-181 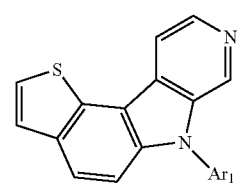
C-182 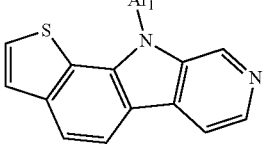
C-183 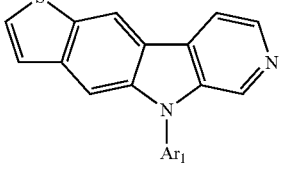
C-184 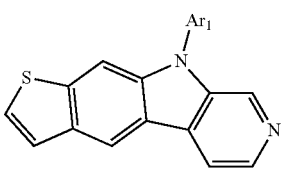

C-185 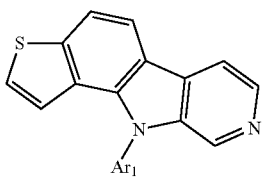
C-186 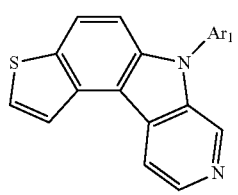
C-187 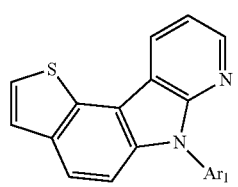
C-188 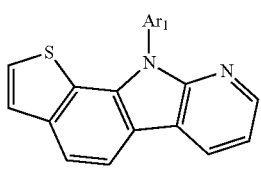
C-189 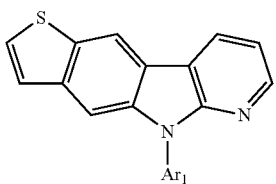
C-190 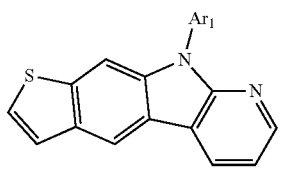
C-191 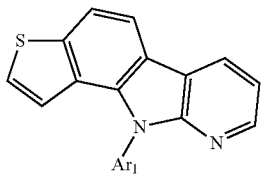
C-192 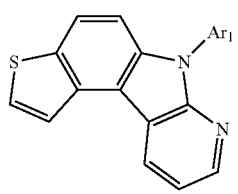
C-193 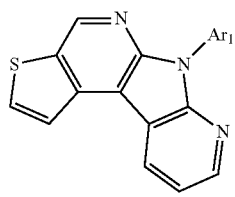
C-194 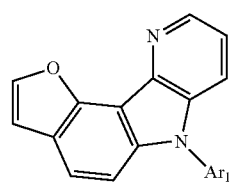
C-195 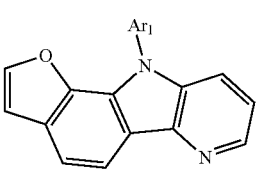
C-196 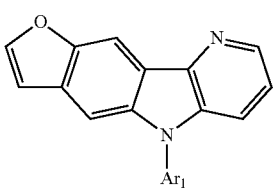
C-197 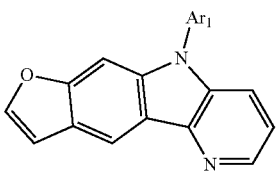
C-198 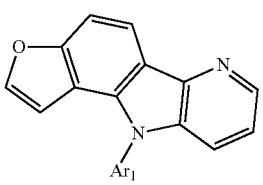
C-199 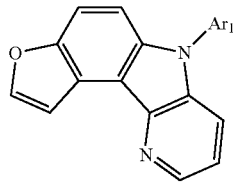
C-200 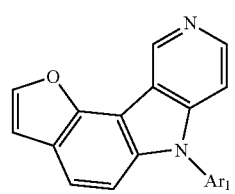

C-201 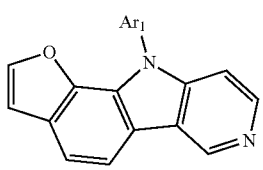
C-202 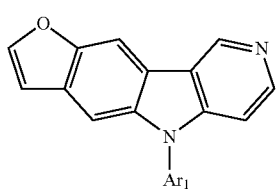
C-203 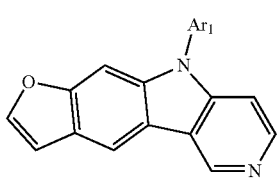
C-204 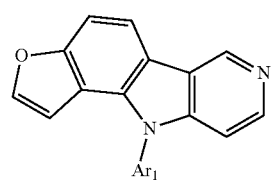
C-205 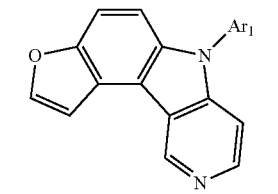
C-206 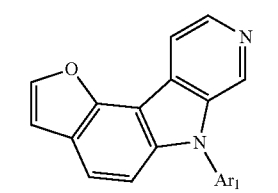
C-207 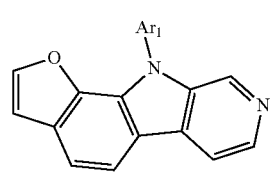
C-208 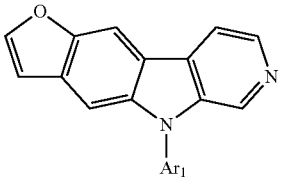
C-209 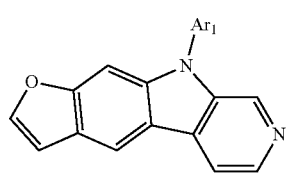
C-210 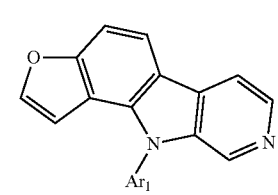
C-211 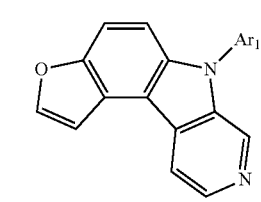
C-212 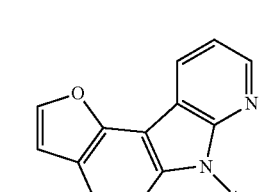
C-213 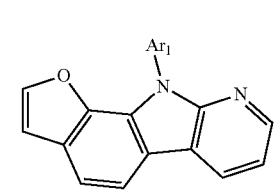
C-214 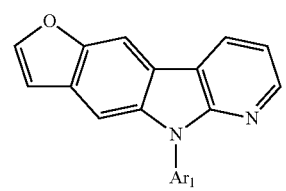
C-215 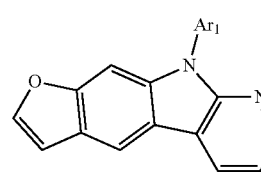
C-216 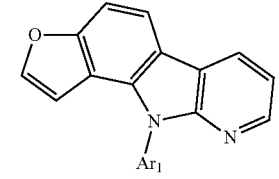

| | |
|---|---|
| 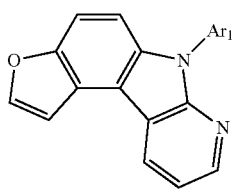 C-217 | 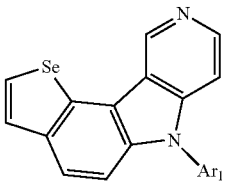 C-225 |
| 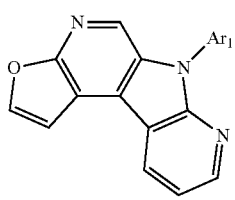 C-218 | 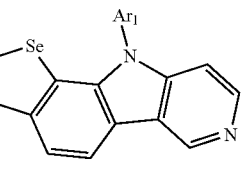 C-226 |
| 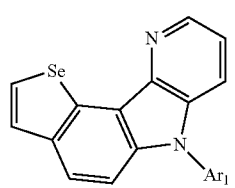 C-219 | 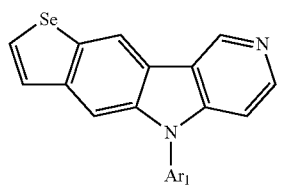 C-227 |
| 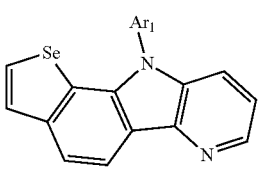 C-220 | 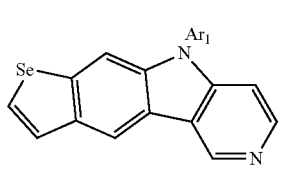 C-228 |
| 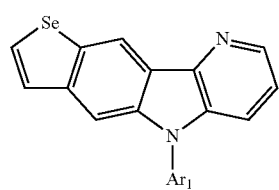 C-221 | 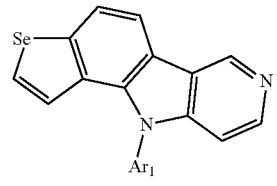 C-229 |
| 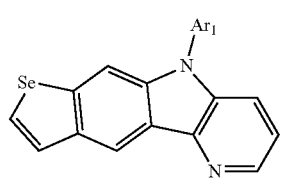 C-222 | 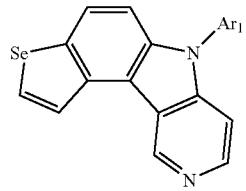 C-230 |
| 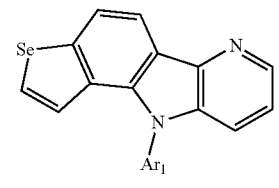 C-223 | 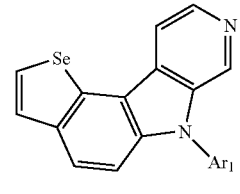 C-231 |
| 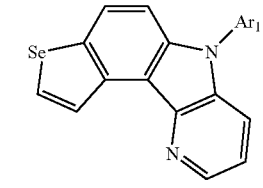 C-224 | 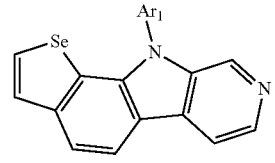 C-232 |

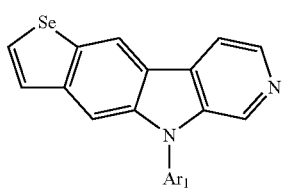 C-233
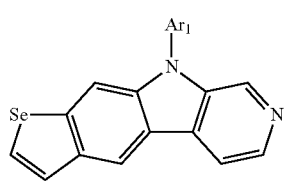 C-234
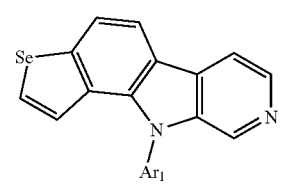 C-235
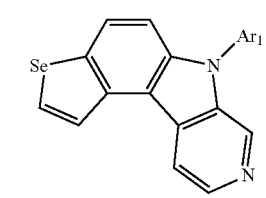 C-236
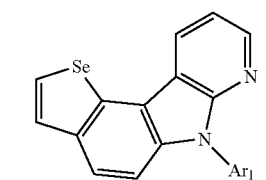 C-237
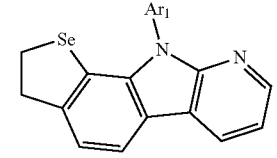 C-238
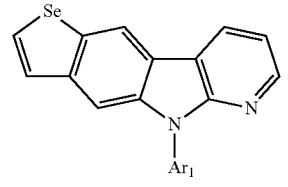 C-239
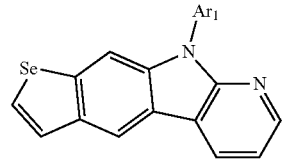 C-240
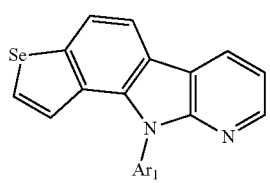 C-241
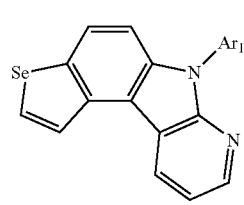 C-242
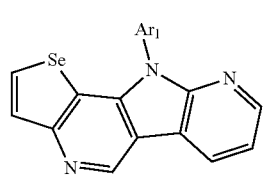 C-243
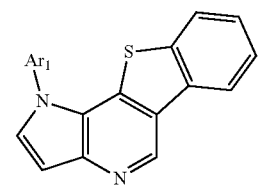 C-244
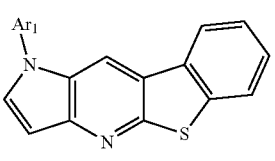 C-245
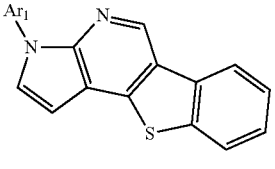 C-246
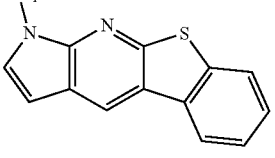 C-247
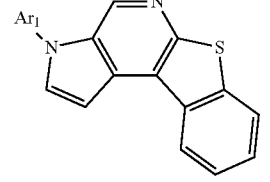 C-248

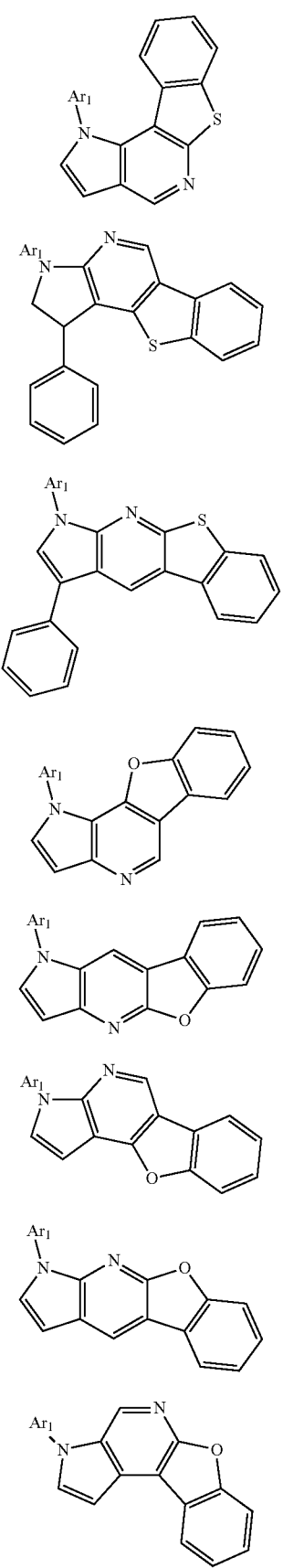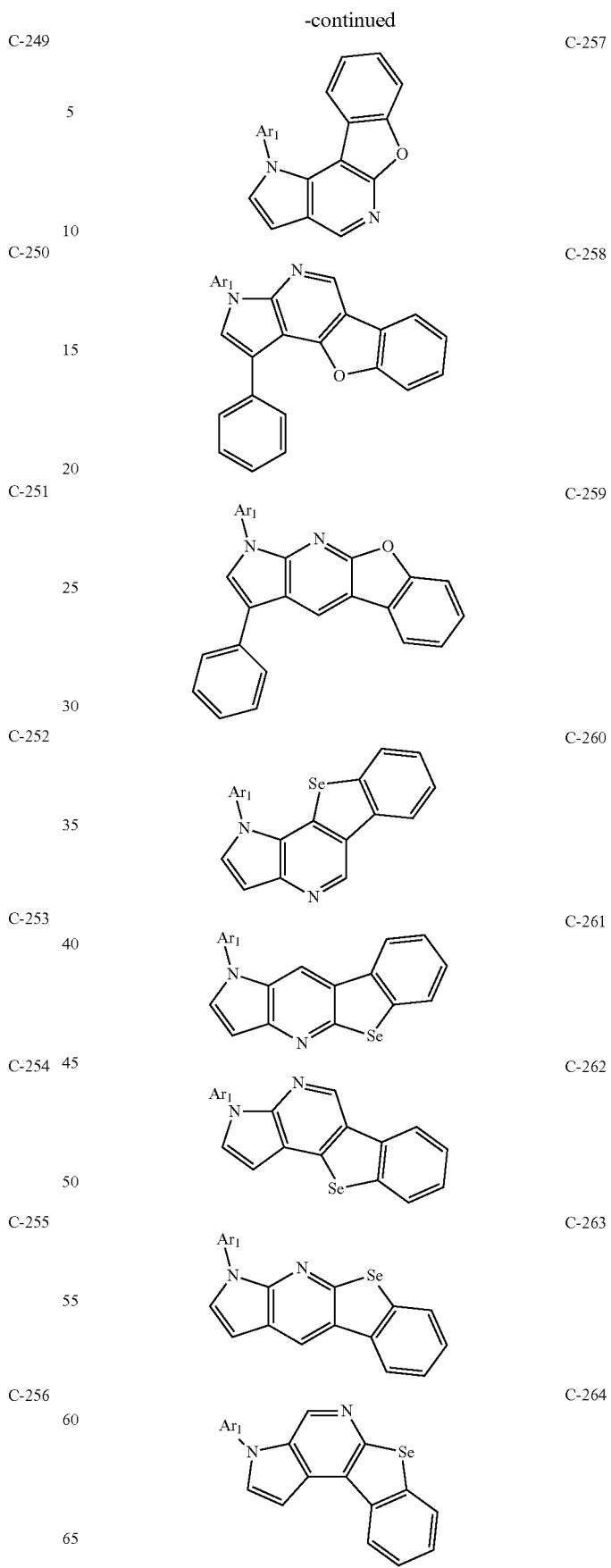

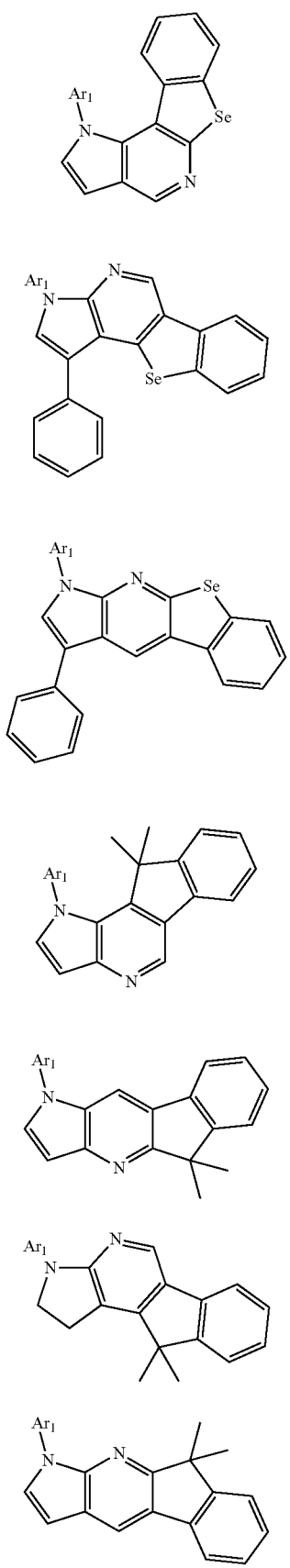

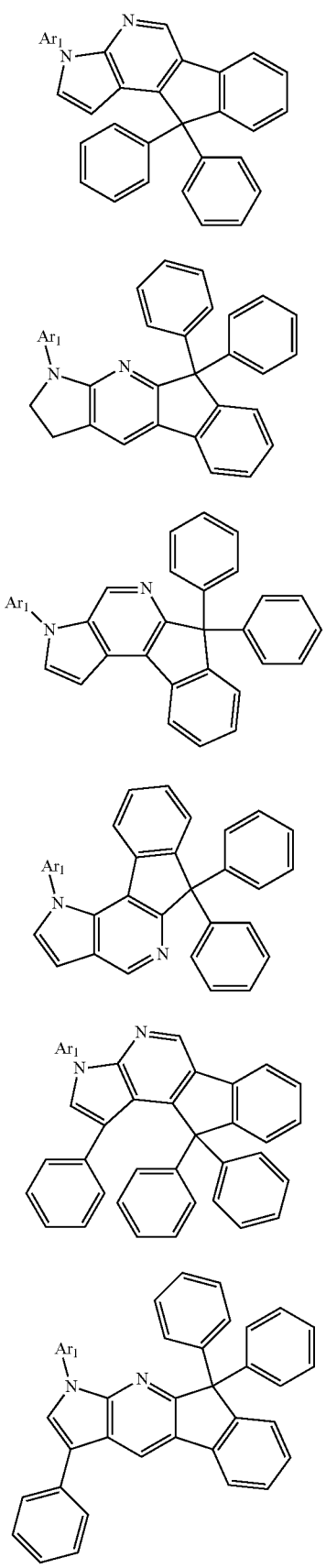
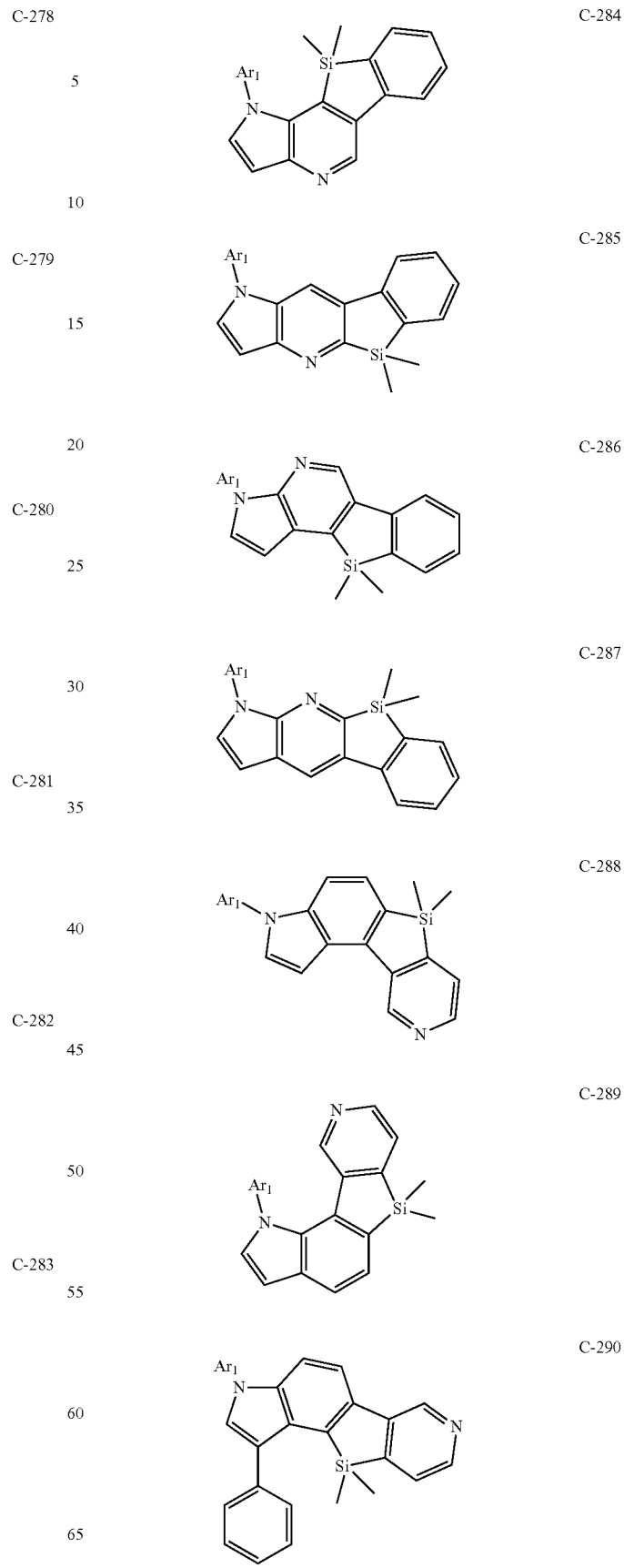

C-291
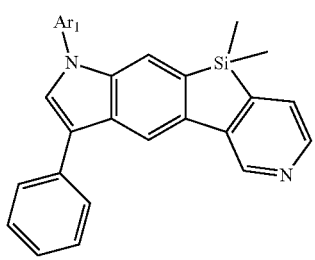
In Formulae C1 to C291 exemplified above, Ar₁'s may be the same as or different from each other even though being identically denoted, and are the same as those of Formula 1 previously defined. In this case, it is preferred that Ar₁ is selected from the group of the following substituents.
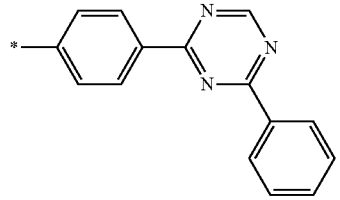
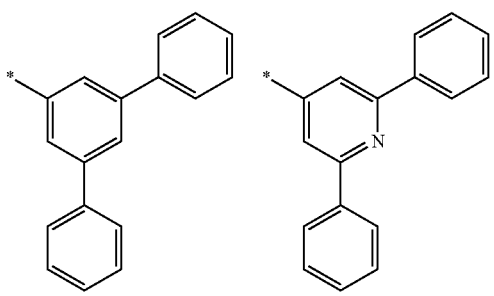
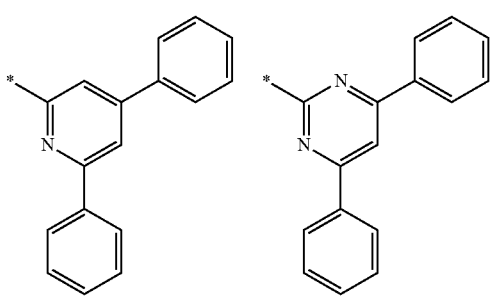
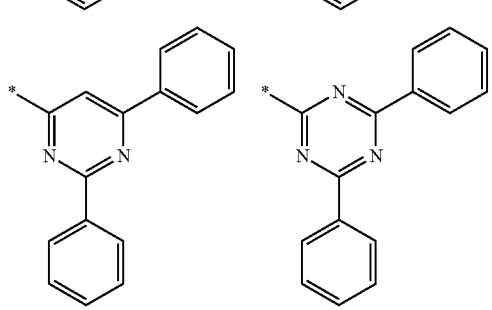
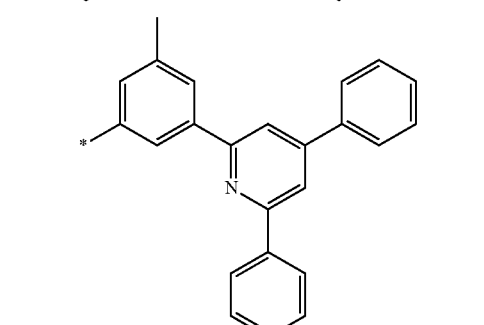
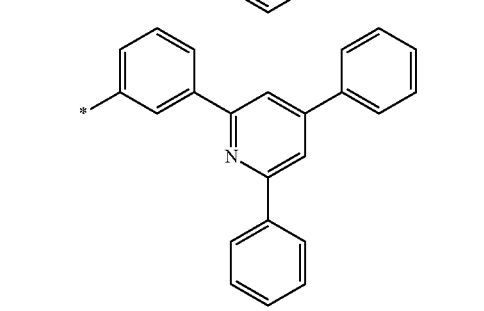

77
-continued
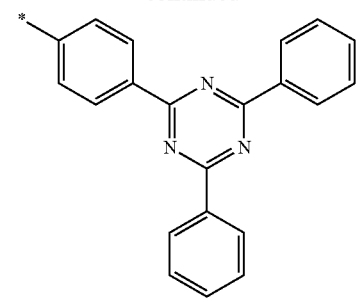
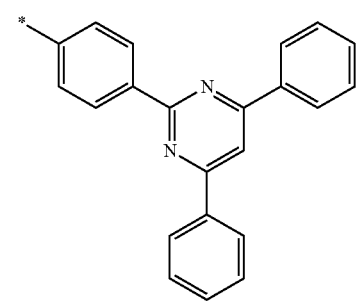
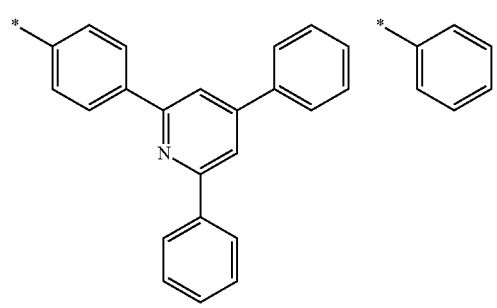
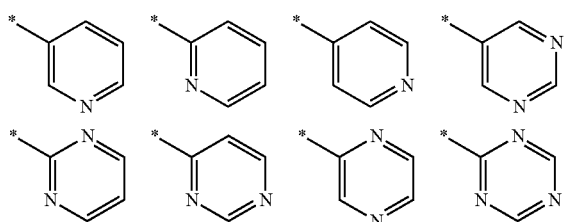
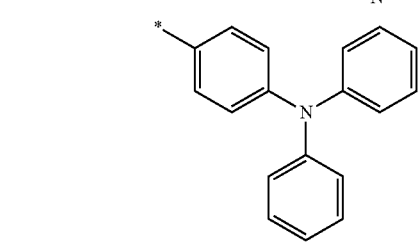
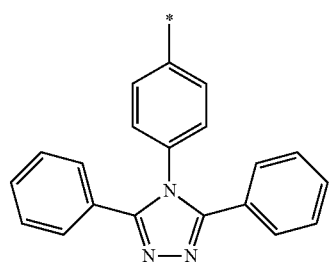
78
-continued
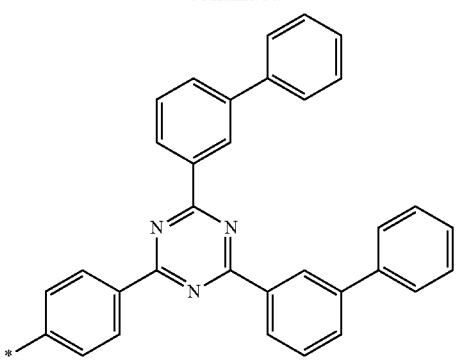
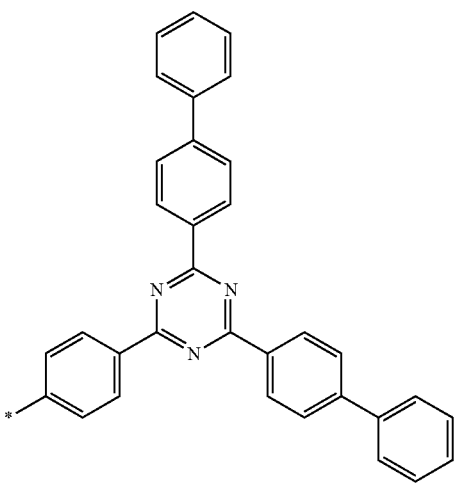
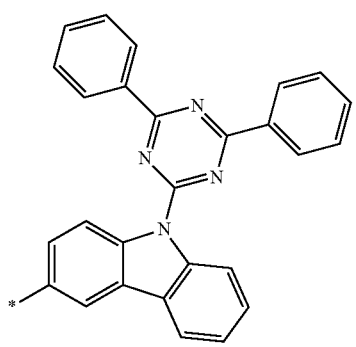
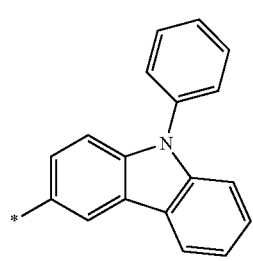

-continued
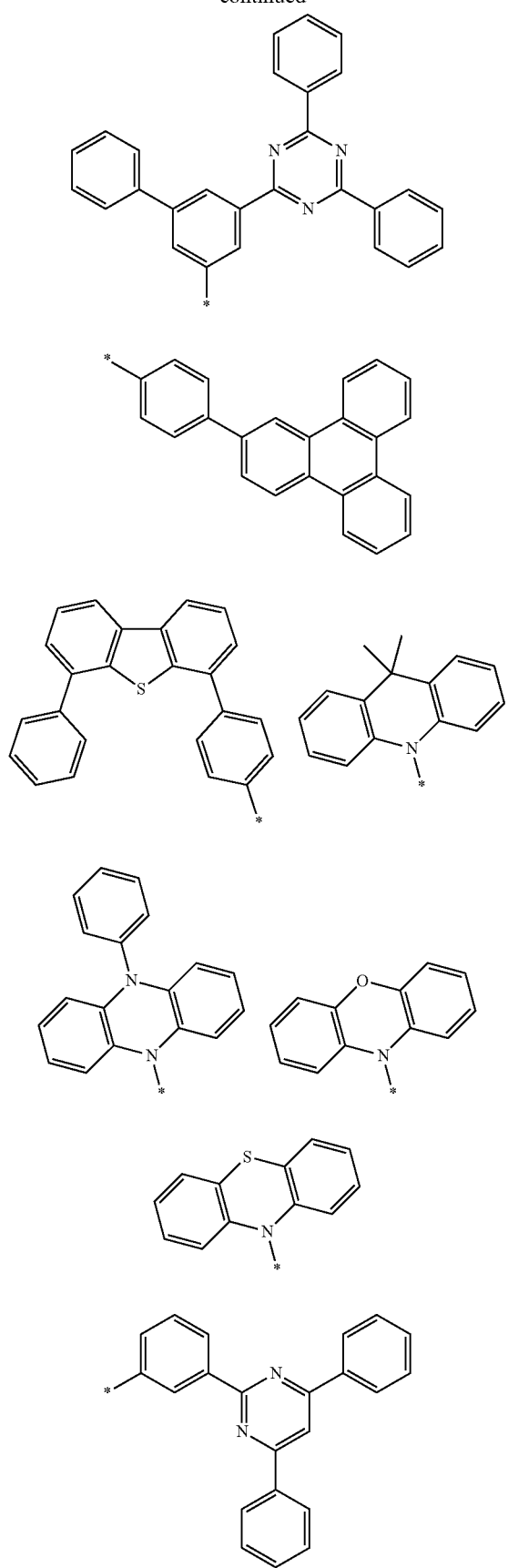
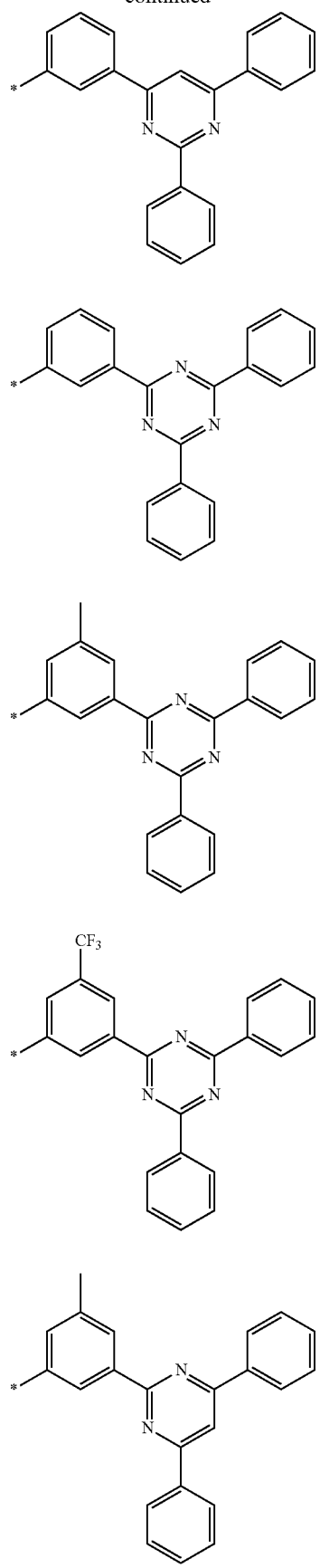

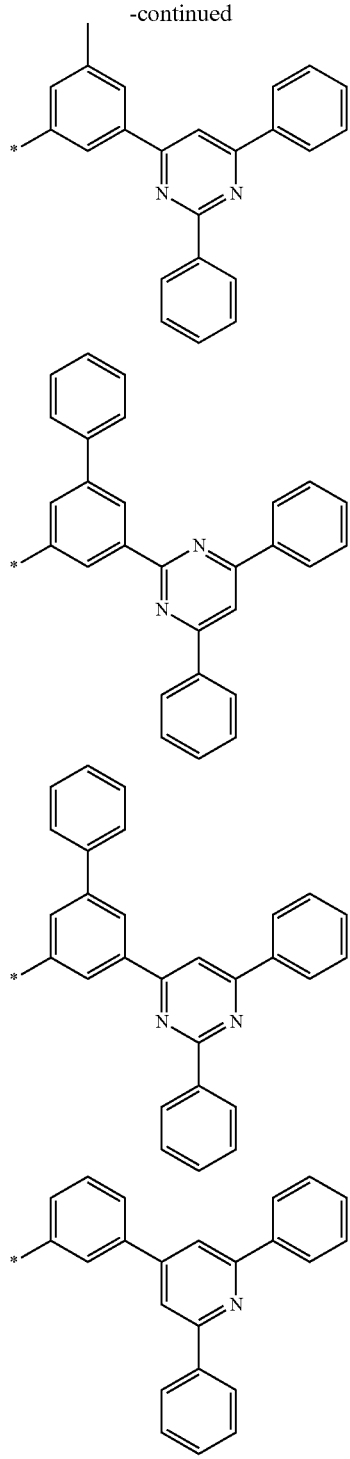

The compound represented by Formula 1 according to the present disclosure may be synthesized according to a general synthesis method. The detailed synthesis process on the compound of the present disclosure will be specifically described in the Synthesis Examples to be described below.

<Organic Electroluminescent Device>

Meanwhile, another aspect of the present disclosure relates to an organic electroluminescent device including the aforementioned compound represented by Formula 1 according to the present disclosure.

Specifically, the organic electroluminescent device according to the present disclosure includes (i) an anode, (ii) a cathode, and (iii) an organic material layer including one or more layers interposed between the anode and the cathode, in which at least one of the organic material layer includes one or more of the compounds represented by Formula 1.

Here, the organic material layer including the compound represented by Formula 1 according to the present disclosure may be one or more of a hole injection layer, a hole transporting layer, a light-emitting layer, an electron transporting layer, and an electron injection layer. Specifically, the organic material layer is preferably a hole transporting layer, a light-emitting layer, or an electron transporting layer, and more preferably a light-emitting layer.

The light-emitting layer of the organic electroluminescent device according to the present disclosure may contain a host material, and in this case, as the host material, any one of the compounds represented by Formula 1 may be used. When the light-emitting layer contains any one of the compounds represented by Formula 1, it is possible to provide an organic electroluminescent device having excellent efficiency (light-emitting efficiency and power efficiency), a lifespan, brightness, driving voltage, and the like because the binding force of holes and electrons is increased in the light-emitting layer. The compound represented by Formula 1 may be included in the organic electroluminescent device as a blue, green, and/or red phosphorescent host, a fluorescent host, or a dopant material. Further, the compound may be used as a dopant material.

The structure of the organic electroluminescent device according to the present disclosure is not particularly limited, but non-limiting examples thereof include a structure in which a substrate, an anode, a hole injection layer, a hole transporting layer, a light-emitting layer, an electron transporting layer, and a cathode are sequentially laminated. In this case, one or more of a hole injection layer, a hole transporting layer, and a light-emitting layer may include one or more of the compounds represented by Formula 1. In addition, the compound of the present disclosure may be used as a phosphorescent host or fluorescent host of a light-emitting layer. An electron injection layer may also be disposed on the electron transporting layer.

Furthermore, the organic EL device according to the present disclosure, as described above may have a structure in which an anode, an organic material layer including one or more layers, and a cathode are sequentially laminated, and further, an insulating layer or an adhesive layer may be inserted at the interface between an electrode and an organic material layer.

In the organic EL device according to the present disclosure, an organic material layer including the compound represented by Formula 1 may be formed by a vacuum deposition method or a solution application method. Examples of the solution application method include spin coating, dip coating, doctor blading, inkjet printing, or a thermal transfer method, but are not limited thereto.

The organic EL device according to the present disclosure may be manufactured by forming an organic material layer and an electrode using materials and methods known in the art, except that one or more layers in the organic material layer are formed so as to include the compound represented by Formula 1 according to the present disclosure.

For example, as the substrate, a silicon wafer, a quartz or glass plate, a metal plate, a plastic film or sheet, and the like may be used.

Examples of an anode material include a metal, such as vanadium, chromium, copper, zinc, and gold, or alloys thereof; a metal oxide, such as zinc oxide, indium oxide, indium tin oxide (ITO), and indium zinc oxide (IZO); a combination of metal and oxide, such as ZnO:Al or $SnO_2$:Sb; a conductive polymer, such as polythiophene, poly(3-methylthiophene), poly[3,4-(ethylene-1,2-dioxy)thiophene] (PEDT), polypyrrole, and polyaniline; or carbon black, and the like, but are not limited thereto.

Examples of a cathode material include a metal, such as magnesium, calcium, sodium, potassium, titanium, indium, yttrium, lithium, gadolinium, aluminum, silver, tin, or lead, or alloys thereof; a multi-layer structured material, such as LiF/Al or $LiO_2$/Al, and the like, but are not limited thereto.

Furthermore, the hole injection layer, the hole transporting layer, the electron injection layer, and the electron transporting layer are not particularly limited, and typical materials known in the art may be used.

Hereinafter, the present disclosure will be described in detail as follows through the Examples. However, the following Examples are only for exemplifying the present disclosure, and the present disclosure is not limited by the following Examples.

PREPARATION EXAMPLE 1

Synthesis of IC-1

<Step 1> Synthesis of 6-(4,4,5,5-tetramethyl-1,3,2-dioxaborolan-2-yl)-1H-indole

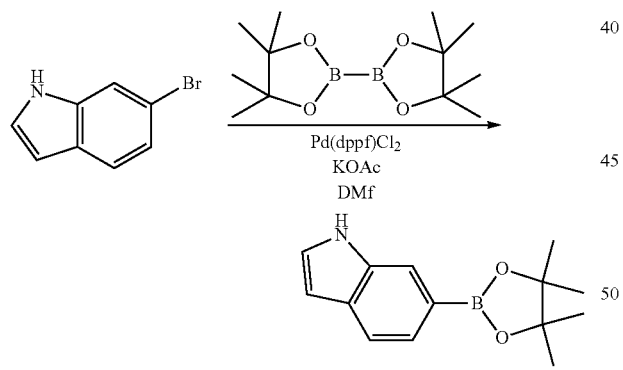

6-bromo-1H-indole (25 g, 0.128 mol), 4,4,4',4',5,5,5',5'-octamethyl-2,2'-bi(1,3,2-dioxaborolane) (48.58 g, 0.191 mol), Pd(dppf)Cl$_2$ (5.2 g, 5 mol %), KOAc (37.55 g, 0.383 mol), and DMF (500 ml) were mixed under nitrogen flow, and the resulting mixture was stirred at 130° C. for 12 hours. After the reaction was terminated, 6-(4,4,5,5-tetramethyl-1,3,2-dioxaborolan-2-yl)-1H-indole (20.15 g, yield 65%) was obtained by performing extraction with ethyl acetate, removing moisture over MgSO$_4$, and purifying the residue with column chromatography (Hexane:EA=10:1 (v/v)).

$^1$H-NMR: δ 1.25 (s, 12H), 6.47 (d, 1H), 7.28 (d, 1H), 7.43 (d, 1H), 7.54 (d, 1H), 7.99 (s, 1H), 8.25 (s, 1H)

<Step 2> Synthesis of 6-(3-nitropyridin-2-yl)-1H-indole

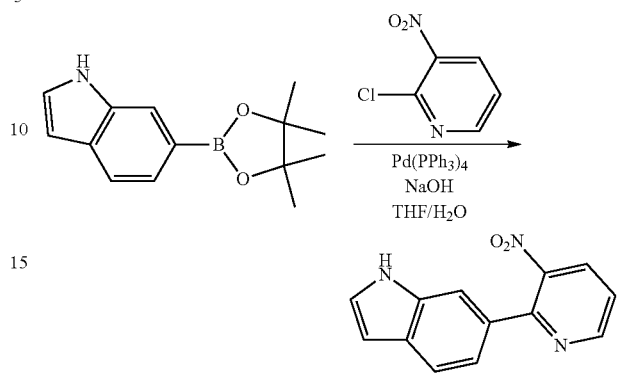

2-chloro-3-nitropyridine (10.95 g, 69.07 mmol), the 6-(4,4,5,5-tetramethyl-1,3,2-dioxaborolan-2-yl)-1H-indole (20.15 g, 82.88 mmol) obtained in <Step 1>, NaOH (8.29 g, 207.21 mmol), and THF/H$_2$O (300 ml/150 ml) were mixed under nitrogen flow, Pd(PPh$_3$)$_4$ (3.99 g, 5 mol %) was added thereto at 40° C., and the resulting mixture was stirred at 80° C. for 12 hours.

After the reaction was terminated, extraction was performed with methylene chloride, MgSO$_4$ was added thereto, and the resulting product was filtered. 6-(3-nitropyridin-2-yl)-1H-indole (11.90 g, yield 72%) was obtained by removing the solvent from the obtained organic layer, and then purifying the residue with column chromatography (Hexane:EA=10:1 (v/v)).

$^1$H-NMR: δ 6.45 (d, 1H), 7.26 (m, 2H), 7.44 (d, 1H), 7.56 (d, 1H), 7.98 (s, 1H), 8.24 (s, 1H), 8.32 (d, 1H), 8.89 (d, 1H)

<Step 3> Synthesis of 1-(biphenyl-3-yl)-6-(3-nitropyridin-2-yl)-1H-indole

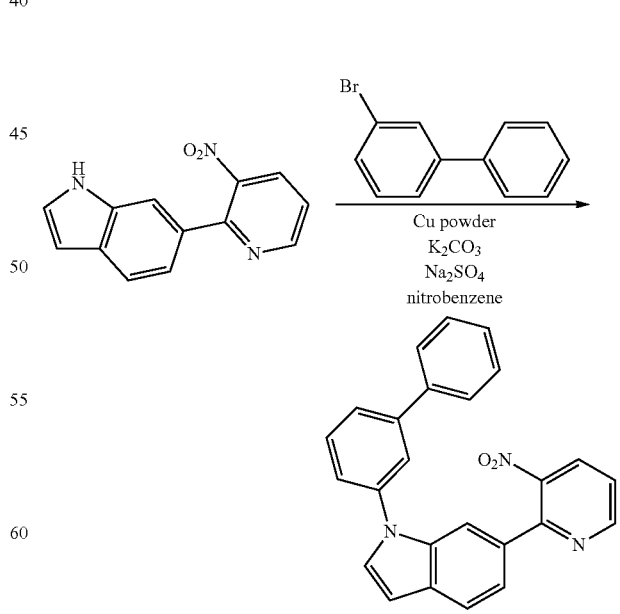

The 6-(3-nitropyridin-2-yl)-1H-indole (11.90 g, 49.74 mmol) obtained in <Step 2>, 3-bromobiphenyl (17.39 g, 74.61 mmol), Cu powder (0.32 g, 4.97 mmol), K$_2$CO$_3$ (6.87 g, 49.74 mmol), Na$_2$SO$_4$ (7.07 g, 49.74 mmol), and nitrobenzene (200 ml) were mixed under nitrogen flow, and the resulting mixture was stirred at 190° C. for 12 hours.

After the reaction was terminated, nitrobenzene was removed, the organic layer was separated by methylene chloride, and water was removed by using MgSO$_4$. 1-(biphenyl-3-yl)-6-(3-nitropyridin-2-yl)-1H-indole (10.51 g, yield 54%) was obtained by removing the solvent from the organic layer from which water had been removed, and then purifying the residue with column chromatography (Hexane:MC=1:1 (v/v)).

$^1$H-NMR: δ 6.45 (d, 1H), 7.26 (m, 2H), 7.44 (m, 5H), 7.52 (m, 4H), 7.57 (d, 1H), 7.98 (s, 1H), 8.05 (s, 1H), 8.32 (d, 1H), 8.89 (d, 1H)

<Step 4> Synthesis of IC-1

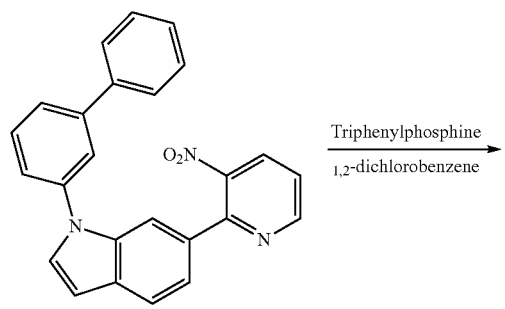

The 1-(biphenyl-3-yl)-6-(3-nitropyridin-2-yl)-1H-indole (10.51 g, 26.85 mmol) obtained in <Step 3>, triphenylphosphine (17.61 g, 67.13 mmol), and 1,2-dichlorobenzene (200 ml) were mixed under nitrogen flow, and the resulting mixture was stirred for 12 hours.

After the reaction was terminated, 1,2-dichlorobenzene was removed, and extraction was performed with dichloromethane. IC-1 (3.67 g, yield 38%) was obtained by removing water from the obtained organic layer over MgSO$_4$, and purifying the residue with column chromatography (Hexane:EA=3:1 (v/v)).

$^1$H-NMR: δ 6.46 (d, 1H), 7.25 (m, 2H), 7.45 (m, 5H), 7.53 (m, 4H), 7.59 (d, 1H), 7.88 (s, 1H), 8.27 (s, 1H), 8.33 (d, 1H), 8.87 (d, 1H)

PREPARATION EXAMPLE 2

Synthesis of IC-2

<Step 1> Synthesis of 5-(4,4,5,5-tetramethyl-1,3,2-dioxaborolan-2-yl)-1H-indol

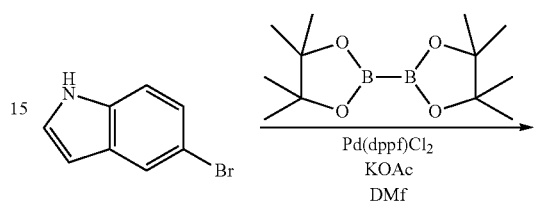

5-(4,4,5,5-Tetramethyl-1,3,2-dioxaborolan-2-yl)-1H-indole was obtained by performing the same procedure as in <Step 1> of Preparation Example 1, except that 5-bromo-1H-indole was used instead of 6-bromo-1H-indole.

$^1$H-NMR: δ 1.25 (s, 12H), 6.46 (d, 1H), 7.25 (d, 1H), 7.43 (d, 1H), 7.54 (d, 1H), 7.97 (s, 1H), 8.23 (s, 1H)

<Step 2> Synthesis of 5-(3-nitropyridin-2-yl)-1H-indole

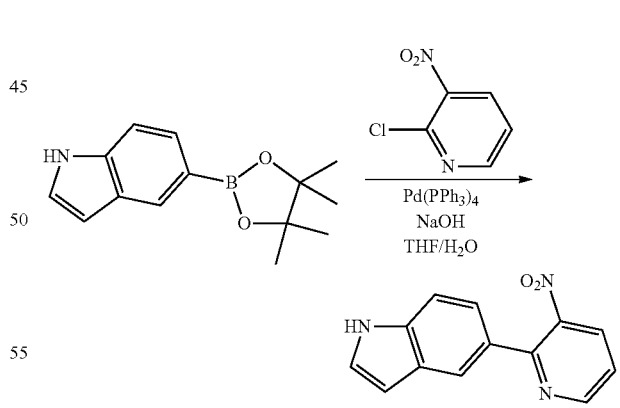

5-(3-nitropyridin-2-yl)-1H-indole was obtained by performing the same procedure as in <Step 2> of Preparation Example 1, except that the 5-(4,4,5,5-tetramethyl-1,3,2-dioxaborolan-2-yl)-1H-indole obtained in <Step 1> was used instead of 6(4,4,5,5-tetramethyl-1,3,2-dioxaborolan-2-yl)-1H-indole.

$^1$H-NMR: δ 6.45 (d, 1H), 7.24 (m, 2H), 7.42 (d, 1H), 7.53 (d, 1H), 7.96 (s, 1H), 8.22 (s, 1H), 8.31 (d, 1H), 8.88 (d, 1H)

<Step 3> Synthesis of 5-(3-nitropyridin-2-yl)-1-phenyl-1H-indole

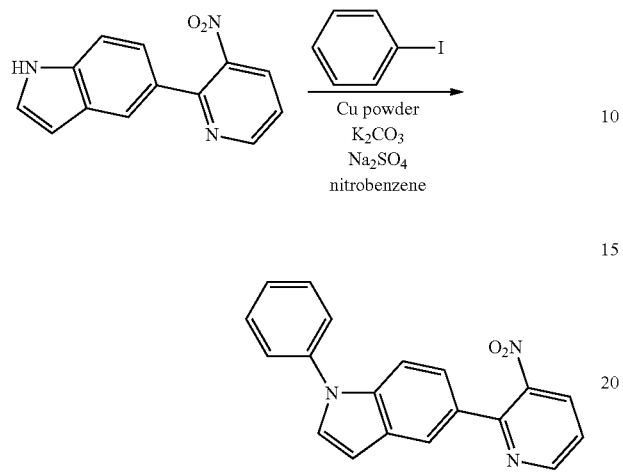

5-(3-nitropyridin-2-yl)-1-phenyl-1H-indole was obtained by performing the same procedure as in <Step 3> of Preparation Example 1, except that the 5-(3-nitropyridin-2-yl)-1H-indole obtained in <Step 2> and iodobenzene were used instead of 6-(3-nitropyridin-2-yl)-1H-indole and 3-bromobiphenyl.

$^1$H-NMR: δ 6.44 (d, 1H), 7.23 (m, 2H), 7.41 (m, 3H), 7.51 (m, 4H), 7.95 (s, 1H), 8.33 (d, 1H), 8.86 (d, 1H)

<Step 4> Synthesis of IC-2

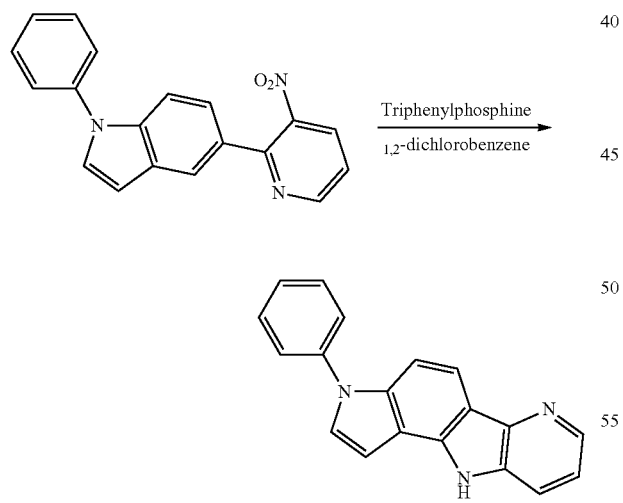

IC-2 was obtained by performing the same procedure as in <Step 4> of Preparation Example 1, except that the 5-(3-nitropyridin-2-yl)-1-phenyl-1H-indole obtained in <Step 3> was used instead of 1-(biphenyl-3-yl)-6-(3-nitropyridin-2-yl)-1H-indole.

$^1$H-NMR: δ 6.44 (d, 1H), 7.23 (m, 2H), 7.45 (m, 3H), 7.53 (m, 4H), 8.25 (s, 1H), 8.33 (d, 1H), 8.86 (d, 1H)

PREPARATION EXAMPLE 3

Synthesis of IC-3

<Step 1> Synthesis of 1-(naphthalen-2-yl)-5-(3-nitropyridin-2-yl)-1H-indole

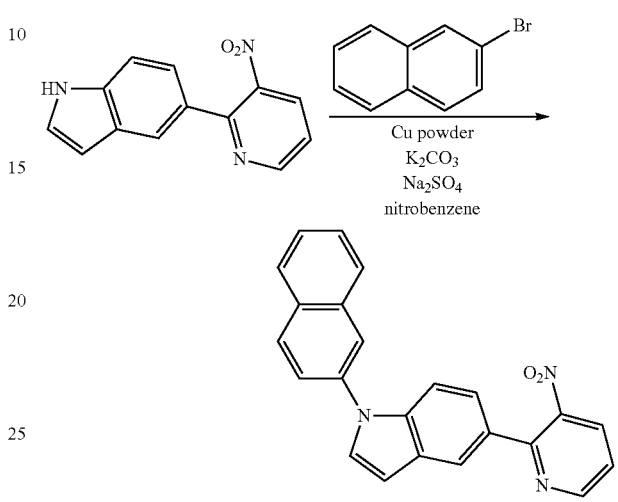

1-(naphthalen-2-yl)-5-(3-nitropyridin-2-yl)-1H-indole was obtained by performing the same procedure as in <Step 3> of Preparation Example 1, except that the 5-(3-nitropyridin-2-yl)-1H-indole obtained in <Step 3> of Preparation Example 2 and 2-bromonaphthalene were used instead of 6-(3-nitropyridin-2-yl)-1H-indole and 3-bromobiphenyl.

$^1$H-NMR: δ 6.44 (d, 1H), 7.23 (m, 2H), 7.36 (d, 1H), 7.41 (d, 1H), 7.55 (m, 3H), 7.82 (s, 1H), 7.98 (m, 4H), 8.33 (d, 1H), 8.86 (d, 1H)

<Step 2> Synthesis of IC-3

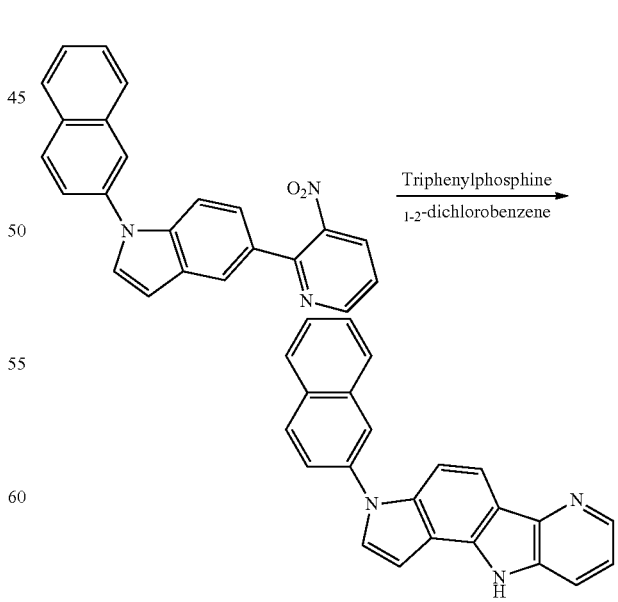

IC-3 was obtained by performing the same procedure as in <Step 4> of Preparation Example 1, except that the 1-(naphthalen-2-yl)-5-(3-nitropyridin-2-yl)-1H-indole obtained in <Step 1> was used instead of 1-(biphenyl-3-yl)-6-(3-nitropyridin-2-yl)-1H-indole.

¹H-NMR: δ 6.44 (d, 1H), 7.23 (m, 2H), 7.36 (d, 1H), 7.41 (d, 1H), 7.55 (m, 3H), 7.82 (s, 1H), 7.98 (m, 3H), 8.23 (s, 1H), 8.33 (d, 1H), 8.86 (d, 1H)

PREPARATION EXAMPLE 4

Synthesis of IC-4

<Step 1> Synthesis of 5-chloro-3-phenyl-1H-indole

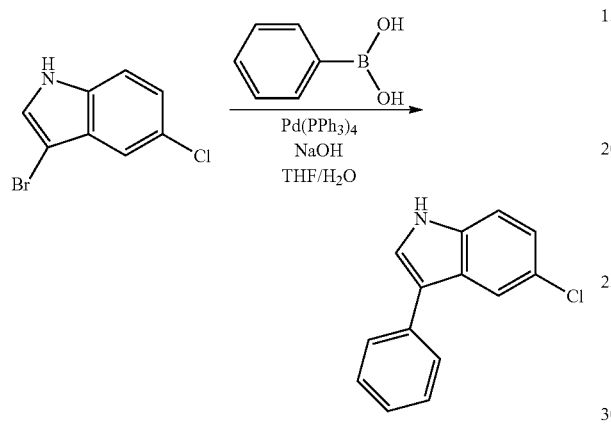

5-chloro-3-phenyl-1H-indole was obtained by performing the same procedure as in <Step 2> of Preparation Example 1, except that 3-bromo-5-chloro-1H-indole and phenylboronic acid were used instead of 2-chloro-3-nitropyridine and 6-(4,4,5,5-tetramethyl-1,3,2-dioxaborolan-2-yl)-1H-indole.

¹H-NMR: δ 7.18 (d, 1H), 7.25 (d, 1H), 7.45 (m, 3H), 7.55 (m, 2H), 7.68 (s, 1H), 8.24 (s, 1H), 8.31 (s, 1H)

<Step 2> Synthesis of 3-phenyl-5-(4,4,5,5-tetramethyl-1,3,2-dioxaborolan-2-yl)-1H-indole

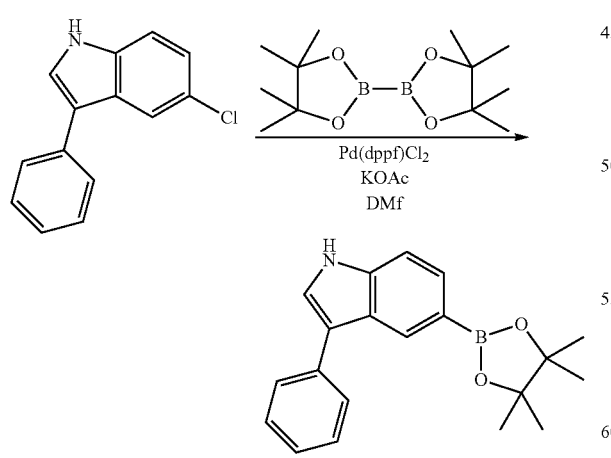

3-phenyl-5-(4,4,5,5-tetramethyl-1,3,2-dioxaborolan-2-yl)-1H-indole was obtained by performing the same procedure as in <Step 1> of Preparation Example 1, except that the 5-chloro-3-phenyl-1H-indole obtained in <Step 1> was used instead of 6-bromo-1H-indole.

¹H-NMR: δ 1.24 (s, 12H), 7.15 (d, 1H), 7.24 (d, 1H), 7.43 (m, 3H), 7.54 (m, 2H), 7.67 (s, 1H), 8.23 (s, 1H), 8.30 (s, 1H)

<Step 3> Synthesis of 5-(3-nitropyridin-2-yl)-3-phenyl-1H-indole

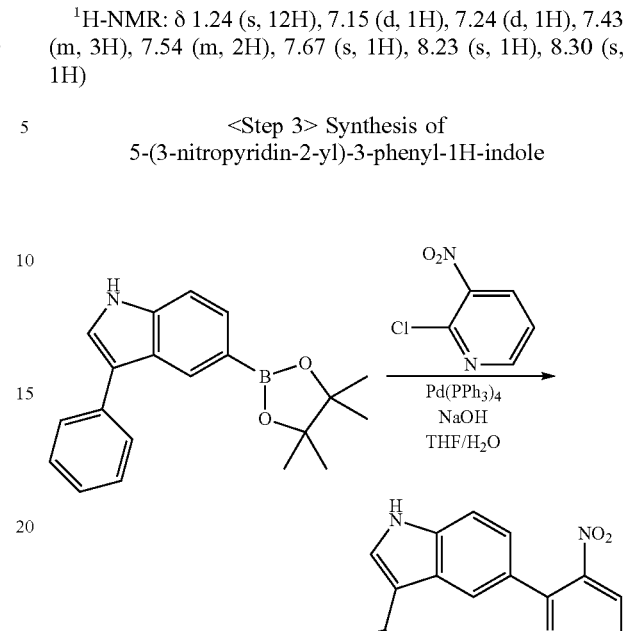

5-(3-nitropyridin-2-yl)-3-phenyl-1H-indole was obtained by performing the same procedure as in <Step 2> of Preparation Example 1, except that the 3-phenyl-5-(4,4,5,5-tetramethyl-1,3,2-dioxaborolan-2-yl)-1H-indole obtained in <Step 2> was used instead of 6-(4,4,5,5-tetramethyl-1,3,2-dioxaborolan-2-yl)-1H-indole.

¹H-NMR: δ 7.17 (d, 1H), 7.24 (m, 2H), 7.44 (m, 3H), 7.55 (m, 2H), 7.66 (s, 1H), 8.24 (s, 1H), 8.32 (m, 2H), 8.86 (d, 1H)

<Step 4> Synthesis of 5-(3-nitropyridin-2-yl)-1,3-diphenyl-1H-indole

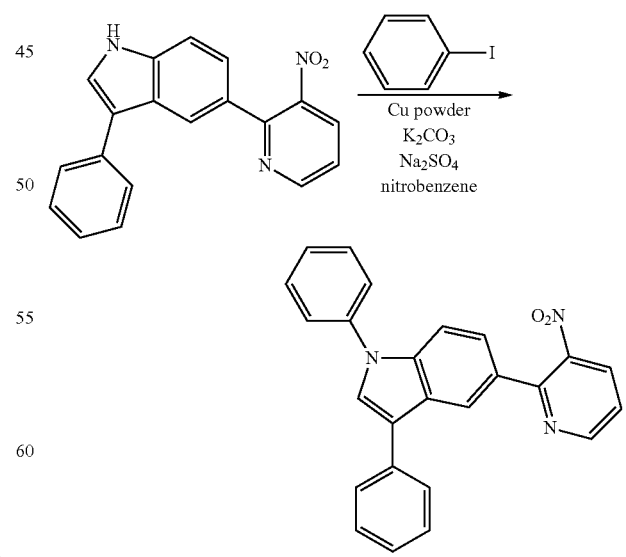

5-(3-nitropyridin-2-yl)-1,3-diphenyl-1H-indole was obtained by performing the same procedure as in <Step 3> of Preparation Example 1, except that the 5-(3-nitropyridin-2-yl)-3-phenyl-1H-indole obtained in <Step 3> and iodobenzene were used instead of 6-(3-nitropyridin-2-yl)-1H-indole and 3-bromobiphenyl.

¹H-NMR: δ 7.18 (d, 1H), 7.25 (m, 2H), 7.44 (m, 4H), 7.51 (d, 2H), 7.56 (m, 4H), 7.67 (s, 1H), 8.31 (m, 2H), 8.85 (d, 1H)

<Step 5> Synthesis of IC-4

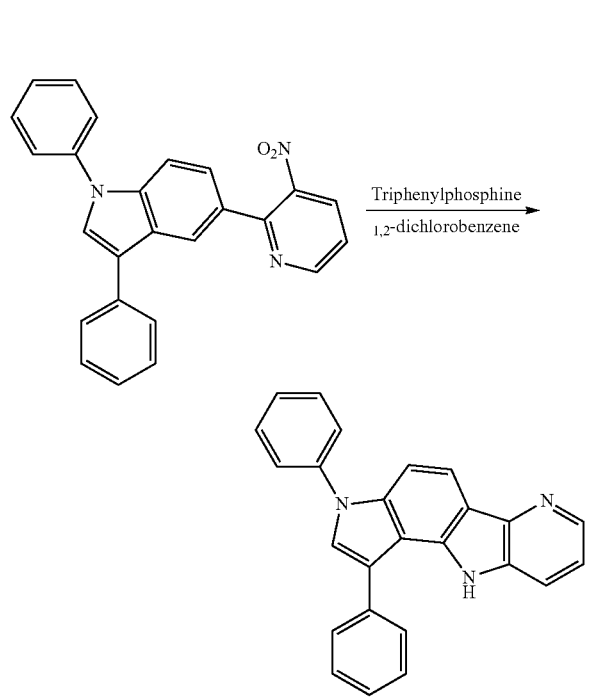

IC-4 was obtained by performing the same procedure as in <Step 4> of Preparation Example 1, except that the 5-(3-nitropyridin-2-yl)-1,3-diphenyl-1H-indole obtained in <Step 4> was used instead of 1-(biphenyl-3-yl)-6-(3-nitropyridin-2-yl)-1H-indole.

¹H-NMR: δ 7.18 (d, 1H), 7.25 (d, 1H), 7.44 (m, 4H), 7.51 (d, 2H), 7.56 (m, 4H), 7.67 (s, 1H), 8.25 (s, 1H), 8.31 (m, 2H), 8.85 (d, 1H)

PREPARATION EXAMPLE 5

Synthesis of IC-5

<Step 1> Synthesis of 7-chloro-3-phenyl-1H-indole

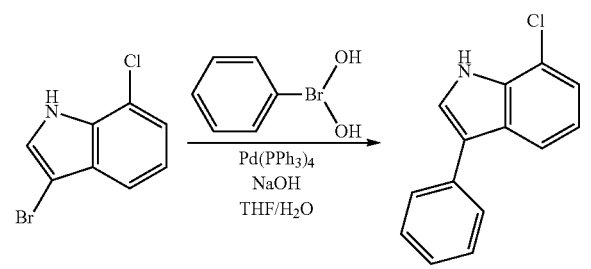

7-chloro-3-phenyl-1H-indole was obtained by performing the same procedure as in <Step 2> of Preparation Example 1, except that 3-bromo-7-chloro-1H-indole and phenylboronic acid were used instead of 2-chloro-3-nitropyridine and 6-(4,4,5,5-tetramethyl-1,3,2-dioxaborolan-2-yl)-1H-indole.

¹H-NMR: δ 7.04 (t, 1H), 7.17 (d, 1H), 7.41 (m, 1H), 7.52 (m, 4H), 7.64 (d, 1H), 8.24 (s, 1H), 8.31 (s, 1H)

<Step 2> Synthesis of 3-phenyl-7-(4,4,5,5-tetramethyl-1,3,2-dioxaborolan-2-yl)-1H-indole

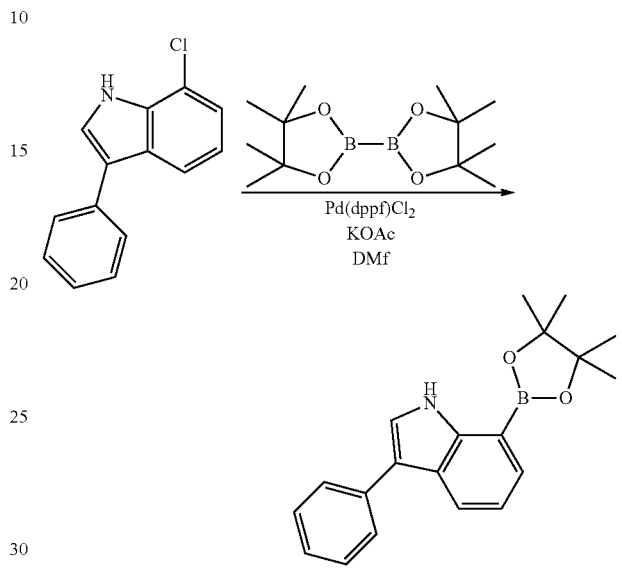

3-phenyl-7-(4,4,5,5-tetramethyl-1,3,2-dioxaborolan-2-yl)-1H-indole was obtained by performing the same procedure as in <Step 1> of Preparation Example 1, except that the 7-chloro-3-phenyl-1H-indole obtained in <Step 1> was used instead of 6-bromo-1H-indole.

¹H-NMR: δ 1.25 (s, 12H), 7.05 (t, 1H), 7.13 (d, 1H), 7.43 (m, 1H), 7.53 (m, 4H), 7.65 (d, 1H), 8.25 (s, 1H), 8.30 (s, 1H)

<Step 3> Synthesis of 7-(4-nitropyridin-3-yl)-3-phenyl-1H-indole

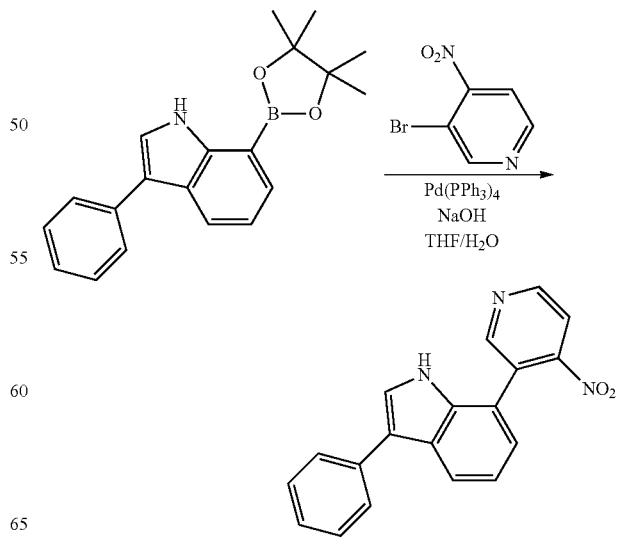

7-(4-nitropyridin-3-yl)-3-phenyl-1H-indole was obtained by performing the same procedure as in <Step 2> of Preparation Example 1, except that the 3-phenyl-7-(4,4,5,5-tetramethyl-1,3,2-dioxaborolan-2-yl)-1H-indole obtained in <Step 2> and 3-bromo-4-nitropyridine were used instead of 6-(4,4,5,5-tetramethyl-1,3,2-dioxaborolan-2-yl)-1H-indole and 2-chloro-3-nitropyridine.

¹H-NMR: δ 7.05 (t, 1H), 7.13 (d, 1H), 7.43 (m, 1H), 7.53 (m, 4H), 7.65 (d, 1H), 7.92 (d, 1H), 8.25 (s, 1H), 8.30 (m, 2H), 8.52 (s, 1H)

<Step 4> Synthesis of 1-(4,6-diphenyl-1,3,5-triazin-2-yl)-7-(4-nitropyridin-3-yl)-3-phenyl-1H-indole

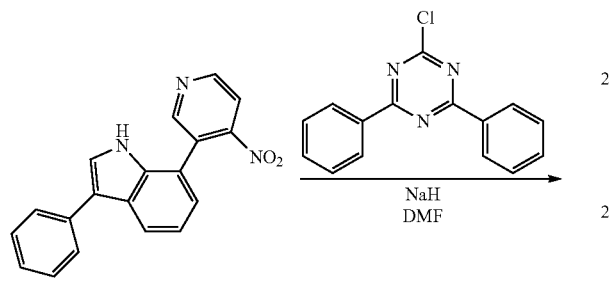

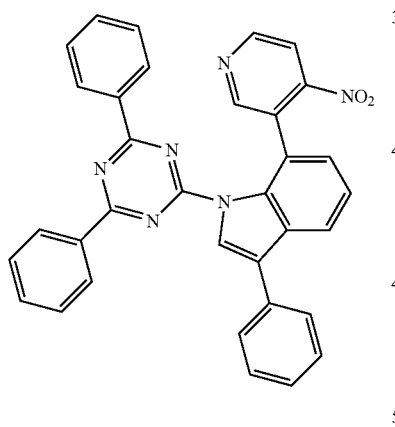

The 7-(4-nitropyridin-3-yl)-3-phenyl-1H-indole (5 g, 15.85 mmol) obtained in <Step 3> was dissolved in 50 ml of DMF under nitrogen, NaH (0.57 g, 23.77 mmol) was added thereto, and the resulting mixture was stirred for 1 hour. 2-chloro-4,6-diphenyl-1,3,5-triazine (6.36 g, 23.77 mmol) dissolved in 100 ml of DMF was slowly added thereto. After the mixture was stirred for 2 hours, 1-(4,6-diphenyl-1,3,5-triazin-2-yl)-7-(4-nitropyridin-3-yl)-3-phenyl-1H-indole (6.58 g, yield 76%) was obtained by terminating the reaction, filtering the mixture through silica, washing the filtrate with water and methanol, and then removing the solvent.

GC-Mass (theoretical value: 546.18 g/mol, measured value: 546 g/mol)

<Step 5> Synthesis of IC-5

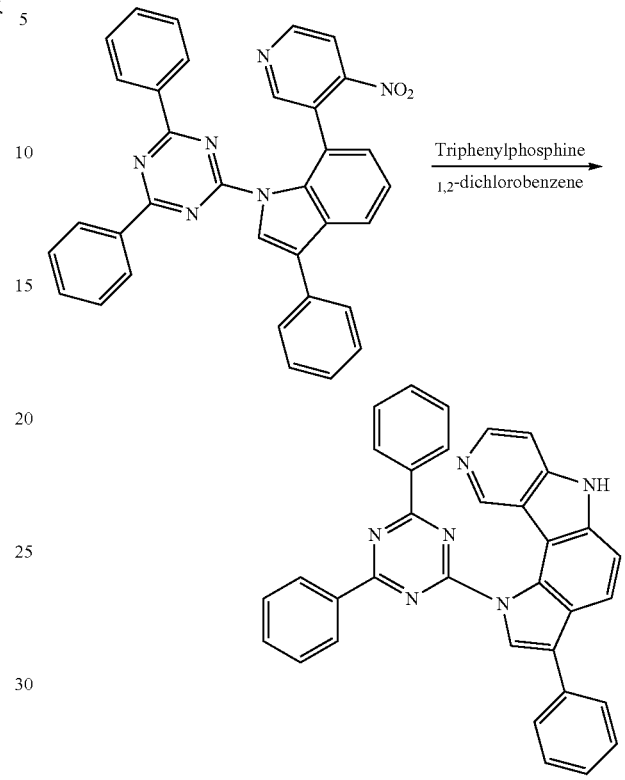

IC-5 was obtained by performing the same procedure as in <Step 4> of Preparation Example 1, except that the 1-(4,6-diphenyl-1,3,5-triazin-2-yl)-7-(4-nitropyridin-3-yl)-3-phenyl-1H-indole obtained in <Step 4> was used instead of 1-(biphenyl-3-yl)-6-(3-nitropyridin-2-yl)-1H-indole.

GC-Mass (theoretical value: 514.19 g/mol, measured value: 514 g/mol)

PREPARATION EXAMPLE 6

Synthesis of IC-6

<Step 1> Synthesis of 6-(3-nitropyridin-4-yl)-1H-indole

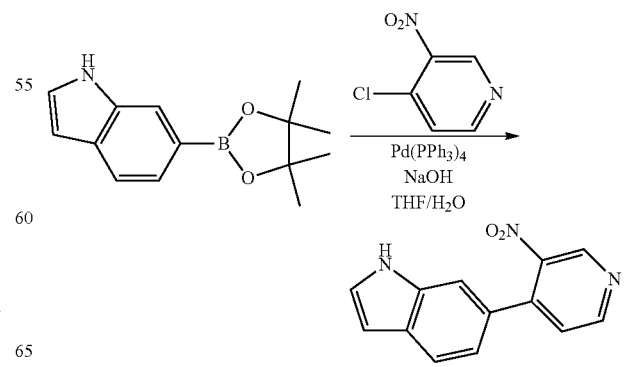

6-(3-nitropyridin-4-yl)-1H-indole was obtained by performing the same procedure as in <Step 2> of Preparation Example 1, except that the 3-phenyl-7-(4,4,5,5-tetramethyl-1,3,2-dioxaborolan-2-yl)-1H-indole obtained in <Step 1> of Preparation Example 1 and 4-chloro-3-nitropyridine were used instead of 2-chloro-3-nitropyridine.

$^1$H-NMR: δ 6.47 (d, 1H), 7.28 (d, 1H), 7.43 (d, 1H), 7.54 (d, 1H), 7.99 (s, 1H), 8.25 (s, 1H), 8.32 (d, 1H), 8.45 (d, 1H), 8.52 (s, 1H)

<Step 2> Synthesis of 6-(3-nitropyridin-4-yl)-1-(4-phenylpyridin-2-yl)-1H-indole

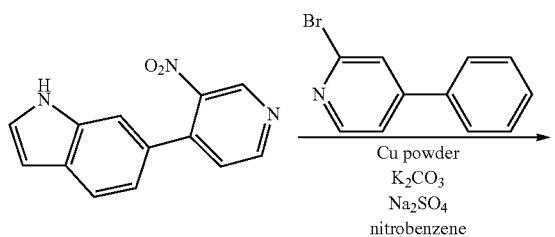

6-(3-nitropyridin-4-yl)-1-(4-phenylpyridin-2-yl)-1H-indole was obtained by performing the same procedure as in <Step 3> of Preparation Example 1, except that the 6-(3-nitropyridin-4-yl)-1H-indole obtained in <Step 1> and 2-bromo-4-phenylpyridine were used instead of 6-(3-nitropyridin-2-yl)-1H-indole and 3-bromobiphenyl.

$^1$H-NMR: δ 6.47 (d, 1H), 7.28 (d, 1H), 7.43 (m, 4H), 7.53 (m, 3H), 7.62 (s, 1H), 7.99 (s, 1H), 8.25 (s, 1H), 8.32 (d, 1H), 8.45 (m, 2H), 8.52 (m, 2H)

<Step 3> Synthesis of IC-6

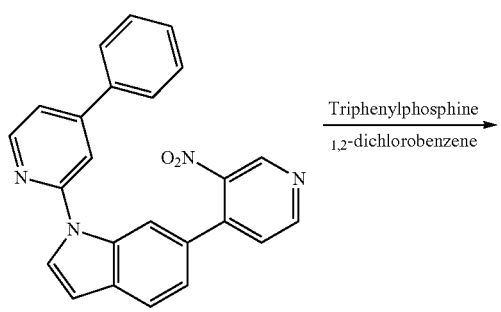

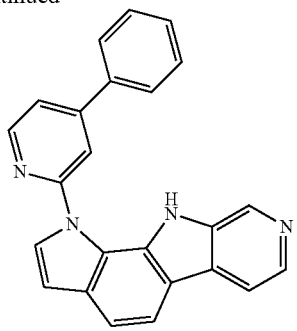

IC-6 was obtained by performing the same procedure as in <Step 4> of Preparation Example 1, except that the 6-(3-nitropyridin-4-yl)-1-(4-phenylpyridin-2-yl)-1H-indole obtained in <Step 2> was used instead of 1-(biphenyl-3-yl)-6-(3-nitropyridin-2-yl)-1H-indole.

$^1$H-NMR: δ 6.47 (d, 1H), 7.28 (d, 1H), 7.43 (m, 4H), 7.53 (m, 3H), 7.62 (s, 1H), 8.03 (s, 1H), 8.25 (s, 1H), 8.32 (d, 1H), 8.45 (m, 2H), 8.52 (m, 2H)

PREPARATION EXAMPLE 7

Synthesis of IC-7

<Step 1> Synthesis of 1-(4-(naphthalen-1-yl)phenyl)-6-(3-nitropyridin-4-yl)-1H-indole

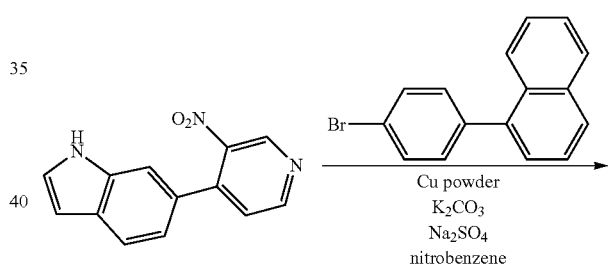

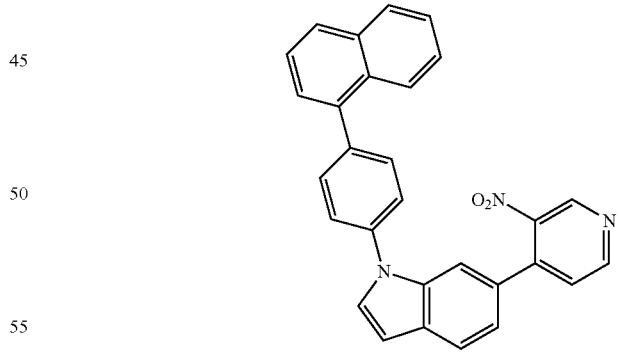

1-(4-(naphthalen-1-yl)phenyl)-6-(3-nitropyridin-4-yl)-1H-indole was obtained by performing the same procedure as in <Step 3> of Preparation Example 1, except that the 6-(3-nitropyridin-4-yl)-1H-indole obtained in <Step 1> of Preparation Example 6 and 1-(4-bromophenyl)naphthalene were used instead of 6-(3-nitropyridin-2-yl)-1H-indole and 3-bromobiphenyl.

$^1$H-NMR: δ 6.47 (d, 1H), 7.28 (d, 1H), 7.43 (d, 1H), 7.54 (m, 3H), 7.61 (m, 3H), 7.79 (d, 2H), 7.99 (m, 2H), 8.25 (d, 1H), 8.32 (m, 2H), 8.45 (m, 2H), 8.52 (s, 1H)

<Step 2> Synthesis of IC-7

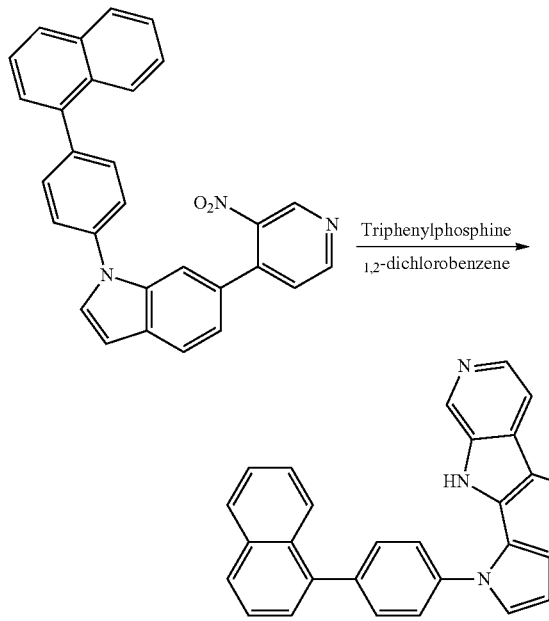

IC-7 was obtained by performing the same procedure as in <Step 4> of Preparation Example 1, except that the 1-(4-(naphthalen-1-yl)phenyl)-6-(3-nitropyridin-4-yl)-1H-indole obtained in <Step 1> was used instead of 1-(biphenyl-3-yl)-6-(3-nitropyridin-2-yl)-1H-indole.

GC-Mass (theoretical value: 409.16 g/mol, measured value: 409 g/mol)

PREPARATION EXAMPLE 8

Synthesis of IC-8

<Step 1> Synthesis of 7-chloro-2,3-diphenyl-1H-indole

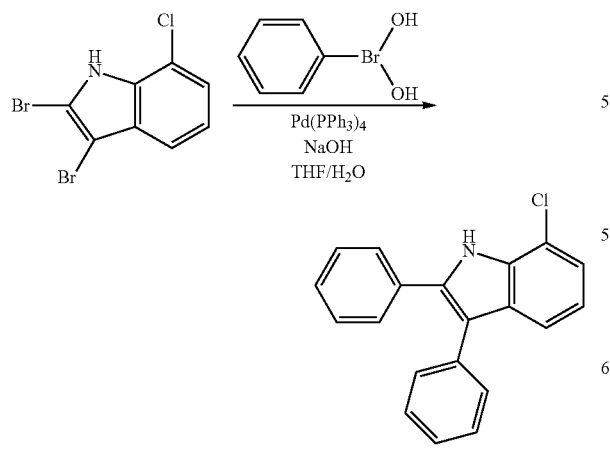

7-chloro-2,3-diphenyl-1H-indole was obtained by performing the same procedure as in <Step 2> of Preparation Example 1, except that 2,3-dibromo-7-chloro-1H-indole and phenylboronic acid were used instead of 2-chloro-3-nitropyridine and 6-(4,4,5,5-tetramethyl-1,3,2-dioxaborolan-2-yl)-1H-indole.

GC-Mass (theoretical value: 303.08 g/mol, measured value: 303 g/mol)

<Step 2> Synthesis of 2,3-diphenyl-7-(4,4,5,5-tetramethyl-1,3,2-dioxaborolan-2-yl)-1H-indole

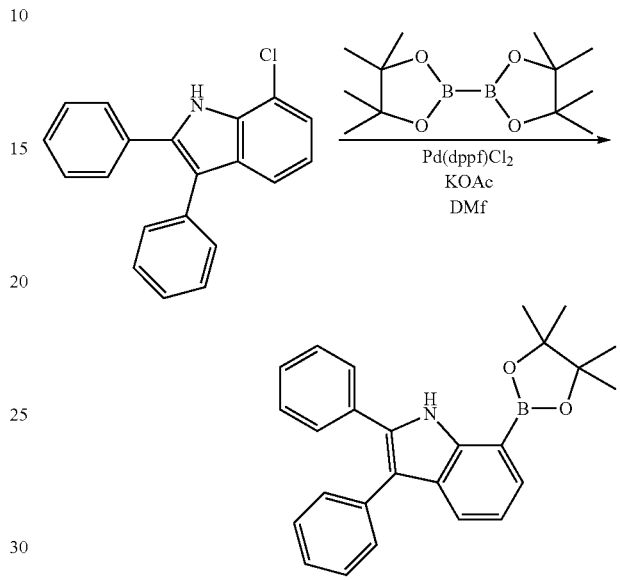

2,3-diphenyl-7-(4,4,5,5-tetramethyl-1,3,2-dioxaborolan-2-yl)-1H-indole was obtained by performing the same procedure as in <Step 1> of Preparation Example 1, except that the 7-chloro-2,3-diphenyl-1H-indole obtained in <Step 1> was used instead of 6-bromo-1H-indole.

GC-Mass (theoretical value: 395.21 g/mol, measured value: 395 g/mol)

<Step 3> Synthesis of 7-(3-nitropyridin-4-yl)-2,3-diphenyl-1H-indole

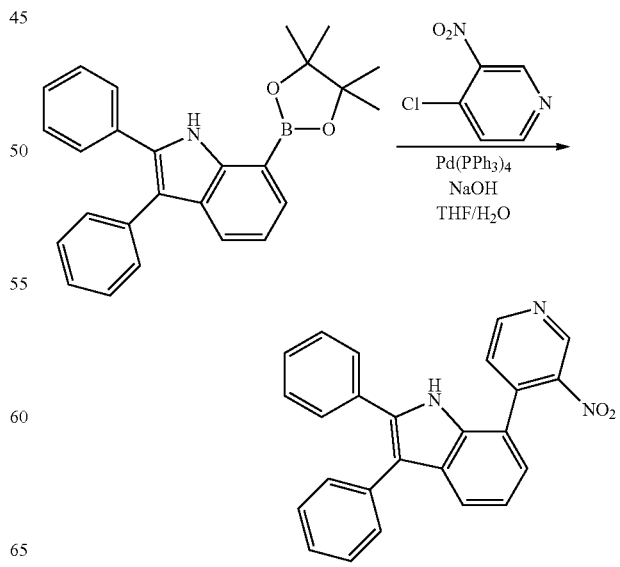

7-(3-nitropyridin-4-yl)-2,3-diphenyl-1H-indole was obtained by performing the same procedure as in <Step 2> of Preparation Example 1, except that the 3-phenyl-7-(4,4,5,5-tetramethyl-1,3,2-dioxaborolan-2-yl)-1H-indole obtained in <Step 2> and 4-chloro-3-nitropyridine were used instead of 6-(4,4,5,5-tetramethyl-1,3,2-dioxaborolan-2-yl)-1H-indole and 2-chloro-3-nitropyridine.

GC-Mass (theoretical value: 391.13 g/mol, measured value: 391.13 g/mol)

<Step 4> Synthesis of 7-(3-nitropyridin-4-yl)-2,3-diphenyl-1-(4-(pyridin-2-yl)phenyl)-1H-indole

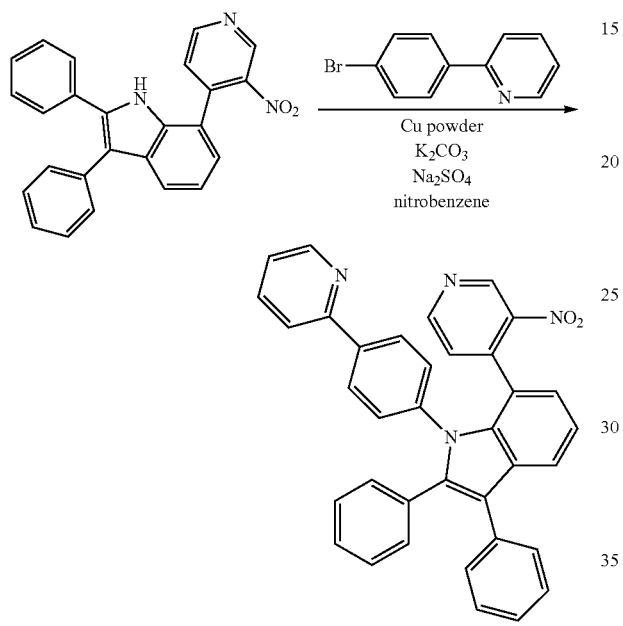

7-(3-nitropyridin-4-yl)-2,3-diphenyl-1-(4-(pyridin-2-yl)phenyl)-1H-indole was obtained by performing the same procedure as in <Step 3> of Preparation Example 1, except that the 7-(3-nitropyridin-4-yl)-2,3-diphenyl-1H-indole obtained in <Step 3> and 2-(4-bromophenyl)pyridine were used instead of 6-(3-nitropyridin-2-yl)-1H-indole and 3-bromobiphenyl.

GC-Mass (theoretical value: 544.19 g/mol, measured value: 544 g/mol)

<Step 5> Synthesis of IC-8

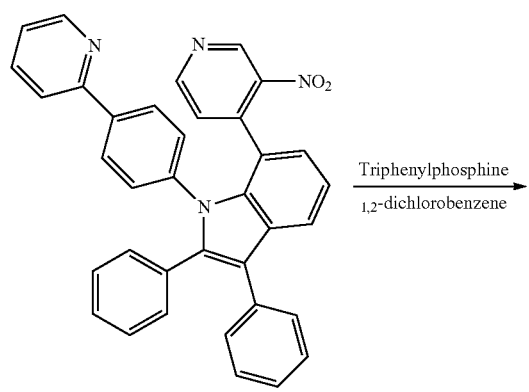

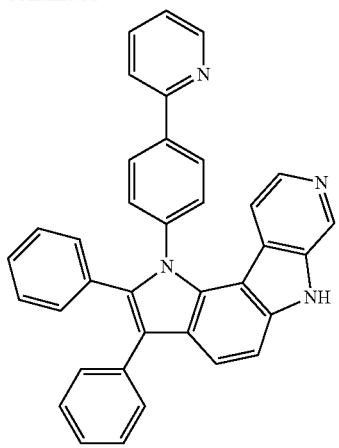

IC-8 was obtained by performing the same procedure as in <Step 4> of Preparation Example 1, except that the 7-(3-nitropyridin-4-yl)-2,3-diphenyl-1-(4-(pyridin-2-yl)phenyl)-1H-indole obtained in <Step 1> was used instead of 1-(biphenyl-3-yl)-6-(3-nitropyridin-2-yl)-1H-indole.

GC-Mass (theoretical value: 512.20 g/mol, measured value: 512 g/mol)

PREPARATION EXAMPLE 9

Synthesis of IC-9

<Step 1> Synthesis of 7-(4,4,5,5-tetramethyl-1,3,2-dioxaborolan-2-yl)-1H-indole

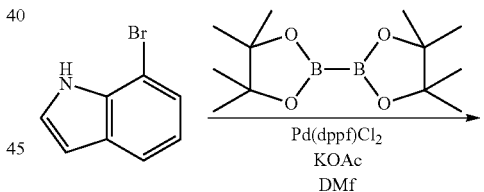

7-(4,4,5,5-tetramethyl-1,3,2-dioxaborolan-2-yl)-1H-indole was obtained by performing the same procedure as in <Step 1> of Preparation Example 1, except that 7-bromo-1H-indole was used instead of 6-bromo-1H-indole.

$^1$H-NMR: δ 1.25 (s, 12H), 6.43 (d, 1H), 7.25 (d, 1H), 7.45 (t, 1H), 7.56 (d, 1H), 7.71 (d, 1H), 8.22 (s, 1H)

\<Step 2\> Synthesis of 7-(2-nitropyridin-3-yl)-1H-indole

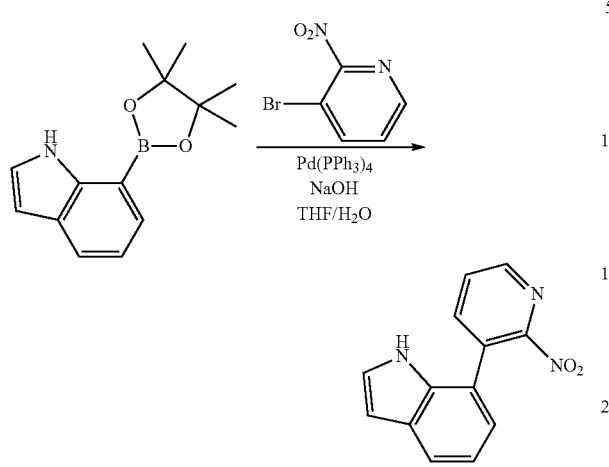

7-(2-nitropyridin-3-yl)-1H-indole was obtained by performing the same procedure as in \<Step 2\> of Preparation Example 1, except that the 7-(4,4,5,5-tetramethyl-1,3,2-dioxaborolan-2-yl)-1H-indole obtained in \<Step 1\> and 3-bromo-2-nitropyridine were used instead of 6-(4,4,5,5-tetramethyl-1,3,2-dioxaborolan-2-yl)-1H-indole and 2-chloro-3-nitropyridine.

$^1$H-NMR: δ 6.45 (d, 1H), 7.26 (d, 1H), 7.44 (t, 1H), 7.55 (d, 1H), 7.72 (d, 1H), 8.22 (m, 2H), 8.41 (d, 1H), 8.52 (d, 1H)

\<Step 3\> Synthesis of 1-(2,2'-bipyridin-5-yl)-7-(2-nitropyridin-3-yl)-1H-indole

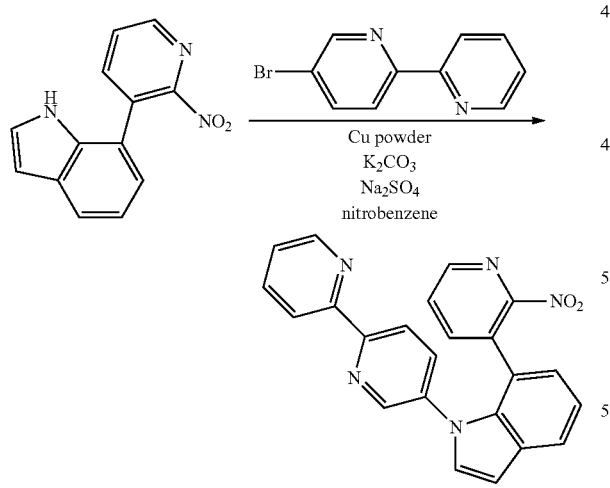

1-(2,2'-bipyridin-5-yl)-7-(2-nitropyridin-3-yl)-1H-indole was obtained by performing the same procedure as in \<Step 3\> of Preparation Example 1, except that the 7-(2-nitropyridin-3-yl)-1H-indole obtained in \<Step 2\> and 5-bromo-2,2'-bipyridine were used instead of 6-(3-nitropyridin-2-yl)-1H-indole and 3-bromobiphenyl.

GC-Mass (theoretical value: 393.12 g/mol, measured value: 393 g/mol)

\<Step 4\> Synthesis of IC-9

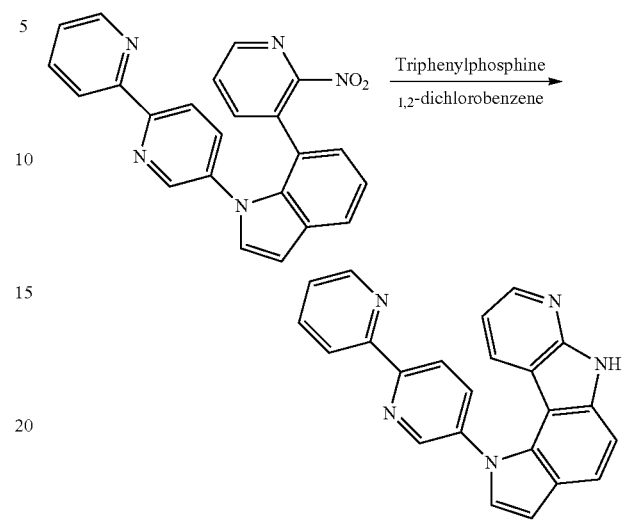

IC-9 was obtained by performing the same procedure as in \<Step 4\> of Preparation Example 1, except that the 1-(2,2'-bipyridin-5-yl)-7-(2-nitropyridin-3-yl)-1H-indole obtained in \<Step 3\> was used instead of 1-(biphenyl-3-yl)-6-(3-nitropyridin-2-yl)-1H-indole.

GC-Mass (theoretical value: 361.13 g/mol, measured value: 361 g/mol)

PREPARATION EXAMPLE 10

Synthesis of IC-10

\<Step 1\> Synthesis of 6-(2-nitrophenyl)-1H-pyrrolo[3,2-b]pyridine

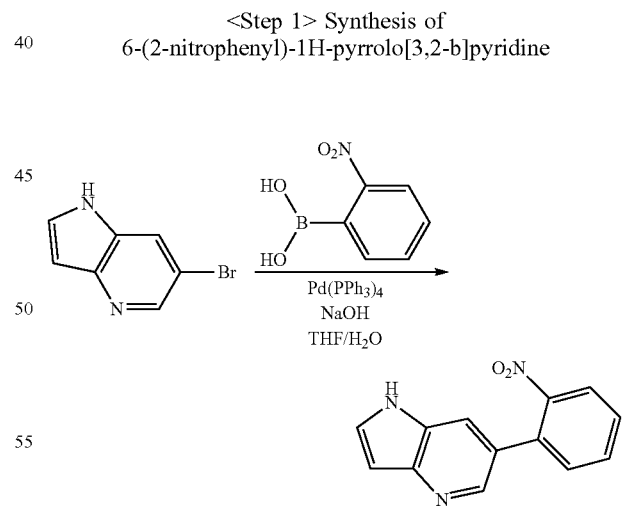

6-(2-nitrophenyl)-1H-pyrrolo[3,2-b]pyridine was obtained by performing the same procedure as in \<Step 2\> of Preparation Example 1, except that 6-bromo-1H-pyrrolo[3,2-b]pyridine and 2-nitrophenylboronic acid were used instead of 6-(4,4,5,5-tetramethyl-1,3,2-dioxaborolan-2-yl)-1H-indole and 2-chloro-3-nitropyridine.

$^1$H-NMR: δ 6.45 (d, 1H), 7.53 (d, 1H), 7.67 (t, 1H), 7.97 (t, 1H), 7.97 (s, 1H), 8.03 (m, 2H), 8.23 (s, 1H), 8.52 (s, 1H)

\<Step 2\> Synthesis of 1-(4,6-di(biphenyl-3-yl)-1,3,5-triazin-2-yl)-6-(2-nitrophenyl)-1H-pyrrolo[3,2-b]pyridine

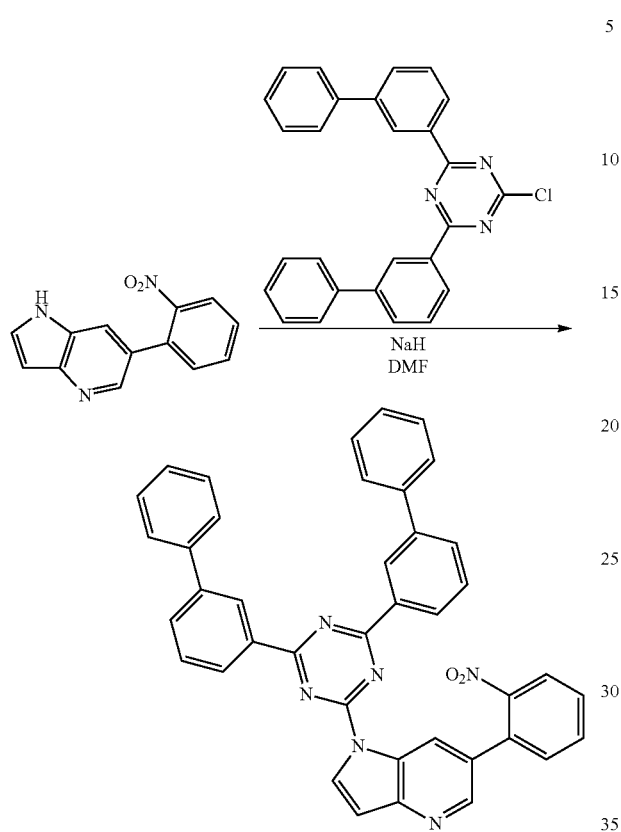

1-(4,6-di(biphenyl-3-yl)-1,3,5-triazin-2-yl)-6-(2-nitrophenyl)-1H-pyrrolo[3,2-b]pyridine was obtained by performing the same procedure as in \<Step 5\> of Preparation Example 5, except that the 6-(2-nitrophenyl)-1H-pyrrolo[3,2-b]pyridine obtained in \<Step 1\> and 2,4-di(biphenyl-3-yl)-6-chloro-1,3,5-triazine were used instead of 7-(4-nitropyridin-3-yl)-3-phenyl-1H-indole and 2-chloro-4,6-diphenyl-1,3,5-triazine.

GC-Mass (theoretical value: 622.21 g/mol, measured value: 622 g/mol)

\<Step 3\> Synthesis of IC-10

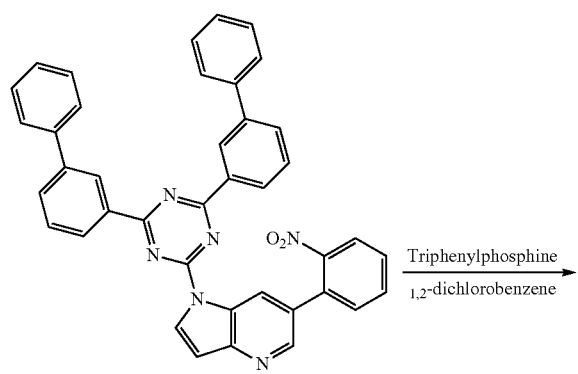

IC-10 was obtained by performing the same procedure as in \<Step 4\> of Preparation Example 1, except that the 1-(4,6-di(biphenyl-3-yl)-1,3,5-triazin-2-yl)-6-(2-nitrophenyl)-1H-pyrrolo[3,2-b]pyridine obtained in \<Step 2\> was used instead of 1-(biphenyl-3-yl)-6-(3-nitropyridin-2-yl)-1H-indole.

GC-Mass (theoretical value: 590.22 g/mol, measured value: 590 g/mol)

PREPARATION EXAMPLE 11

Synthesis of IC-11

\<Step 1\> Synthesis of 7-(4,4,5,5-tetramethyl-1,3,2-dioxaborolan-2-yl)-1H-pyrrolo[3,2-c]pyridine

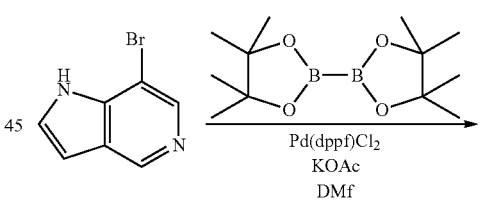

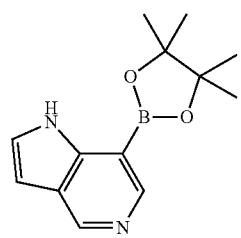

7-(4,4,5,5-tetramethyl-1,3,2-dioxaborolan-2-yl)-1H-pyrrolo[3,2-c]pyridine was obtained by performing the same procedure as in \<Step 1\> of Preparation Example 1, except that 7-bromo-1H-pyrrolo[3,2-c]pyridine was used instead of 6-bromo-1H-indole.

$^1$H-NMR: δ 1.25 (s, 12H), 6.43 (d, 1H), 7.25 (d, 1H), 8.22 (s, 1H), 8.32 (s, 1H), 8.41 (s, 1H)

\<Step 2\> Synthesis of 7-(4-nitropyridin-3-yl)-1H-pyrrolo[3,2-c]pyridine

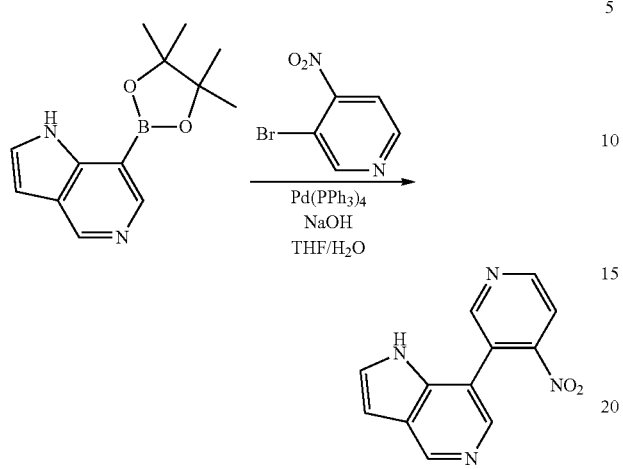

7-(4-nitropyridin-3-yl)-1H-pyrrolo[3,2-c]pyridine was obtained by performing the same procedure as in \<Step 2\> of Preparation Example 1, except that the 7-(4,4,5,5-tetramethyl-1,3,2-dioxaborolan-2-yl)-1H-pyrrolo[3,2,c]pyridine obtained in \<Step 1\> and 3-bromo-4-nitropyridine were used instead of 6-(4,4,5,5-tetramethyl-1,3,2-dioxaborolan-2-yl)-1H-indole and 2-chloro-3-nitropyridine.

$^1$H-NMR: δ 6.43 (d, 1H), 7.25 (d, 1H), 7.95 (d, 1H), 8.14 (d, 1H), 8.22 (s, 1H), 8.32 (s, 1H), 8.41 (m, 2H)

\<Step 3\> Synthesis of 7-(4-nitropyridin-3-yl)-1-phenyl-1H-pyrrolo[3,2-c]pyridine

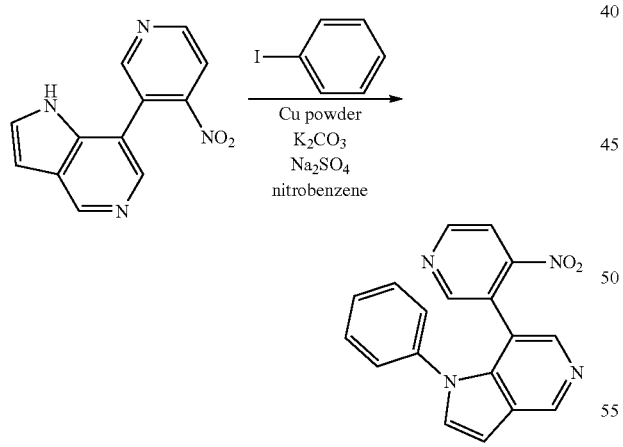

7-(4-nitropyridin-3-yl)-1-phenyl-1H-pyrrolo[3,2-c]pyridine was obtained by performing the same procedure as in \<Step 3\> of Preparation Example 1, except that the 7-(4-nitropyridin-3-yl)-1H-pyrrolo[3,2-c]pyridine obtained in \<Step 2\> and iodobenzene were used instead of 6-(3-nitropyridin-2-yl)-1H-indole and 3-bromobiphenyl.

$^1$H-NMR: δ 6.43 (d, 1H), 7.25 (d, 1H), 7.47 (m, 3H), 7.56 (d, 2H), 7.95 (d, 1H), 8.14 (d, 1H), 8.22 (s, 1H), 8.32 (s, 1H), 8.41 (m, 2H)

\<Step 4\> Synthesis of IC-11

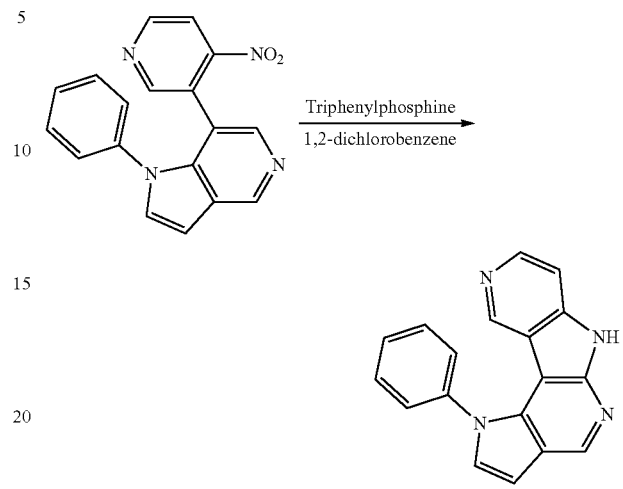

IC-11 was obtained by performing the same procedure as in \<Step 4\> of Preparation Example 1, except that the 7-(4-nitropyridin-3-yl)-1-phenyl-1H-pyrrolo[3,2-c]pyridine obtained in \<Step 3\> was used instead of 1-(biphenyl-3-yl)-6-(3-nitropyridin-2-yl)-1H-indole.

$^1$H-NMR: δ 6.44 (d, 1H), 7.26 (d, 1H), 7.46 (m, 3H), 7.55 (d, 2H), 7.96 (d, 1H), 8.15 (d, 1H), 8.23 (m, 2H), 8.32 (s, 1H)

PREPARATION EXAMPLE 12

Synthesis of IC-12

\<Step 1\> Synthesis of 5-(4,4,5,5-tetramethyl-1,3,2-dioxaborolan-2-yl)-1H-pyrrolo[2,3-b]pyridine

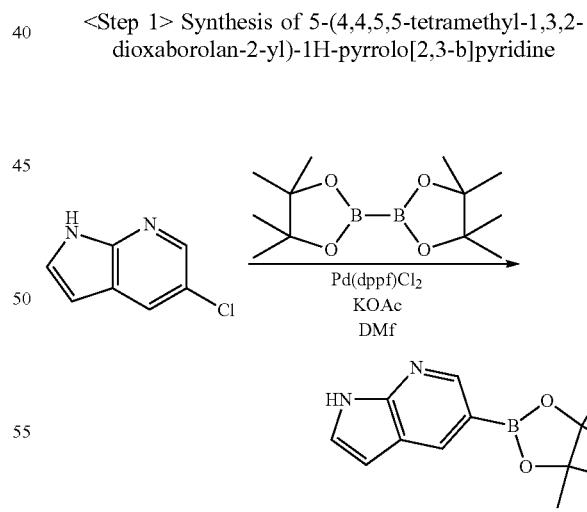

5-(4,4,5,5-tetramethyl-1,3,2-dioxaborolan-2-yl)-1H-pyrrolo[2,3-b]pyridine was obtained by performing the same procedure as in \<Step 1\> of Preparation Example 1, except that 5-chloro-1H-pyrrolo[2,3-b]pyridine was used instead of 6-bromo-1H-indole.

$^1$H-NMR: δ 1.25 (s, 12H), 6.43 (d, 1H), 7.25 (d, 1H), 8.22 (s, 1H), 8.32 (s, 1H), 8.41 (s, 1H)

\<Step 2\> Synthesis of 5-(2-nitropyridin-3-yl)-1H-pyrrolo[2,3-b]pyridine

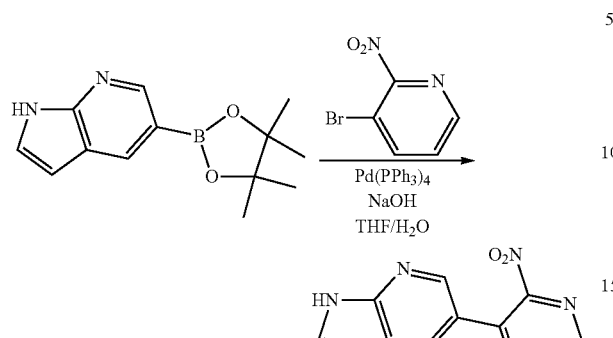

5-(2-nitropyridin-3-yl)-1H-pyrrolo[2,3-b]pyridine was obtained by performing the same procedure as in \<Step 2\> of Preparation Example 1, except that the 5-(4,4,5,5-tetramethyl-1,3,2-dioxaborolan-2-yl)-1H-pyrrolo[2,3-b]pyridine obtained in \<Step 1\> and 3-bromo-2-nitropyridine were used instead of 6-(4,4,5,5-tetramethyl-1,3,2-dioxaborolan-2-yl)-1H-indole and 2-chloro-3-nitropyridine.

$^1$H-NMR: δ 6.44 (d, 1H), 7.26 (d, 1H), 8.21 (m, 2H), 8.32 (s, 1H), 8.41 (m, 2H), 8.53 (d, 1H)

\<Step 3\> Synthesis of 1-(biphenyl-4-yl)-5-(2-nitropyridin-3-yl)-1H-pyrrolo[2,3-b]pyridine

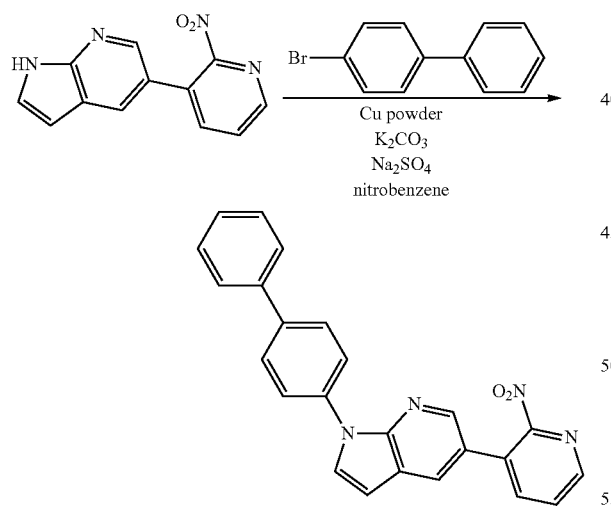

1-(biphenyl-4-yl)-5-(2-nitropyridin-3-yl)-1H-pyrrolo[2,3-b]pyridine was obtained by performing the same procedure as in \<Step 3\> of Preparation Example 1, except that the 5-(2-nitropyridin-3-yl)-1H-pyrrolo[2,3-b]pyridine obtained in \<Step 2\> and 4-bromobiphenyl were used instead of 6-(3-nitropyridin-2-yl)-1H-indole and 3-bromobiphenyl.

$^1$H-NMR: δ 6.45 (d, 1H), 7.25 (d, 1H), 7.41 (m, 1H), 7.52 (m, 4H), 7.68 (d, 2H), 7.79 (d, 2H), 8.22 (m, 2H), 8.42 (m, 2H), 8.52 (d, 1H)

\<Step 4\> Synthesis of IC-12

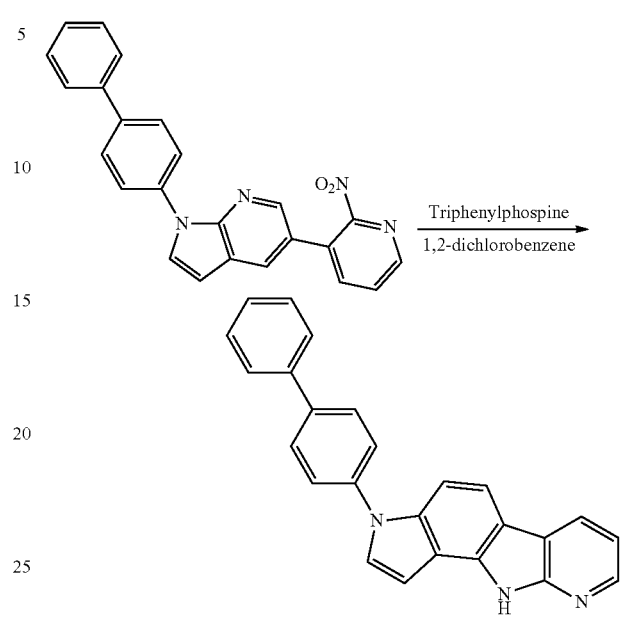

IC-12 was obtained by performing the same procedure as in \<Step 4\> of Preparation Example 1, except that the 1-(biphenyl-4-yl)-5-(2-nitropyridin-3-yl)-1H-pyrrolo[2,3-b]pyridine obtained in \<Step 3\> was used instead of 1-(biphenyl-3-yl)-6-(3-nitropyridin-2-yl)-1H-indole.

$^1$H-NMR: δ 6.45 (d, 1H), 7.25 (d, 1H), 7.41 (m, 1H), 7.52 (m, 4H), 7.68 (d, 2H), 7.79 (d, 2H), 8.22 (m, 2H), 8.32 (s, 1H), 8.42 (m, 2H)

PREPARATION EXAMPLE 13

Synthesis of IC-13

\<Step 1\> Synthesis of 5-(2-bromo-5-nitropyridin-4-yl)-1H-pyrrolo[2,3-b]pyridine

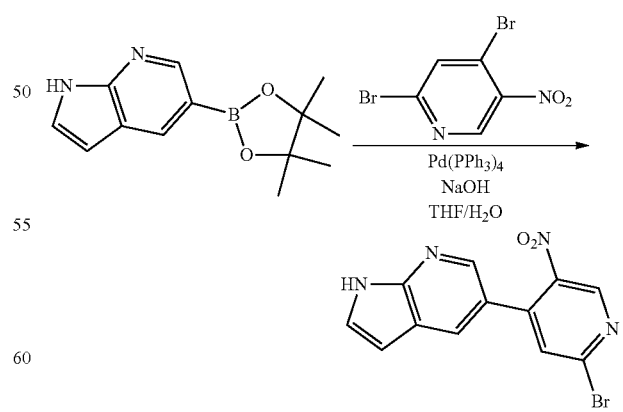

5-(2-bromo-5-nitropyridin-4-yl)-1H-pyrrolo[2,3-b]pyridine was obtained by performing the same procedure as in \<Step 2\> of Preparation Example 1, except that the 5-(4,4,5,5-tetramethyl-1,3,2-dioxaborolan-2-yl)-1H-pyrrolo[2,3-b]

pyridine obtained in <Step 1> of Preparation Example 12 and 2,4-bromo-5-nitropyridine were used instead of 6-(4,4,5,5-tetramethyl-1,3,2-dioxaborolan-2-yl)-1H-indole and 2-chloro-3-nitropyridine.

¹H-NMR: δ 6.43 (d, 1H), 7.25 (d, 1H), 8.25 (m, 2H), 8.32 (s, 1H), 8.41 (s, 1H), 8.54 (s, 1H)

<Step 2> Synthesis of 5-(5-nitro-2-phenylpyridin-4-yl)-1H-pyrrolo[2,3-b]pyridine

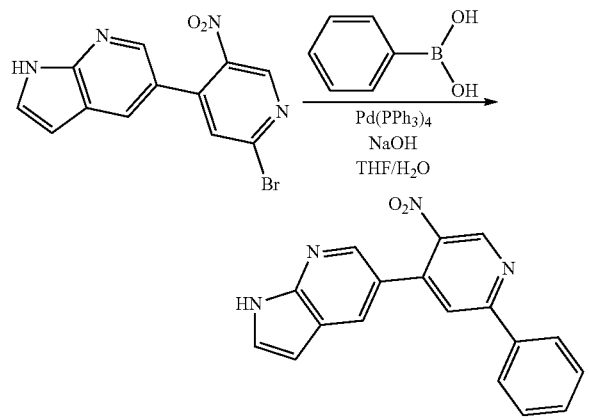

5-(5-nitro-2-phenylpyridin-4-yl)-1H-pyrrolo[2,3-b]pyridine was obtained by performing the same procedure as in <Step 2> of Preparation Example 1, except that the 5-(2-bromo-5-nitropyridin-4-yl)-1H-pyrrolo[2,3-b]pyridine obtained in <Step 1> and phenylboronic acid were used instead of 6-(4,4,5,5-tetramethyl-1,3,2-dioxaborolan-2-yl)-1H-indole and 2-chloro-3-nitropyridine.

¹H-NMR: δ 6.43 (d, 1H), 7.25 (d, 1H), 7.47 (m, 1H), 7.54 (d, 2H), 7.86 (d, 2H), 8.25 (m, 2H), 8.32 (s, 1H), 8.41 (s, 1H), 8.50 (s, 1H)

<Step 3> Synthesis of 2-(5-(5-nitro-2-phenylpyridin-4-yl)-1H-pyrrolo[2,3-b]pyridin-1-yl)quinoline

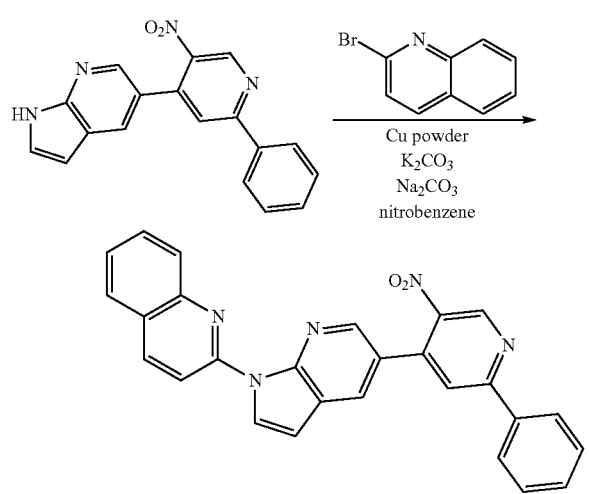

2-(5-(5-nitro-2-phenylpyridin-4-yl)-1H-pyrrolo[2,3-b]pyridin-1-yl)quinoline was obtained by performing the same procedure as in <Step 3> of Preparation Example 1, except that the 5-(5-nitro-2-phenylpyridin-4-yl)-1H-pyrrolo[2,3-b]pyridine obtained in <Step 2> and 2-bromoquinoline were used instead of 6-(3-nitropyridin-2-yl)-1H-indole and 3-bromobiphenyl.

GC-Mass (theoretical value: 443.14 g/mol, measured value: 443 g/mol)

<Step 4> Synthesis of IC-13

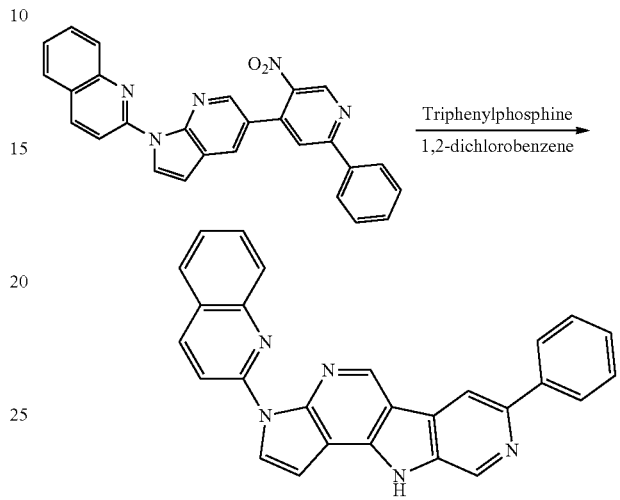

IC-13 was obtained by performing the same procedure as in <Step 4> of Preparation Example 1, except that the 2-(5-(5-nitro-2-phenylpyridin-4-yl)-1H-pyrrolo[2,3-b]pyridin-1-yl)quinoline obtained in <Step 3> was used instead of 1-(biphenyl-3-yl)-6-(3-nitropyridin-2-yl)-1H-indole.

GC-Mass (theoretical value: 411.15 g/mol, measured value: 411 g/mol)

PREPARATION EXAMPLE 14

Synthesis of IC-14

<Step 1> Synthesis of 4-(4,4,5,5-tetramethyl-1,3,2-dioxaborolan-2-yl)-1H-pyrrolo[2,3-c]pyridine

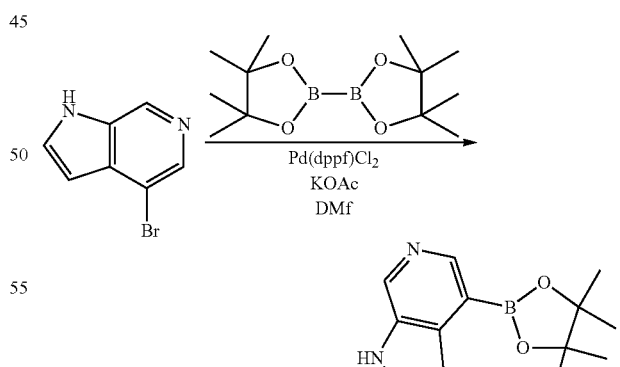

4-(4,4,5,5-tetramethyl-1,3,2-dioxaborolan-2-yl)-1H-pyrrolo[2,3-c]pyridine was obtained by performing the same procedure as in <Step 1> of Preparation Example 1, except that 4-bromo-1H-pyrrolo[2,3-c]pyridine was used instead of 6-bromo-1H-indole.

¹H-NMR: δ 1.24 (s, 12H), 6.44 (d, 1H), 7.24 (d, 1H), 8.41 (s, 2H)

<Step 2> Synthesis of 4-(1-nitronaphthalen-2-yl)-1H-pyrrolo[2,3-c]pyridine

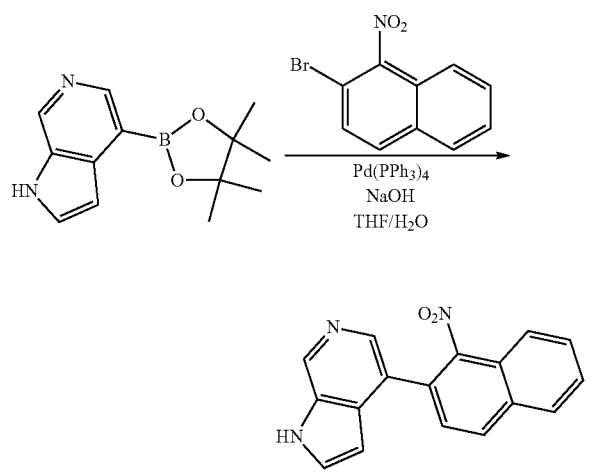

4-(1-nitronaphthalen-2-yl)-1H-pyrrolo[2,3-c]pyridine was obtained by performing the same procedure as in <Step 2> of Preparation Example 1, except that the 4-(4,4,5,5-tetramethyl-1,3,2-dioxaborolan-2-yl)-1H-pyrrolo[2,3-c]pyridine obtained in <Step 1> and 2-bromo-1-nitronaphthalene were used instead of 6-(4,4,5,5-tetramethyl-1,3,2-dioxaborolan-2-yl)-1H-indole and 2-chloro-3-nitropyridine.

$^1$H-NMR: δ 6.45 (d, 1H), 7.25 (d, 1H), 7.76 (m, 2H), 7.85 (m, 2H), 7.98 (m, 2H), 8.42 (s, 2H)

<Step 3> Synthesis of 4-(1-nitronaphthalen-2-yl)-1-phenyl-1H-pyrrolo[2,3-c]pyridine

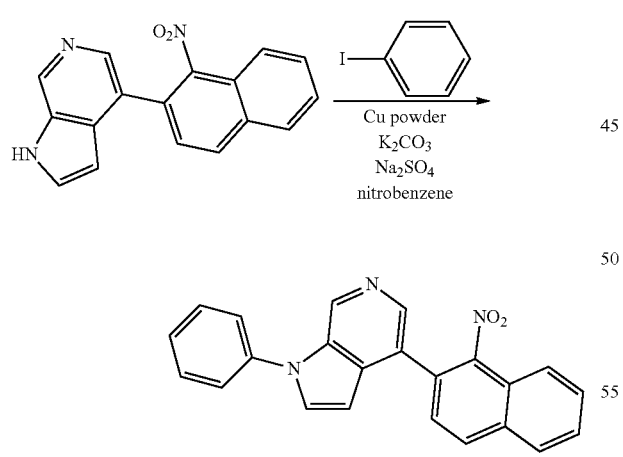

4-(1-nitronaphthalen-2-yl)-1-phenyl-1H-pyrrolo[2,3-c]pyridine was obtained by performing the same procedure as in <Step 3> of Preparation Example 1, except that the 4-(1-nitronaphthalen-2-yl)-1H-pyrrolo[2,3-c]pyridine obtained in <Step 2> and iodobenzene were used instead of 6-(3-nitropyridin-2-yl)-1H-indole and 3-bromobiphenyl.

GC-Mass (theoretical value: 365.12 g/mol, measured value: 365 g/mol)

<Step 4> Synthesis of IC-14

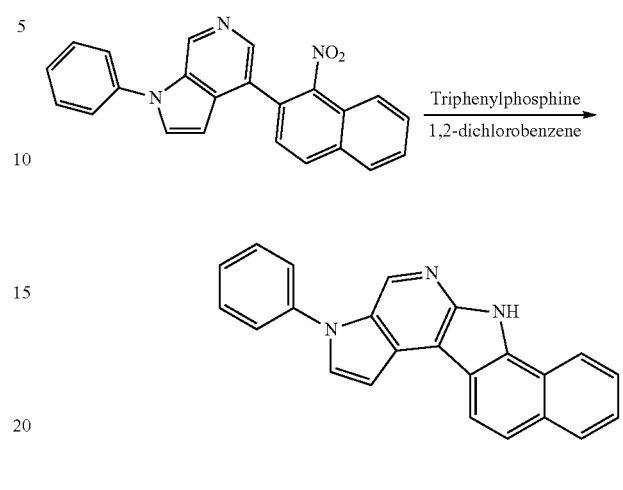

IC-14 was obtained by performing the same procedure as in <Step 4> of Preparation Example 1, except that the 4-(1-nitronaphthalen-2-yl)-1-phenyl-1H-pyrrolo[2,3-c]pyridine obtained in <Step 3> was used instead of 1-(biphenyl-3-yl)-6-(3-nitropyridin-2-yl)-1H-indole.

GC-Mass (theoretical value: 333.13 g/mol, measured value: 333 g/mol)

PREPARATION EXAMPLE 15

Synthesis of IC-15

<Step 1> Synthesis of 2-(benzo[b]thiophen-5-yl)-4,4,5,5-tetramethyl-1,3,2-dioxaborolane

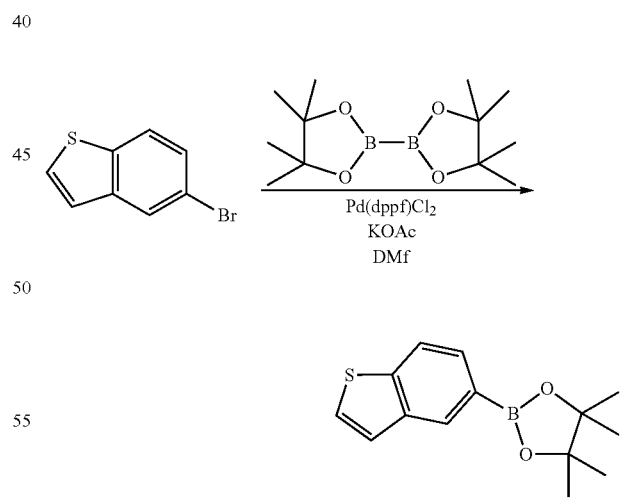

2-(benzo[b]thiophen-5-yl)-4,4,5,5-tetramethyl-1,3,2-dioxaborolane was obtained by performing the same procedure as in <Step 1> of Preparation Example 1, except that 5-bromobenzo[b]thiophene was used instead of 6-bromo-1H-indole.

$^1$H-NMR: δ 1.24 (s, 12H), 7.65 (d, 1H), 7.85 (d, 1H), 7.98 (d, 1H), 8.07 (d, 1H), 8.12 (s, 1H)

<Step 2> Synthesis of 2-(benzo[b]thiophen-5-yl)-3-nitropyridine

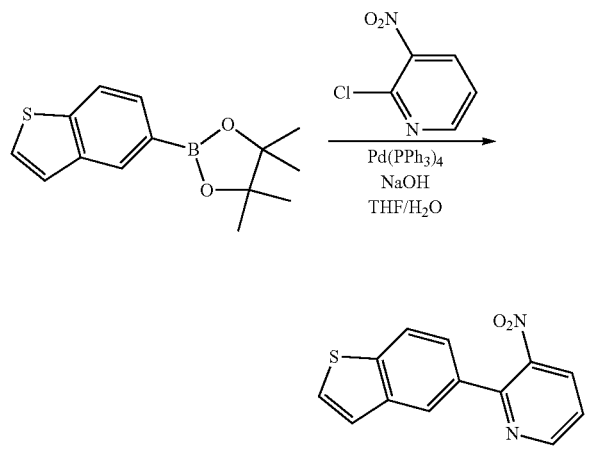

2-(benzo[b]thiophen-5-yl)-3-nitropyridine was obtained by performing the same procedure as in <Step 2> of Preparation Example 1, except that the 2-(benzo[b]thiophen-5-yl)-4,4,5,5-tetramethyl-1,3,2-dioxaborolane obtained in <Step 1> was used instead of 6-(4,4,5,5-tetramethyl-1,3,2-dioxaborolan-2-yl)-1H-indole.

$^1$H-NMR: δ 7.66 (d, 1H), 7.89 (d, 1H), 7.97 (d, 1H), 8.01 (d, 1H), 8.09 (m, 2H), 8.14 (s, 1H), 8.42 (d, 1H)

<Step 3> Synthesis of IC-15

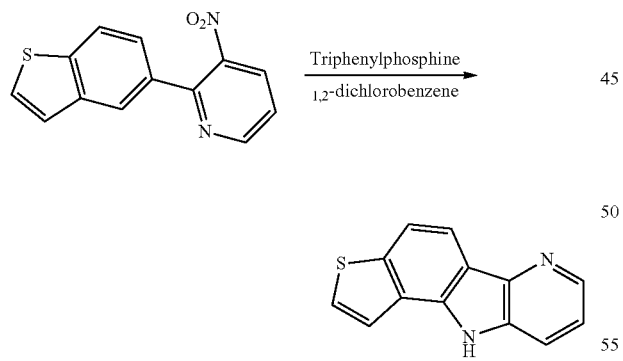

IC-15 was obtained by performing the same procedure as in <Step 4> of Preparation Example 1, except that the 2-(benzo[b]thiophen-5-yl)-3-nitropyridine obtained in <Step 2> was used instead of 1-(biphenyl-3-yl)-6-(3-nitropyridin-2-yl)-1H-indole.

$^1$H-NMR: δ 7.65 (d, 1H), 7.86 (d, 1H), 7.98 (d, 1H), 8.03 (d, 1H), 8.10 (m, 2H), 8.32 (s, 1H), 8.41 (d, 1H)

PREPARATION EXAMPLE 16

Synthesis of IC-16

<Step 1> Synthesis of 6-(2-isopropylphenyl)-1H-pyrrolo[3,2-b]pyridine

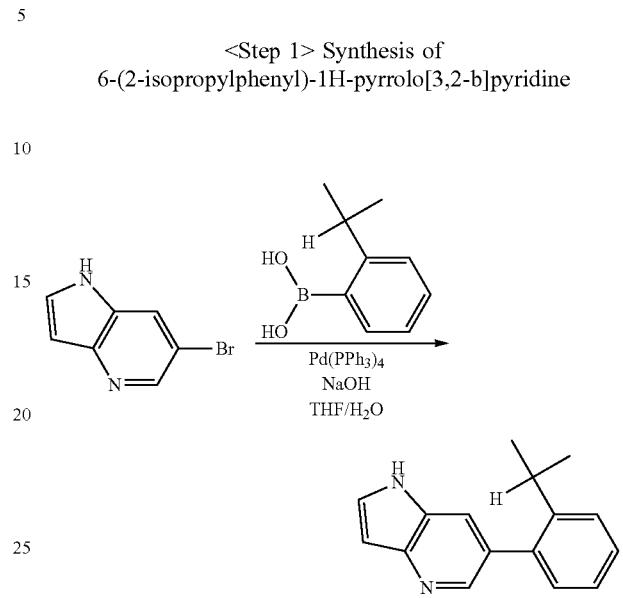

6-(2-isopropylphenyl)-1H-pyrrolo[3,2-b]pyridine was obtained by performing the same procedure as in <Step 2> of Preparation Example 1, except that 6-bromo-1H-pyrrolo[3,2-b]pyridine and 2-isopropylphenylboronic acid were used instead of 6-(4,4,5,5-tetramethyl-1,3,2-dioxaborolan-2-yl)-1H-indole and 2-chloro-3-nitropyridine.

$^1$H-NMR: δ 1.20 (s, 6H), 2.87 (s, 1H), 6.45 (d, 1H), 7.25 (d, 1H), 7.34 (m, 3H), 7.71 (d, 1H), 7.97 (s, 1H), 8.40 (s, 1H)

<Step 2> Synthesis of IC-16

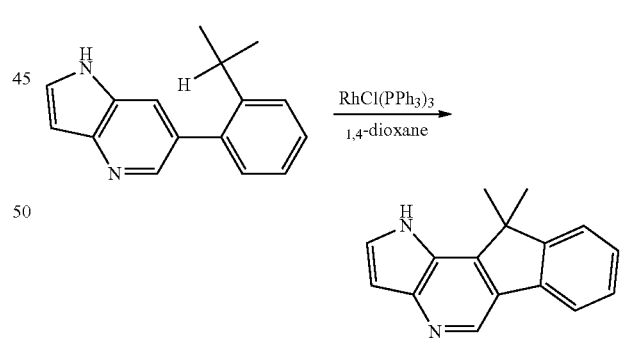

The 6-(2-isopropylphenyl)-1H-pyrrolo[3,2-b]pyridine (5 g, 21.16 mmol) obtained in <Step 1> and RhCl(PPh$_3$)$_3$ (97.88 mg, 0.5 mol %) were dissolved in 50 ml of 1,4-dioxane under nitrogen flow, and then the resulting mixture was stirred at 135° C. for 1 hour. After the reaction was terminated, IC-16 (3.92 g, yield 79%) was obtained by removing the solvent and purifying the residue with column chromatography (Hexane:MC=3:1 (v:v)).

$^1$H-NMR: δ 1.21 (s, 6H), 6.44 (d, 1H), 7.26 (d, 1H), 7.35 (m, 3H), 7.72 (d, 1H), 8.43 (s, 1H)

PREPARATION EXAMPLE 17

Synthesis of IC-17

<Step 1> Synthesis of 4-(2-benzhydrylphenyl)-1H-pyrrolo[2,3-c]pyridine

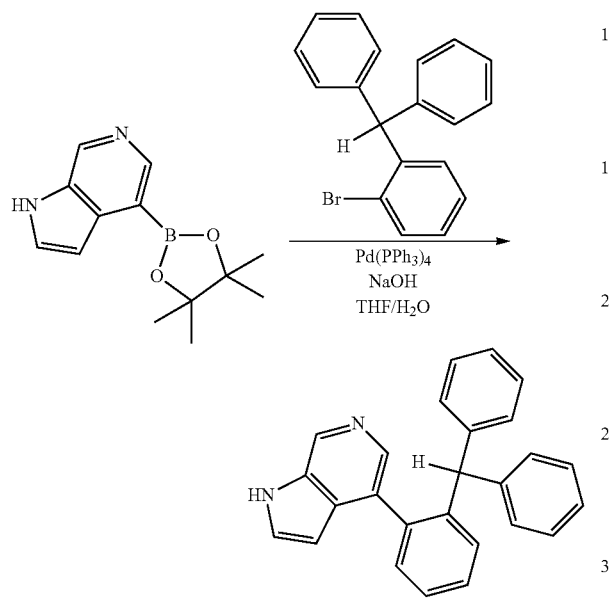

4-(2-benzhydrylphenyl)-1H-pyrrolo[2,3-c]pyridine was obtained by performing the same procedure as in <Step 2> of Preparation Example 1, except that the 4-(4,4,5,5-tetramethyl-1,3,2-dioxaborolan-2-yl)-1H-pyrrolo[2,3-c]pyridine obtained in <Step 1> of Preparation Example 14 and ((2-bromophenyl)methylene)dibenzene were used instead of 6-(4,4,5,5-tetramethyl-1,3,2-dioxaborolan-2-yl)-1H-indole and 2-chloro-3-nitropyridine.

GC-Mass (theoretical value: 360.16 g/mol, measured value: 360 g/mol)

<Step 2> Synthesis of IC-17

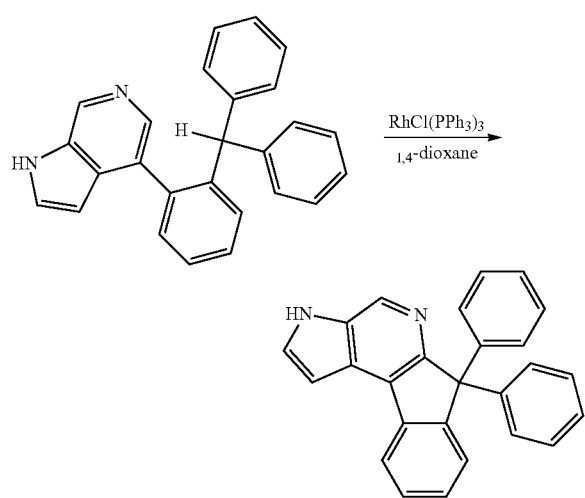

IC-17 was obtained by performing the same procedure as in <Step 2> of Preparation Example 16, except that the 4-(2-benzhydrylphenyl)-1H-pyrrolo[2,3-c]pyridine obtained in <Step 1> was used instead of 6-(2-isopropylphenyl)-1H-pyrrolo[3,2-b]pyridine.

GC-Mass (theoretical value: 358.15 g/mol, measured value: 358 g/mol)

SYNTHESIS EXAMPLE 1

Synthesis of INV-1

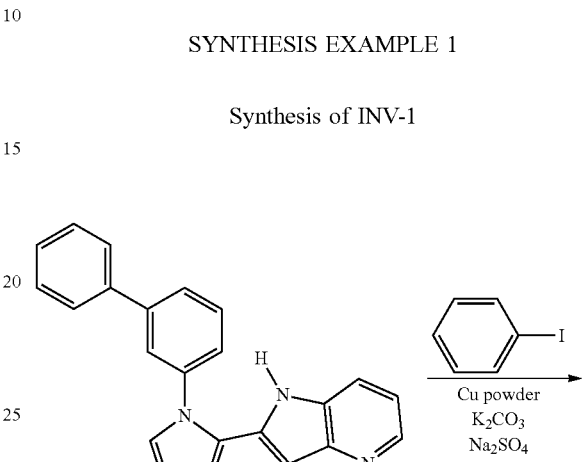

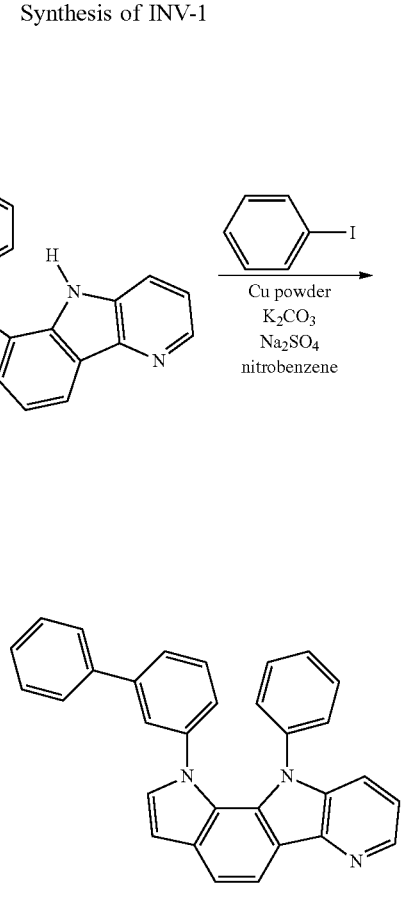

Inv-1

IC-1 (5 g, 13.91 mmol) which is the compound prepared in Preparation Example 1, iodobenzene (4.26 g, 20.87 mmol), Cu powder (0.09 g, 1.39 mmol), $K_2CO_3$ (1.92 g, 13.91 mmol), $Na_2SO_4$ (1.98 g, 13.91 mmol), and nitrobenzene (100 ml) were mixed under nitrogen flow, and the resulting mixture was stirred at 190° C. for 12 hours. After the reaction was terminated, nitrobenzene was removed, the organic layer was separated by methylene chloride, and water was removed by using $MgSO_4$. The target compound Inv-1 (4.60 g, yield 76%) was obtained by removing the solvent of the organic layer, and then purifying the residue with column chromatography (Hexane:EA=3:1 (v:v)).

GC-Mass (theoretical value: 435.17 g/mol, measured value: 435 g/mol)

SYNTHESIS EXAMPLE 2

Synthesis of INV-2

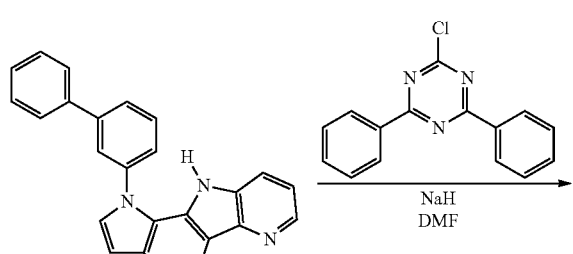

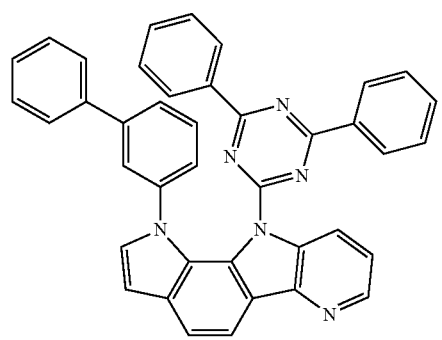

Inv-2

IC-1 (5 g, 13.91 mmol) which is the compound prepared in Preparation Example 1 was dissolved in 100 ml of DMF under nitrogen, NaH (0.50 g, 20.87 mmol) was added thereto, and the resulting mixture was stirred for 1 hour. 2-chloro-4,6-diphenyl-1,3,5-triazine (5.59 g, 20.87 mmol) dissolved in 100 ml of DMF was slowly added thereto. After the mixture was stirred for 3 hours, the reaction was terminated, the mixture was filtered through silica, the filtrate was washed with water and methanol, and then the solvent was removed. The target compound Inv-2 (6.00 g, yield 73%) was obtained by purifying the solid, from which the solvent had been removed, with column chromatography (Hexane: EA=1:1 (v:v)).

GC-Mass (theoretical value: 590.22 g/mol, measured value: 590 g/mol)

SYNTHESIS EXAMPLE 3

Synthesis of INV-3

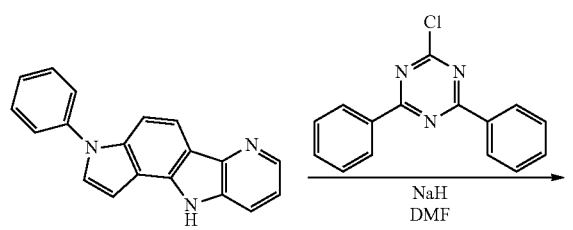

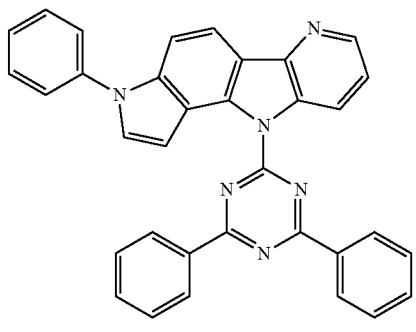

Inv-3

The target compound Inv-3 (7.63 g, yield 84%) was obtained by performing the same procedure as in Synthesis Example 2, except that IC-2 which is the compound prepared in Preparation Example 2 was used instead of IC-1.

GC-Mass (theoretical value: 514.19 g/mol, measured value: 514 g/mol)

SYNTHESIS EXAMPLE 4

Synthesis of INV-4

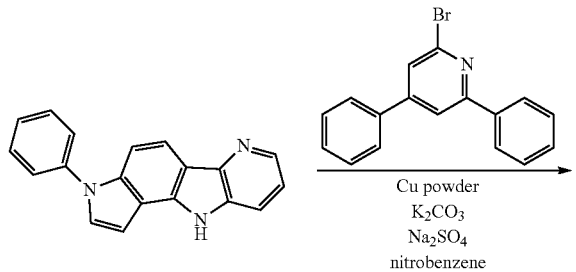

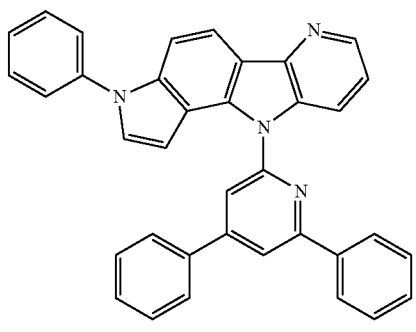

Inv-4

The target compound Inv-4 (6.06 g, yield 67%) was obtained by performing the same procedure as in Synthesis Example 1, except that IC-2 which is the compound prepared in Preparation Example 2 and 2-bromo-4,6-diphenylpyridine were used instead of IC-1 and iodobenzene.

GC-Mass (theoretical value: 512.20 g/mol, measured value: 512 g/mol)

SYNTHESIS EXAMPLE 5

Synthesis of INV-5

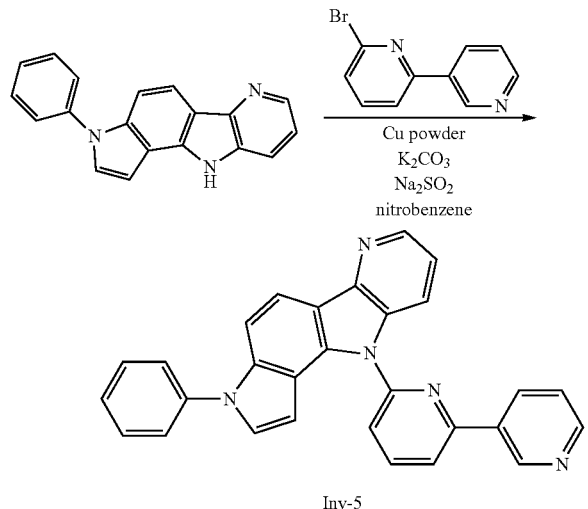

Inv-5

The target compound Inv-5 (4.63 g, yield 60%) was obtained by performing the same procedure as in Synthesis Example 1, except that IC-2 which is the compound prepared in Preparation Example 2 and 6-bromo-2,3'-bipyridine were used instead of IC-1 and iodobenzene.

GC-Mass (theoretical value: 437.16 g/mol, measured value: 437 g/mol)

SYNTHESIS EXAMPLE 6

Synthesis of INV-6

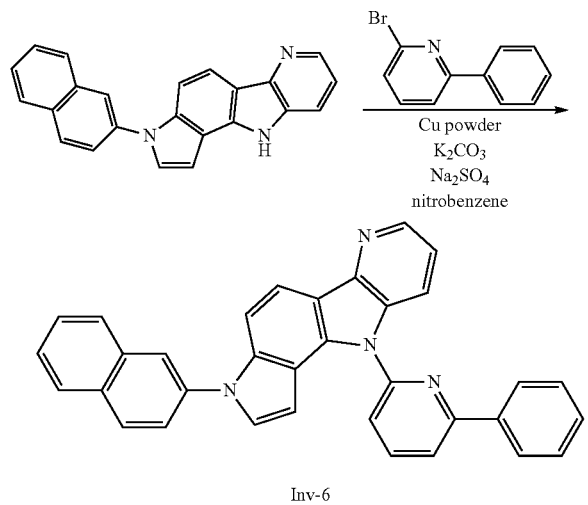

Inv-6

The target compound Inv-6 (4.09 g, yield 56%) was obtained by performing the same procedure as in Synthesis Example 1, except that IC-3 which is the compound prepared in Preparation Example 3 and 2-bromo-6-phenylpyridine were used instead of IC-1 and iodobenzene.

GC-Mass (theoretical value: 486.18 g/mol, measured value: 486 g/mol)

SYNTHESIS EXAMPLE 7

Synthesis of INV-7

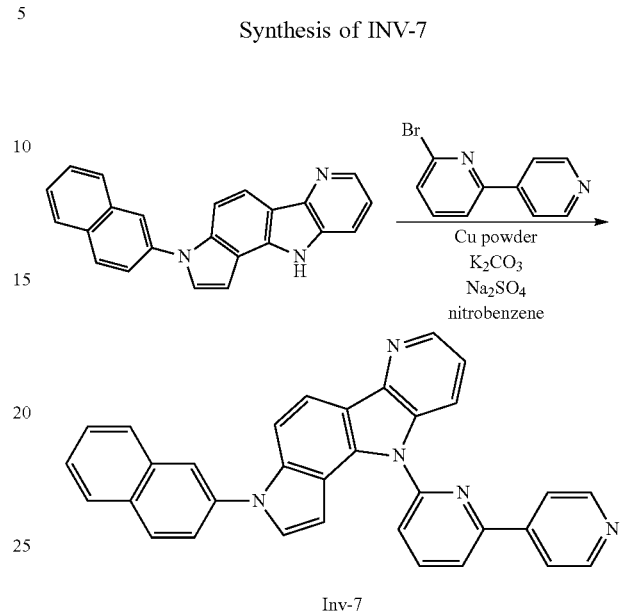

Inv-7

The target compound Inv-7 (3.95 g, yield 54%) was obtained by performing the same procedure as in Synthesis Example 1, except that IC-3 which is the compound prepared in Preparation Example 3 and 6-bromo-2,4'-bipyridine were used instead of IC-1 and iodobenzene.

GC-Mass (theoretical value: 487.18 g/mol, measured value: 487 g/mol)

SYNTHESIS EXAMPLE 8

Synthesis of INV-8

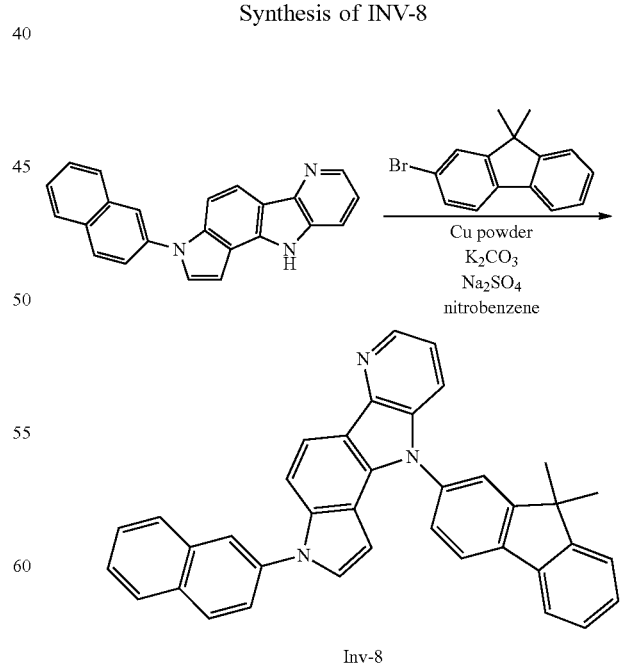

Inv-8

The target compound Inv-8 (5.20 g, yield 66%) was obtained by performing the same procedure as in Synthesis Example 1, except that IC-3 which is the compound prepared in Preparation Example 3 and 2-bromo-9,9-dimethyl-9H-fluorene were used instead of IC-1 and iodobenzene.

GC-Mass (theoretical value: 525.22 g/mol, measured value: 525 g/mol)

SYNTHESIS EXAMPLE 9

Synthesis of INV-9

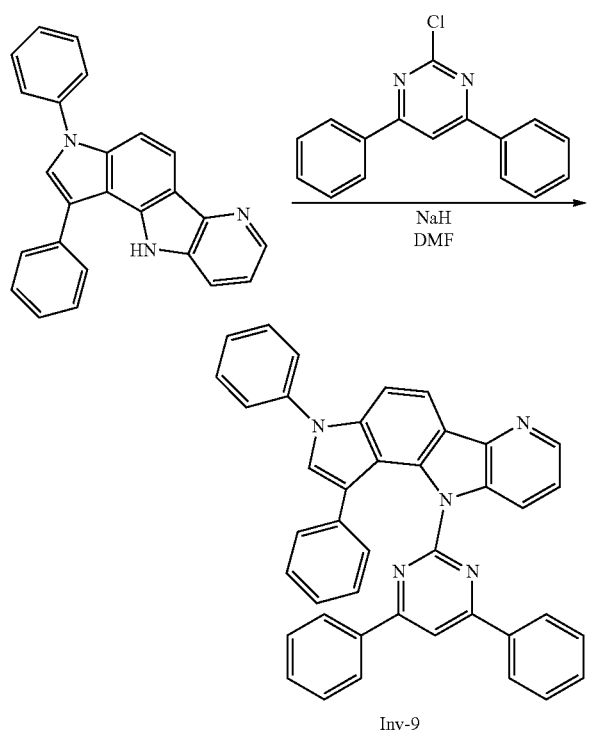

Inv-9

The target compound Inv-9 (6.15 g, yield 75%) was obtained by performing the same procedure as in Synthesis Example 2, except that IC-4 which is the compound prepared in Preparation Example 4 and 2-chloro-4,6-diphenylpyrimidine were used instead of IC-1 and 2-chloro-4,6-diphenyl-1,3,5-triazine.

GC-Mass (theoretical value: 589.23 g/mol, measured value: 589 g/mol)

SYNTHESIS EXAMPLE 10

Synthesis of INV-10

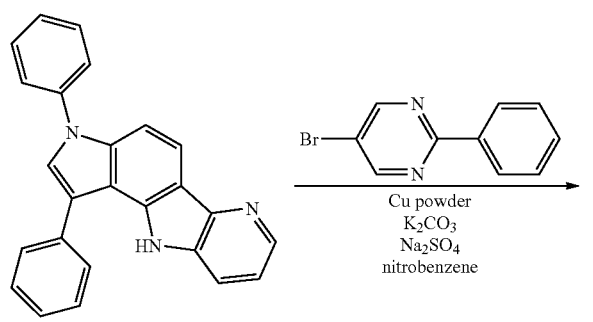

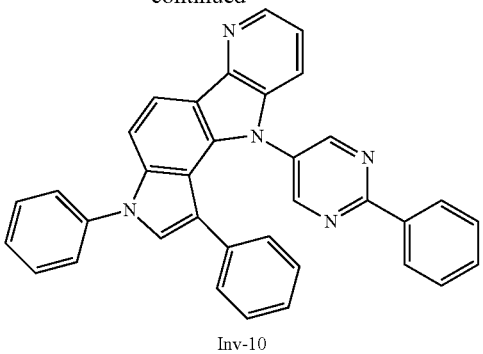

Inv-10

The target compound Inv-10 (3.64 g, yield 51%) was obtained by performing the same procedure as in Synthesis Example 1, except that IC-4 which is the compound prepared in Preparation Example 4 and 5-bromo-2-phenylpyridine were used instead of IC-1 and iodobenzene.

GC-Mass (theoretical value: 513.20 g/mol, measured value: 513 g/mol)

SYNTHESIS EXAMPLE 11

Synthesis of INV-11

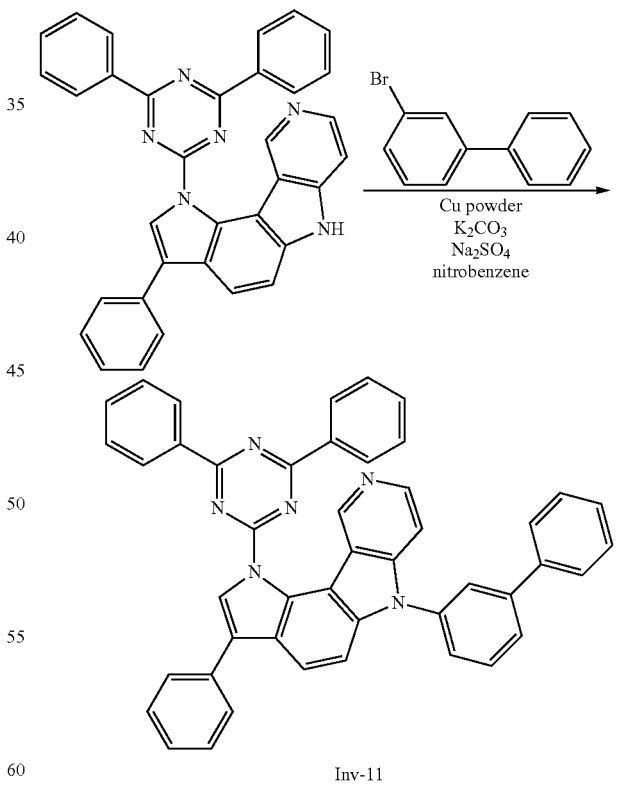

Inv-11

The target compound Inv-11 (4.66 g, yield 72%) was obtained by performing the same procedure as in Synthesis Example 1, except that IC-5 which is the compound prepared in Preparation Example 5 and 3-bromobiphenyl were used instead of IC-1 and iodobenzene.

GC-Mass (theoretical value: 666.25 g/mol, measured value: 666 g/mol)

SYNTHESIS EXAMPLE 12

Synthesis of INV-12

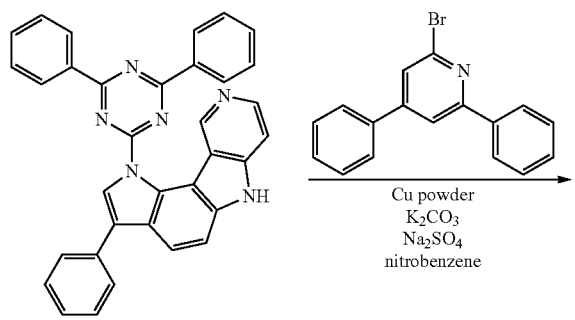

Inv-12

The target compound Inv-12 (4.48 g, yield 62%) was obtained by performing the same procedure as in Synthesis Example 1, except that IC-5 which is the compound prepared in Preparation Example 5 and 2-bromo-4,6-diphenylpyridine were used instead of IC-1 and iodobenzene.

GC-Mass (theoretical value: 743.28 g/mol, measured value: 743 g/mol)

SYNTHESIS EXAMPLE 13

Synthesis of INV-13

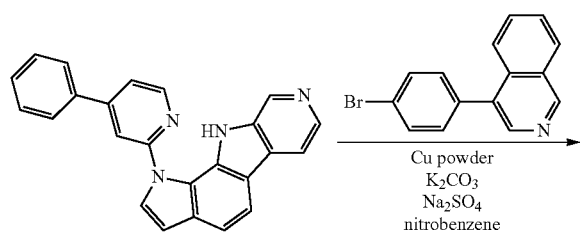

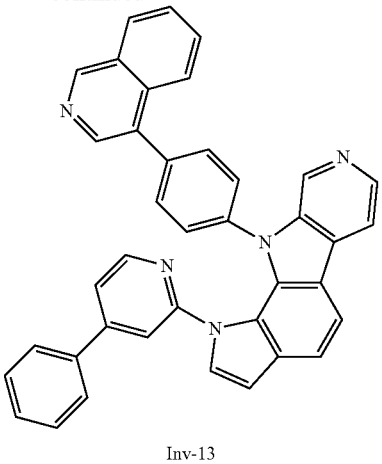

Inv-13

The target compound Inv-13 (4.54 g, yield 58%) was obtained by performing the same procedure as in Synthesis Example 1, except that IC-6 which is the compound prepared in Preparation Example 6 and 4-(4-bromophenyl)isoquinoline were used instead of IC-1 and iodobenzene.

GC-Mass (theoretical value: 563.21 g/mol, measured value: 563 g/mol)

SYNTHESIS EXAMPLE 14

Synthesis of INV-14

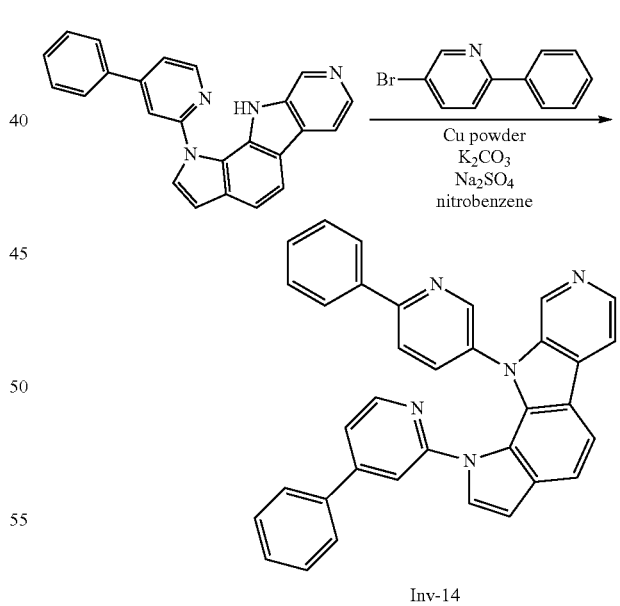

Inv-14

The target compound Inv-14 (3.35 g, yield 47%) was obtained by performing the same procedure as in Synthesis Example 1, except that IC-6 which is the compound prepared in Preparation Example 6 and 5-bromo-2-phenylpyridine were used instead of IC-1 and iodobenzene.

GC-Mass (theoretical value: 513.20 g/mol, measured value: 513 g/mol)

SYNTHESIS EXAMPLE 15

Synthesis of INV-15

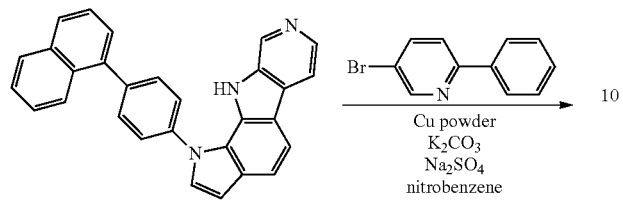

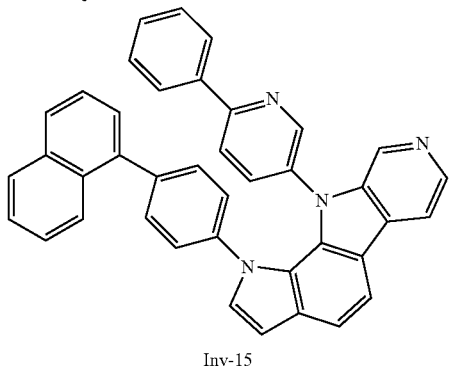

The target compound Inv-15 (3.16 g, yield 46%) was obtained by performing the same procedure as in Synthesis Example 1, except that IC-7 which is the compound prepared in Preparation Example 7 and 5-bromo-2-phenylpyridine were used instead of IC-1 and iodobenzene.

GC-Mass (theoretical value: 562.22 g/mol, measured value: 562 g/mol)

SYNTHESIS EXAMPLE 16

Synthesis of INV-16

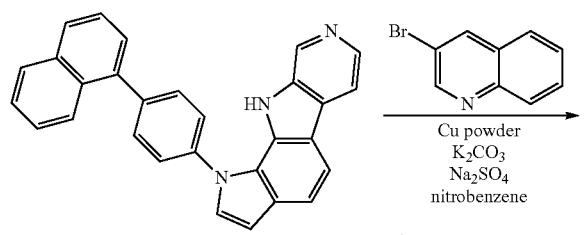

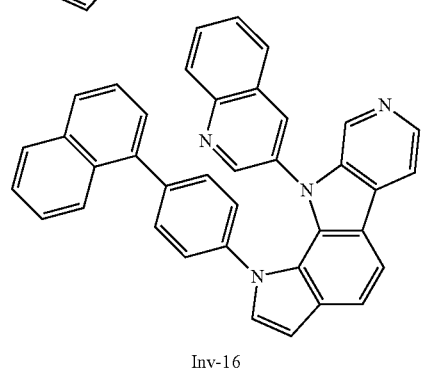

The target compound Inv-16 (4.00 g, yield 61%) was obtained by performing the same procedure as in Synthesis Example 1, except that IC-7 which is the compound prepared in Preparation Example 7 and 3-bromoquinoline were used instead of IC-1 and iodobenzene.

GC-Mass (theoretical value: 536.20 g/mol, measured value: 536 g/mol)

SYNTHESIS EXAMPLE 17

Synthesis of INV-17

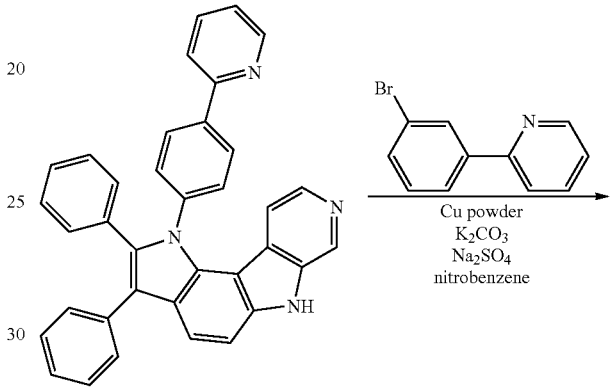

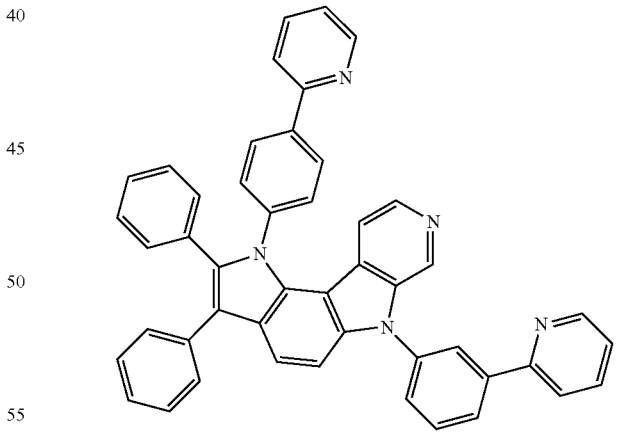

The target compound Inv-17 (4.42 g, yield 68%) was obtained by performing the same procedure as in Synthesis Example 1, except that IC-8 which is the compound prepared in Preparation Example 8 and 2-(3-bromophenyl)pyridine were used instead of IC-1 and iodobenzene.

GC-Mass (theoretical value: 665.26 g/mol, measured value: 665 g/mol)

SYNTHESIS EXAMPLE 18

Synthesis of INV-18

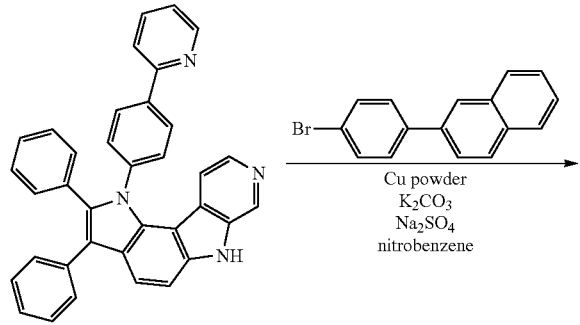

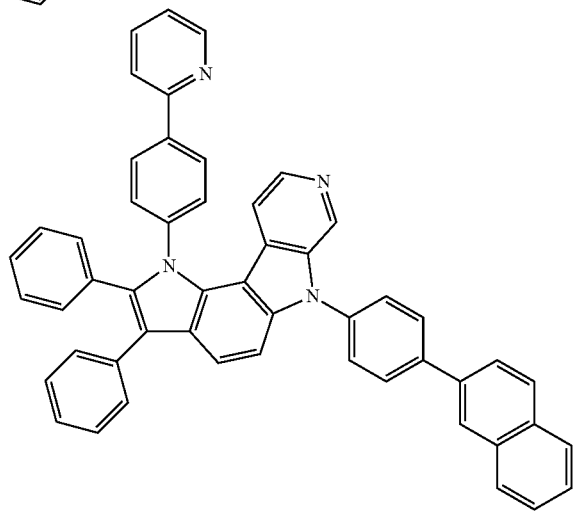

Inv-18

The target compound Inv-18 (3.97 g, yield 57%) was obtained by performing the same procedure as in Synthesis Example 1, except that IC-8 which is the compound prepared in Preparation Example 8 and 2-(4-bromophenyl)naphthalene were used instead of IC-1 and iodobenzene.

GC-Mass (theoretical value: 714.28 g/mol, measured value: 714 g/mol)

SYNTHESIS EXAMPLE 19

Synthesis of INV-19

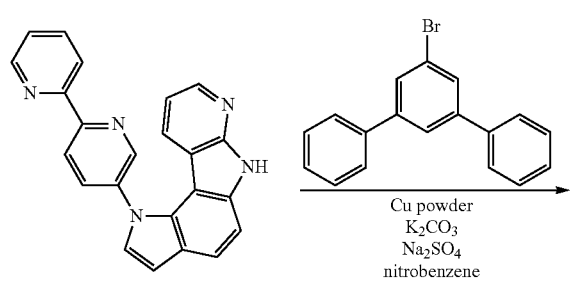

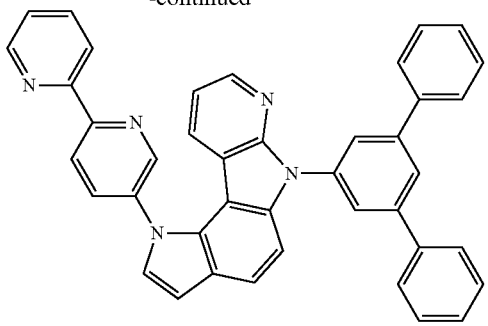

Inv-19

The target compound Inv-19 (5.14 g, yield 63%) was obtained by performing the same procedure as in Synthesis Example 1, except that IC-9 which is the compound prepared in Preparation Example 9 and 1-bromo-3,5-diphenyl benzene were used instead of IC-1 and iodobenzene.

GC-Mass (theoretical value: 589.23 g/mol, measured value: 589 g/mol)

SYNTHESIS EXAMPLE 20

Synthesis of INV-20

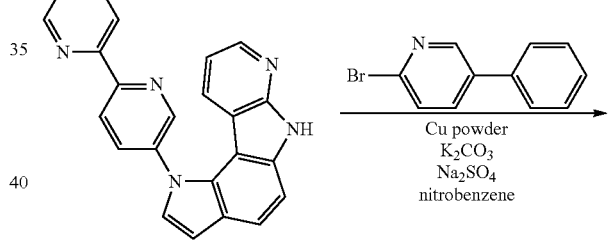

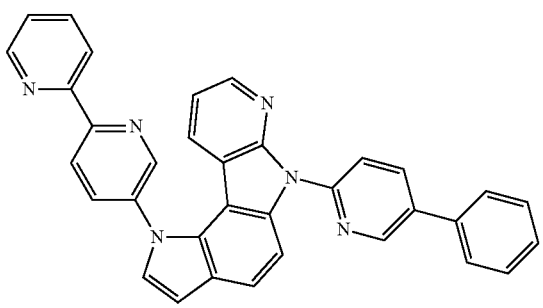

Inv-20

The target compound Inv-20 (4.20 g, yield 59%) was obtained by performing the same procedure as in Synthesis Example 1, except that IC-9 which is the compound prepared in Preparation Example 9 and 2-bromo-5-phenylpyridine were used instead of IC-1 and iodobenzene.

GC-Mass (theoretical value: 514.19 g/mol, measured value: 514 g/mol)

SYNTHESIS EXAMPLE 21

Synthesis of INV-21

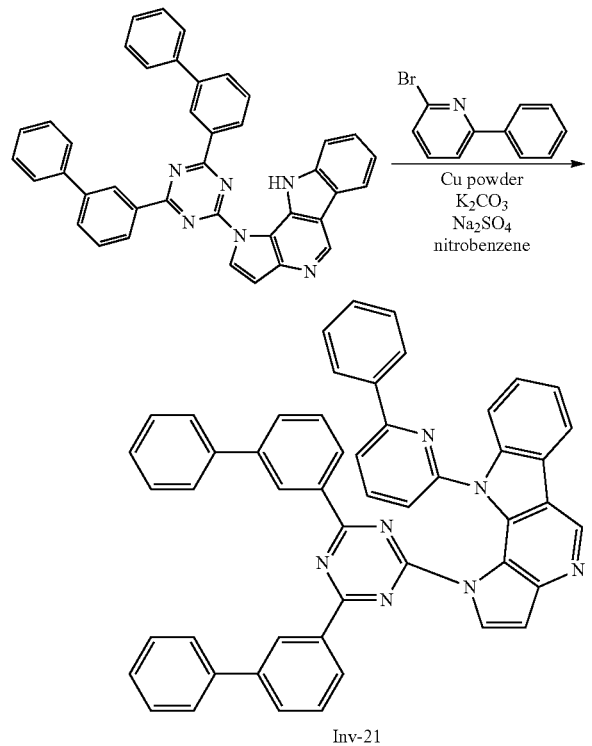

Inv-21

The target compound Inv-21 (4.41 g, yield 70%) was obtained by performing the same procedure as in Synthesis Example 1, except that IC-10 which is the compound prepared in Preparation Example 10 and 2-bromo-6-phenylpyridine were used instead of IC-1 and iodobenzene.

GC-Mass (theoretical value: 743.28 g/mol, measured value: 743 g/mol)

SYNTHESIS EXAMPLE 22

Synthesis of INV-22

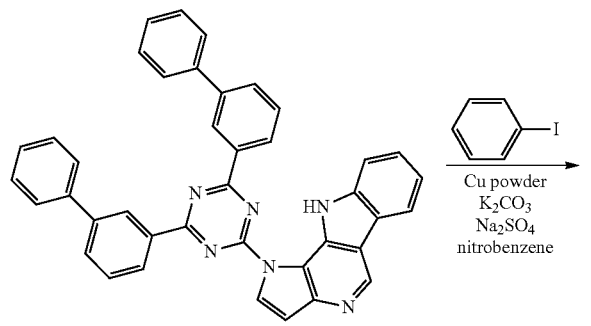

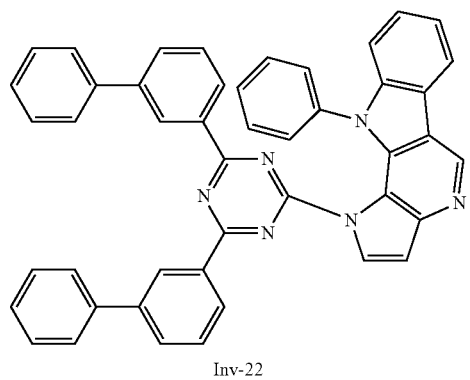

Inv-22

The target compound Inv-22 (4.29 g, yield 76%) was obtained by performing the same procedure as in Synthesis Example 1, except that IC-10 which is the compound prepared in Preparation Example 10 was used instead of IC-1.

GC-Mass (theoretical value: 666.25 g/mol, measured value: 666 g/mol)

SYNTHESIS EXAMPLE 23

Synthesis of INV-23

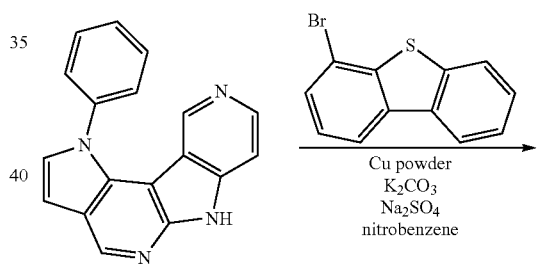

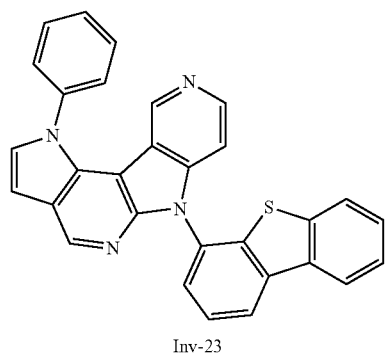

Inv-23

The target compound Inv-23 (5.42 g, yield 66%) was obtained by performing the same procedure as in Synthesis Example 1, except that IC-11 which is the compound prepared in Preparation Example 11 and 4-bromodibenzo[b,d]thiophene were used instead of IC-1 and iodobenzene.

GC-Mass (theoretical value: 466.13 g/mol, measured value: 466 g/mol)

SYNTHESIS EXAMPLE 24

Synthesis of INV-24

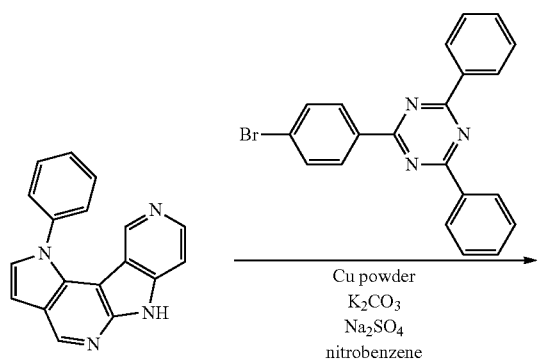

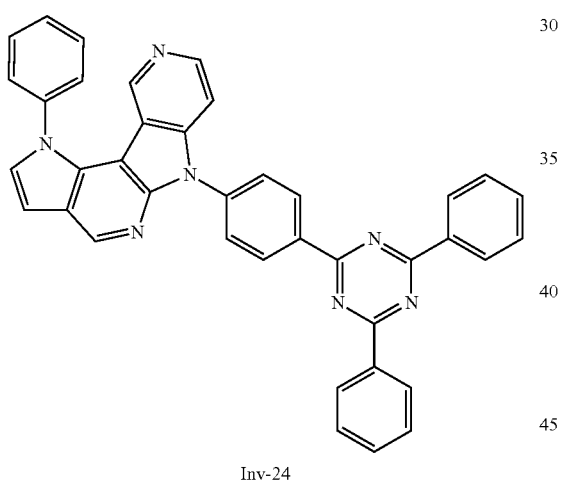

Inv-24

The target compound Inv-24 (7.18 g, yield 69%) was obtained by performing the same procedure as in Synthesis Example 1, except that IC-11 which is the compound prepared in Preparation Example 11 and 2-(4-bromophenyl)-4,6-diphenyl-1,3,5-triazine were used instead of IC-1 and iodobenzene.

GC-Mass (theoretical value: 591.22 g/mol, measured value: 591 g/mol)

SYNTHESIS EXAMPLE 25

Synthesis of INV-25

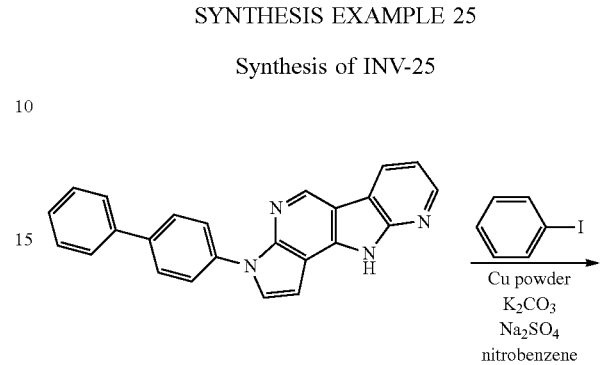

Inv-25

The target compound Inv-25 (4.54 g, yield 75%) was obtained by performing the same procedure as in Synthesis Example 1, except that IC-12 which is the compound prepared in Preparation Example 12 was used instead of IC-1.

GC-Mass (theoretical value: 436.17 g/mol, measured value: 436 g/mol)

SYNTHESIS EXAMPLE 26

Synthesis of INV-26

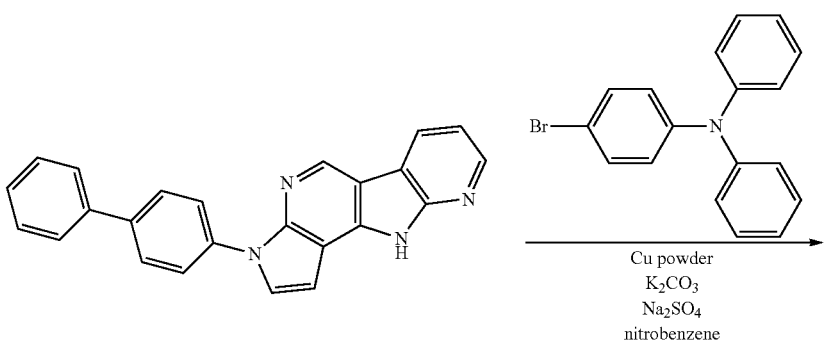

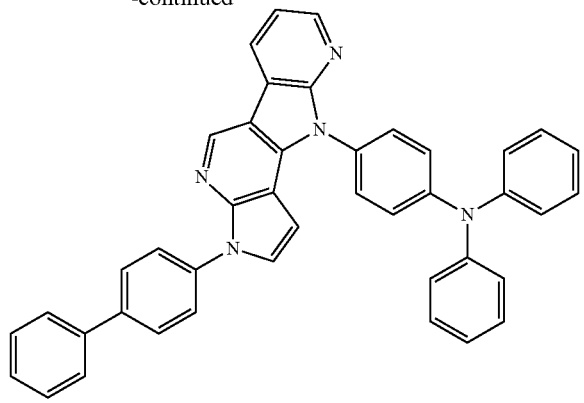

Inv-26

The target compound Inv-26 (4.61 g, yield 55%) was obtained by performing the same procedure as in Synthesis Example 1, except that IC-12 which is the compound prepared in Preparation Example 12 and 4-bromo-N,N-diphenylaniline were used instead of IC-1 and iodobenzene.

GC-Mass (theoretical value: 603.24 g/mol, measured value: 603 g/mol)

SYNTHESIS EXAMPLE 27

Synthesis of INV-27

The target compound Inv-27 (4.32 g, yield 63%) was obtained by performing the same procedure as in Synthesis Example 1, except that IC-13 which is the compound prepared in Preparation Example 13 and 3-(4-bromophenyl)pyridine were used instead of IC-1 and iodobenzene.

GC-Mass (theoretical value: 564.21 g/mol, measured value: 564 g/mol)

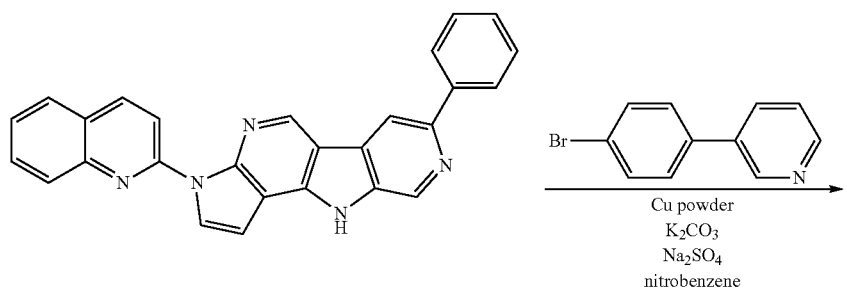

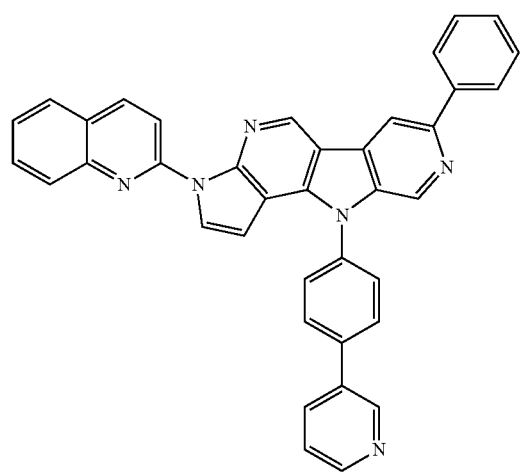

Inv-27

SYNTHESIS EXAMPLE 28

Synthesis of INV-28

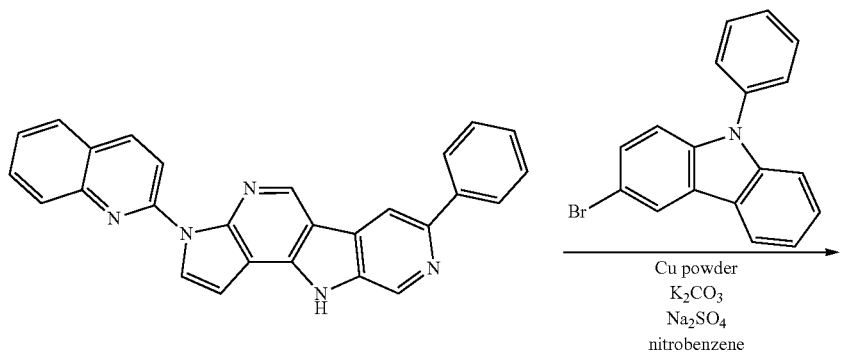

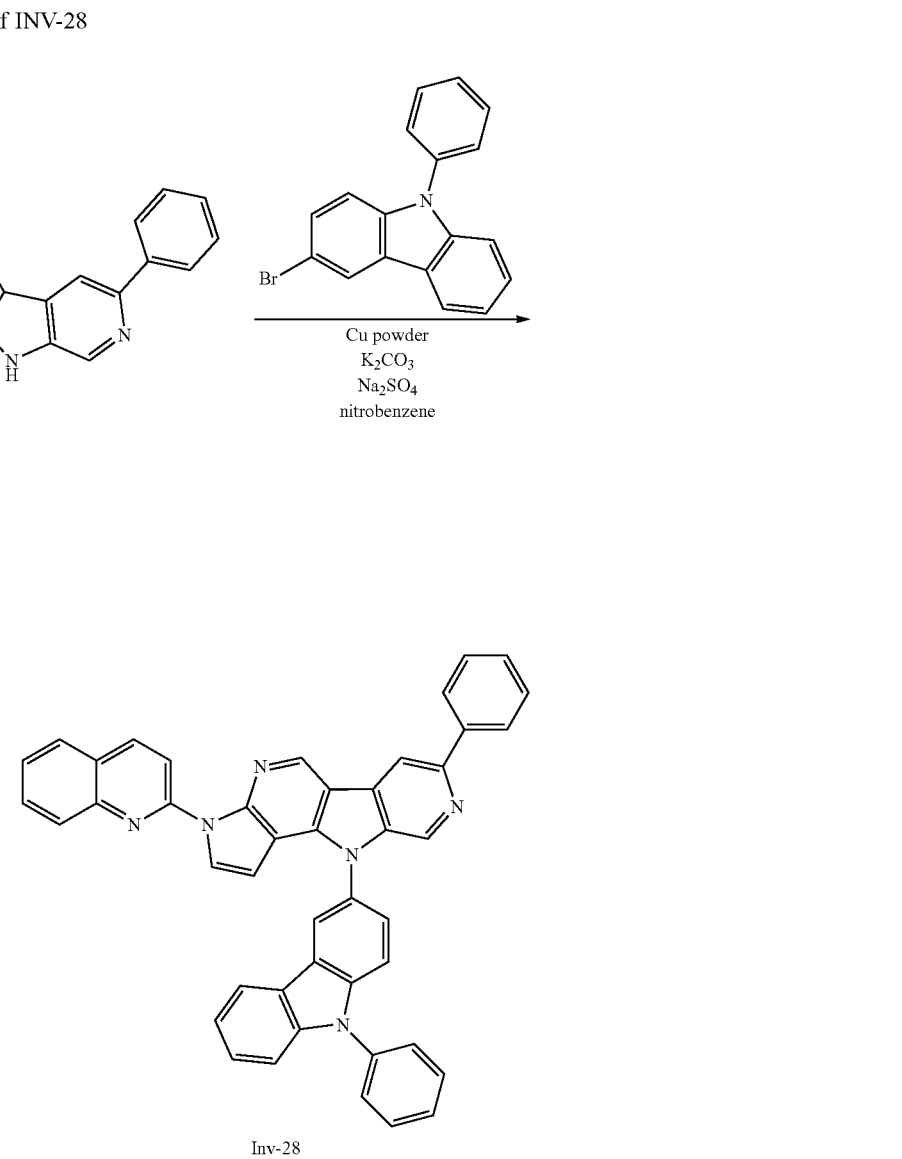

The target compound Inv-28 (5.16 g, yield 65%) was obtained by performing the same procedure as in Synthesis Example 1, except that IC-13 which is the compound prepared in Preparation Example 13 and 3-bromo-9-phenyl-9H-carbazole were used instead of IC-1 and iodobenzene.

GC-Mass (theoretical value: 652.24 g/mol, measured value: 652 g/mol)

SYNTHESIS EXAMPLE 29

Synthesis of INV-29

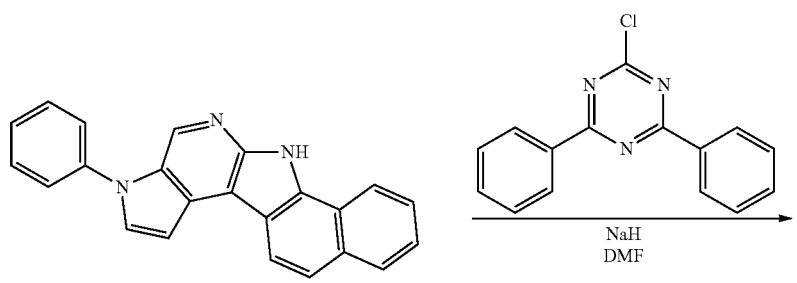

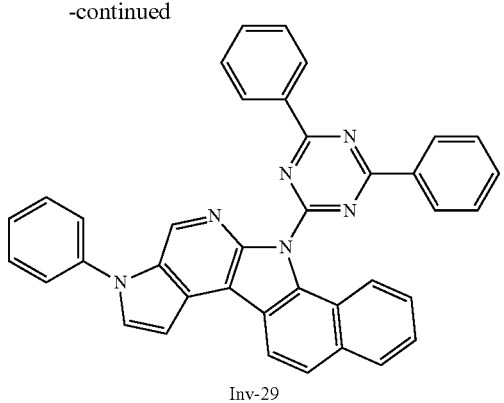

Inv-29

The target compound Inv-29 (6.86 g, yield 81%) was obtained by performing the same procedure as in Synthesis Example 2, except that IC-14 which is the compound prepared in Preparation Example 14 was used instead of IC-1.

GC-Mass (theoretical value: 564.21 g/mol, measured value: 564 g/mol)

SYNTHESIS EXAMPLE 30

Synthesis of INV-30

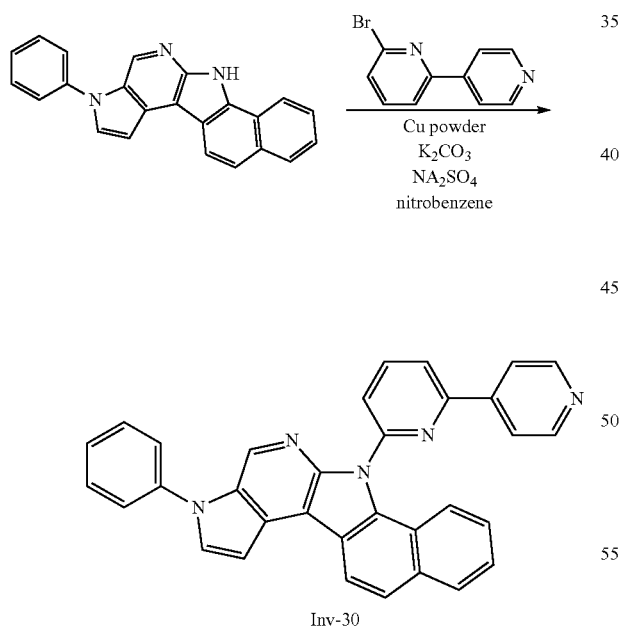

Inv-30

The target compound Inv-30 (4.24 g, yield 58%) was obtained by performing the same procedure as in Synthesis Example 1, except that IC-14 which is the compound prepared in Preparation Example 14 and 6-bromo-2,4'-bipyridine were used instead of IC-1 and iodobenzene.

GC-Mass (theoretical value: 487.18 g/mol, measured value: 487 g/mol)

SYNTHESIS EXAMPLE 31

Synthesis of INV-31

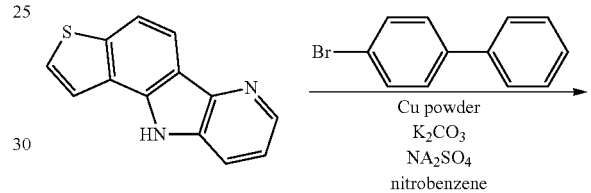

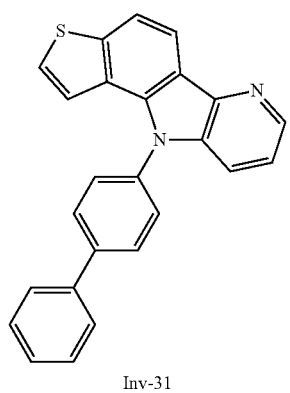

Inv-31

The target compound Inv-31 (4.03 g, yield 48%) was obtained by performing the same procedure as in Synthesis Example 1, except that IC-15 which is the compound prepared in Preparation Example 15 and 4-bromobiphenyl were used instead of IC-1 and iodobenzene.

GC-Mass (theoretical value: 376.10 g/mol, measured value: 376 g/mol)

SYNTHESIS EXAMPLE 32

Synthesis of INV-32

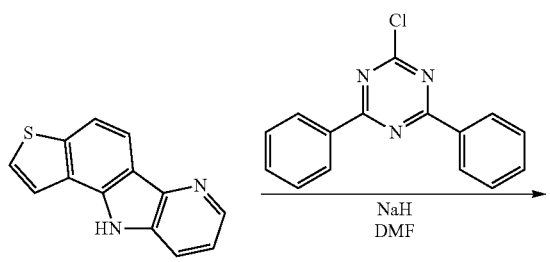

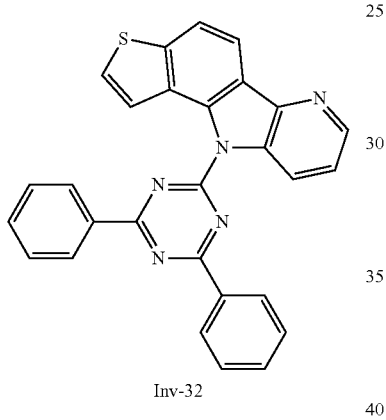

Inv-32

The target compound Inv-32 (7.92 g, yield 78%) was obtained by performing the same procedure as in Synthesis Example 2, except that IC-15 which is the compound prepared in Preparation Example 15 was used instead of IC-1.

GC-Mass (theoretical value: 455.12 g/mol, measured value: 455 g/mol)

SYNTHESIS EXAMPLE 33

Synthesis of INV-33

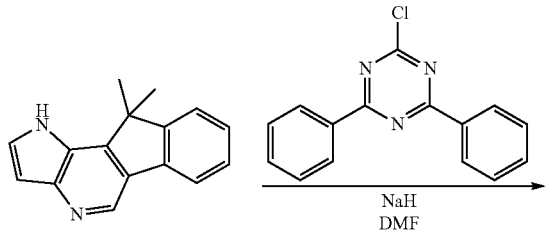

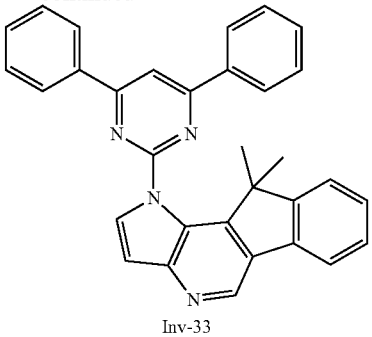

Inv-33

The target compound Inv-33 (6.34 g, yield 64%) was obtained by performing the same procedure as in Synthesis Example 2, except that IC-16 which is the compound prepared in Preparation Example 16 and 2-chloro-4,6-diphenylpyrimidine were used instead of IC-1 and 2-chloro-4,6-diphenyl-1,3,5-triazine.

GC-Mass (theoretical value: 464.20 g/mol, measured value: 464 g/mol)

SYNTHESIS EXAMPLE 34

Synthesis of INV-34

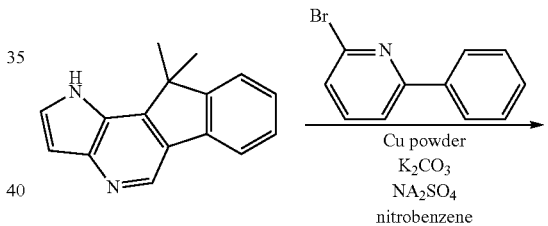

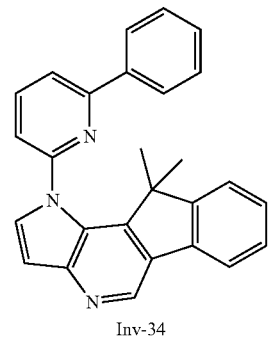

Inv-34

The target compound Inv-34 (4.88 g, yield 59%) was obtained by performing the same procedure as in Synthesis Example 1, except that IC-16 which is the compound prepared in Preparation Example 16 and 2-bromo-6-phenylpyridine were used instead of IC-1 and iodobenzene.

GC-Mass (theoretical value: 387.17 g/mol, measured value: 387 g/mol)

SYNTHESIS EXAMPLE 35

Synthesis of INV-35

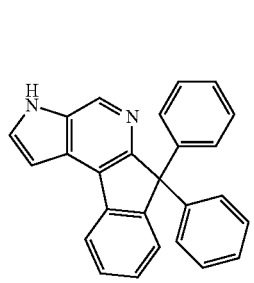 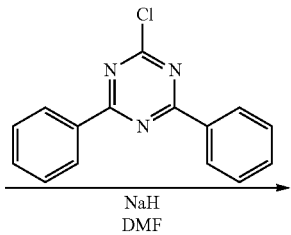

NaH
DMF

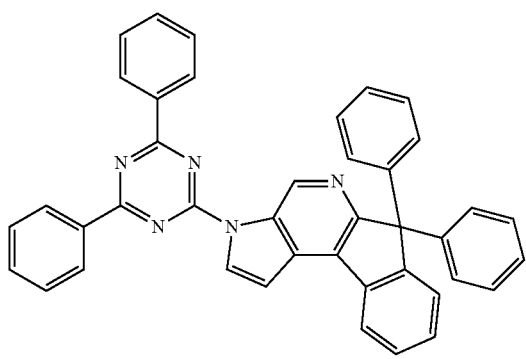

Inv-35

The target compound Inv-35 (6.00 g, yield 73%) was obtained by performing the same procedure as in Synthesis Example 2, except that IC-17 which is the compound prepared in Preparation Example 17 was used instead of IC-1.

GC-Mass (theoretical value: 589.23 g/mol, measured value: 589 g/mol)

SYNTHESIS EXAMPLE 36

Synthesis of INV-36

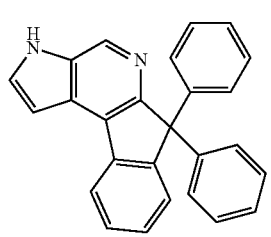 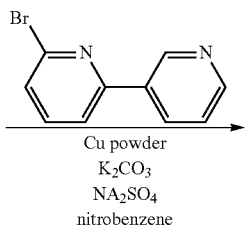

Cu powder
K$_2$CO$_3$
NA$_2$SO$_4$
nitrobenzene

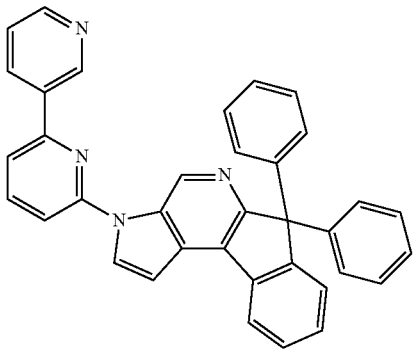

Inv-36

The target compound Inv-36 (4.43 g, yield 62%) was obtained by performing the same procedure as in Synthesis Example 1, except that IC-17 which is the compound prepared in Preparation Example 17 and 6-bromo-2,3'-bipyridine were used instead of IC-1 and iodobenzene.

GC-Mass (theoretical value: 512.20 g/mol, measured value: 512 g/mol)

EXAMPLES 1 to 36

Manufacture of Organic El Device

Inv-1 to Inv-36, which are the compounds synthesized in Synthesis Examples 1 to 36, were subjected to highly-pure sublimation purification by a typically known method, and then green organic EL devices were manufactured according to the following procedure.

First, a glass substrate thinly coated with indium tin oxide (ITO) to have a thickness of 1,500 Å was ultrasonically washed with distilled water. When the ultrasonic washing with distilled water was completed, the substrate was ultrasonically washed with a solvent such as isopropyl alcohol, acetone, and methanol, dried, transferred to a UV ozone cleaner (Power sonic 405, manufactured by Hwashin Tech), washed for 5 minutes by using UV, and then transferred to a vacuum evaporator.

An organic EL device was manufactured by laminating m-MTDATA (60 nm)/TCTA (80 nm)/each compound of Inv-1 to Inv-36+10% Ir(ppy)$_3$ (300 nm)/BCP (10 nm)/Alq$_3$ (30 nm)/LiF (1 nm)/Al (200 nm) in this order on the thus prepared ITO transparent electrode.

The structures of m-MTDATA, TCTA, Ir(ppy)$_3$, CBP, and BCP are as follows.

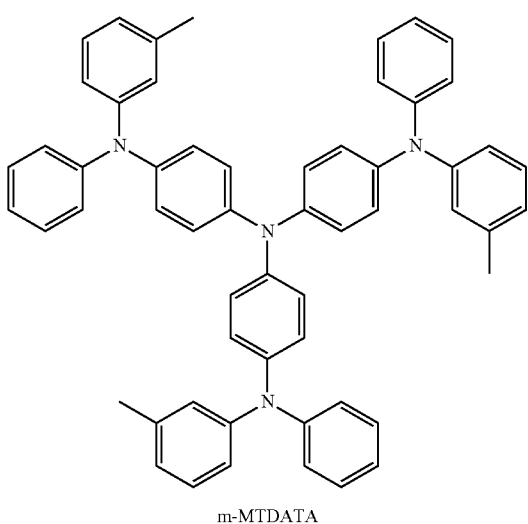

m-MTDATA

TCTA

Ir(ppy)₃

CBP

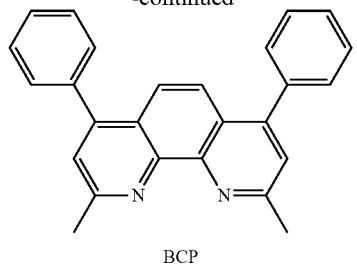

BCP

COMPARATIVE EXAMPLE 1

Manufacture of Organic El Device

An organic EL device was manufactured by the same procedure as in Example 1, except that when a light-emitting layer is formed, CBP was used as a light-emitting host material instead of Compound Inv-1.

EVALUATION EXAMPLE

For each of the organic EL devices manufactured in Examples 1 to 36 and Comparative Example 1, the driving voltage, current efficiency, and light-emitting peaks thereof were measured at a current density of 10 mA/cm², and the results are shown in the following Table 1.

TABLE 1

| Sample | Host | Driving voltage (V) | EL peak (nm) | Current efficiency (cd/A) |
|---|---|---|---|---|
| Example 1 | Inv-1 | 6.78 | 517 | 41.4 |
| Example 2 | Inv-2 | 6.61 | 516 | 41.3 |
| Example 3 | Inv-3 | 6.63 | 516 | 40.5 |
| Example 4 | Inv-4 | 6.61 | 515 | 41.2 |
| Example 5 | Inv-5 | 6.61 | 517 | 40.6 |
| Example 6 | Inv-6 | 6.77 | 516 | 42.0 |
| Example 7 | Inv-7 | 6.78 | 51 | 40.5 |
| Example 8 | Inv-8 | 6.60 | 516 | 41.2 |
| Example 9 | Inv-9 | 6.79 | 517 | 41.3 |
| Example 10 | Inv-10 | 6.65 | 516 | 40.2 |
| Example 11 | Inv-11 | 6.77 | 515 | 41.1 |
| Example 12 | Inv-12 | 6.79 | 518 | 41.3 |
| Example 13 | Inv-13 | 6.62 | 517 | 40.2 |
| Example 14 | Inv-14 | 6.63 | 518 | 40.5 |
| Example 15 | Inv-15 | 6.61 | 516 | 41.2 |
| Example 16 | Inv-16 | 6.79 | 516 | 41.3 |
| Example 17 | Inv-17 | 6.67 | 517 | 39.5 |
| Example 18 | Inv-18 | 6.66 | 515 | 39.6 |
| Example 19 | Inv-19 | 6.69 | 518 | 39.3 |
| Example 20 | Inv-20 | 6.65 | 517 | 39.8 |
| Example 21 | Inv-21 | 6.66 | 518 | 40.2 |
| Example 22 | Inv-22 | 6.72 | 518 | 39.5 |
| Example 23 | Inv-23 | 6.60 | 519 | 39.2 |
| Example 24 | Inv-24 | 6.63 | 516 | 39.1 |
| Example 25 | Inv-25 | 6.69 | 517 | 39.9 |
| Example 26 | Inv-26 | 6.51 | 515 | 40.1 |
| Example 27 | Inv-27 | 6.59 | 517 | 39.5 |
| Example 28 | Inv-28 | 6.51 | 518 | 39.9 |
| Example 29 | Inv-29 | 6.72 | 517 | 39.1 |
| Example 30 | Inv-30 | 6.66 | 516 | 40.2 |
| Example 31 | Inv-31 | 6.77 | 515 | 40.0 |
| Example 32 | Inv-32 | 6.78 | 516 | 40.3 |
| Example 33 | Inv-33 | 6.62 | 517 | 41.2 |
| Example 34 | Inv-34 | 6.63 | 516 | 42.3 |
| Example 35 | Inv-35 | 6.61 | 518 | 40.7 |
| Example 36 | Inv-36 | 6.70 | 517 | 41.3 |
| Comparative Example 1 | CBP | 6.93 | 516 | 38.2 |

As shown in Table 1, it can be seen that the organic EL devices of Examples 1 to 36 in which the compounds (Inv-1 to Inv-36) according to the present disclosure are used as a light-emitting layer of a green organic EL device exhibit much better performance in terms of efficiency and driving voltage than the green organic EL device of Comparative Example 1 in the related art in which the CBP is used.

The invention claimed is:

1. A compound of the following Formula 1:

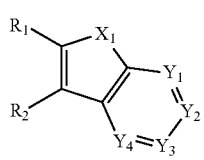

Formula 1 wherein $Y_1$ to $Y_4$ are the same as or different from each other, and are each independently selected from N and $CR_3$, and at least one of $Y_1$ and $Y_2$, $Y_2$ and $Y_3$, or $Y_3$ and $Y_4$ is $CR_3$, and forms a fused ring represented by the following Formula 2;

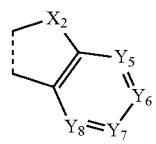

Formula 2 wherein the dotted line means a site where a fusion with the compound of Formula 1 occurs;

$Y_5$ to $Y_8$ are the same as or different from each other, and are each independently selected from N and $CR_4$, with a proviso that $Y_1$ to $Y_8$ include at least one N, and $X_1$ and $X_2$ are the same as or different from each other, and are each independently selected from O, S, Se, $N(Ar_1)$, $C(Ar_2)(Ar_3)$, and $Si(Ar_4)(Ar_5)$, and here, at least one of $X_1$ and $X_2$ is $N(Ar_1)$, and $R_1$ and $R_2$ are the same as or different from each other, and are each independently selected from the group consisting of hydrogen, a substitute or unsubstituted $C_6$ to $C_{60}$ aryl group, and a substituted or unsubstituted heteroaryl group having 5 to 60 nuclear atoms, and $R_3$ to $R_4$ are the same as or different from each other, and are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these form or do not form a fused ring with an adjacent group;

$Ar_1$ to $Ar_5$ are the same as or different from each other, and are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and the $C_1$ to $C_{40}$ alkyl group, the $C_3$ to $C_{40}$ cycloalkyl group, the heterocycloalkyl group having 3 to 40 nuclear atoms, the $C_6$ to $C_{60}$ aryl group, the heteroaryl group having 5 to 60 nuclear atoms, the $C_1$ to $C_{40}$ alkyloxy group, the $C_6$ to $C_{60}$ aryloxy group, the $C_1$ to $C_{40}$ alkylsilyl group, the $C_6$ to $C_{60}$ arylsilyl group, the $C_1$ to $C_{40}$ alkyl boron group, the $C_6$ to $C_{60}$ aryl boron group, the $C_6$ to $C_{60}$ arylphosphine group, the $C_6$ to $C_{60}$ arylphosphine oxide group, and the $C_6$ to $C_{60}$ arylamine group are optionally each independently substituted with one or more substituents selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group.

2. The compound of claim 1, wherein the compound of Formula 1 is represented by any one of the following Formulae 3 to 8:

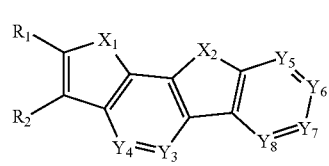

Formula 3

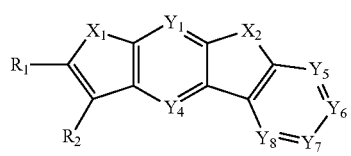

Formula 4

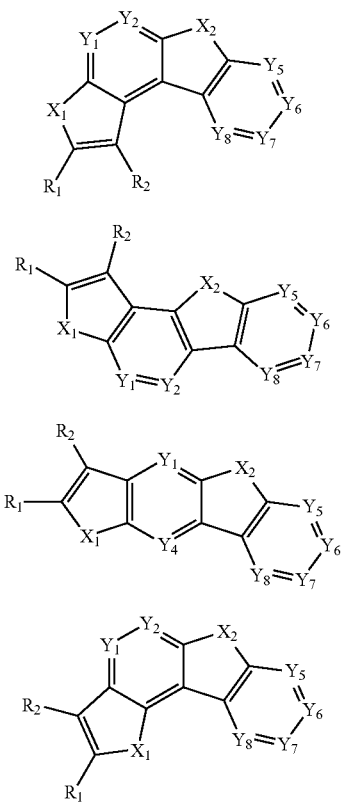

Formula 5

Formula 6

Formula 7

Formula 8 wherein $X_1$ and $X_2$, $Y_1$ to $Y_8$, $R_1$, and $R_2$ are the same as those defined in claim 1.

3. The compound of claim 2, wherein both $X_1$ and $X_2$ are $N(Ar_1)$.

4. The compound of claim 2, wherein $Y_1$ to $Y_8$ comprise one N.

5. The compound of claim 1, wherein $Ar_1$ to $Ar_5$ are each independently selected from the group consisting of a $C_6$ to $C_{60}$ aryl group, a heteroaryl group having 5 to 60 nuclear atoms, and a $C_6$ to $C_{60}$ arylamine group; and the $C_6$ to $C_{60}$ aryl group, the heteroaryl group having 5 to 60 nuclear atoms, and the $C_6$ to $C_{60}$ arylamine group are each unsubstituted or substituted with one or more functional groups selected from the group consisting of a $C_1$ to $C_{40}$ alkyl group, a $C_6$ to $C_{60}$ aryl group, and a heteroaryl group having 5 to 60 nuclear atoms.

6. The compound of claim 1, wherein $Ar_1$ to $Ar_5$ are selected from the group of the following substituents:

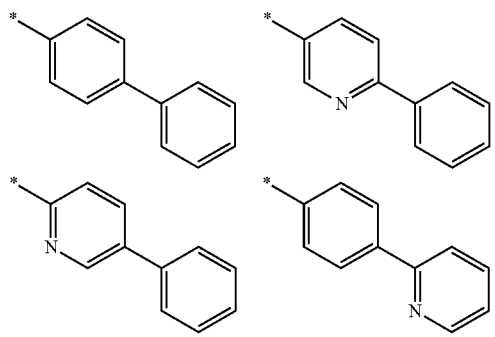

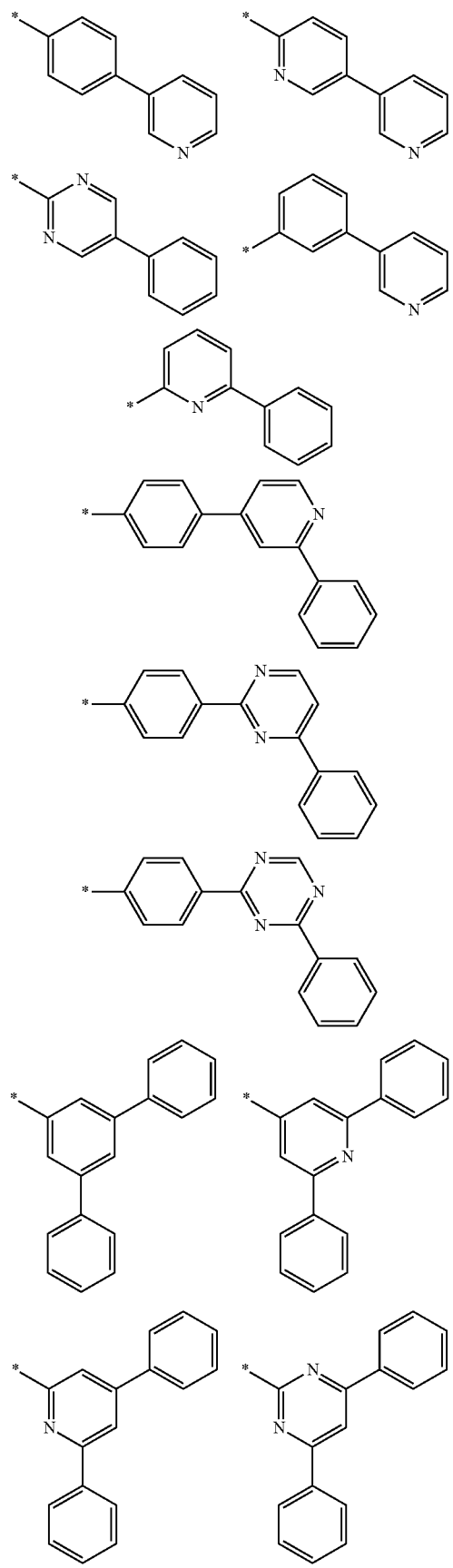

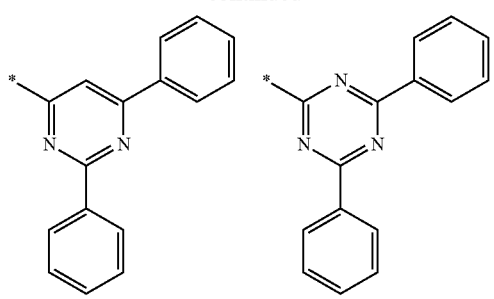
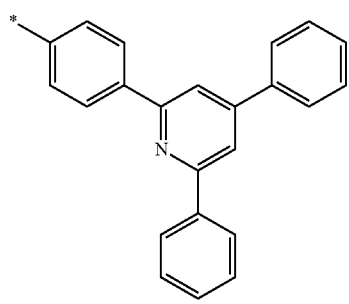
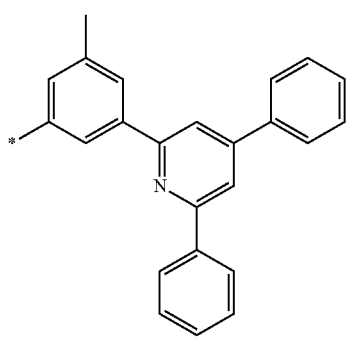
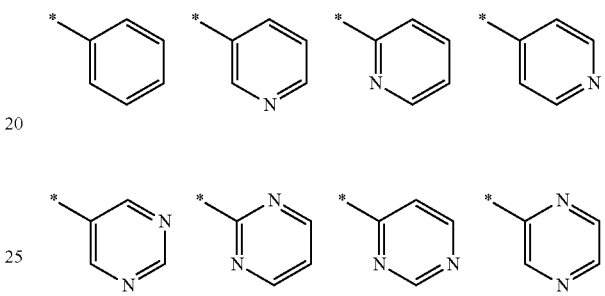
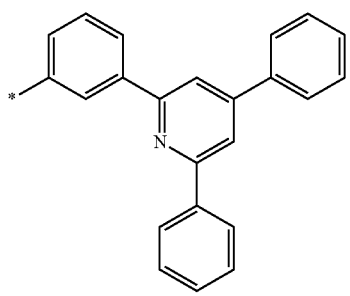
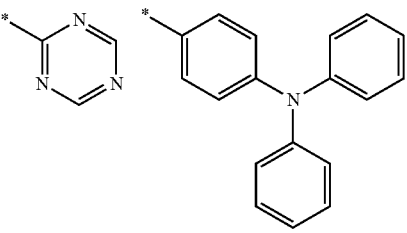
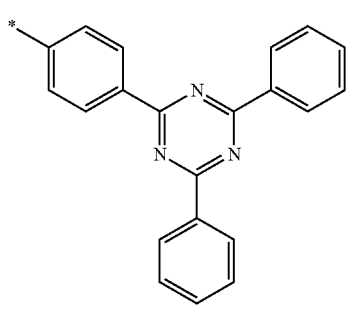
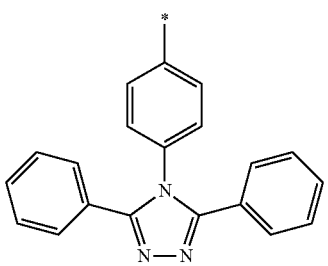
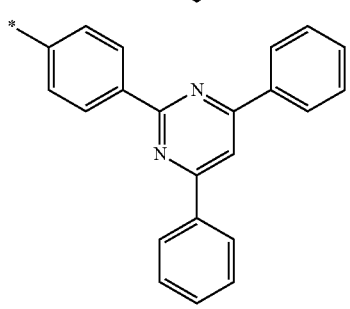
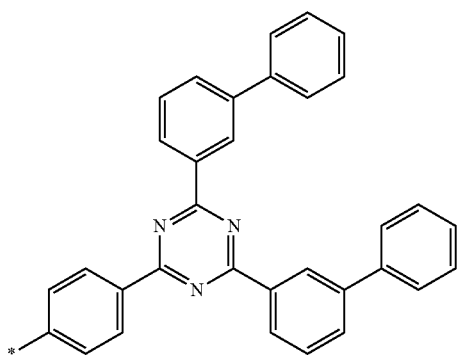
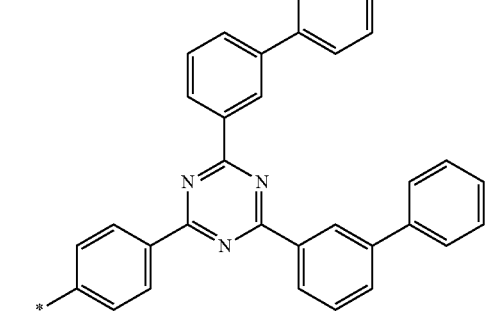

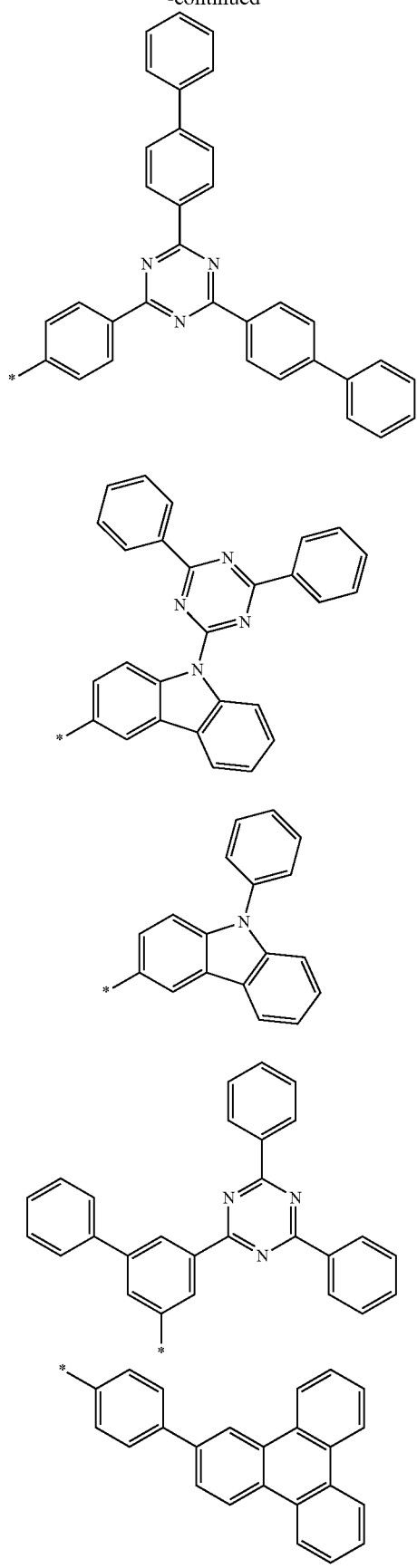
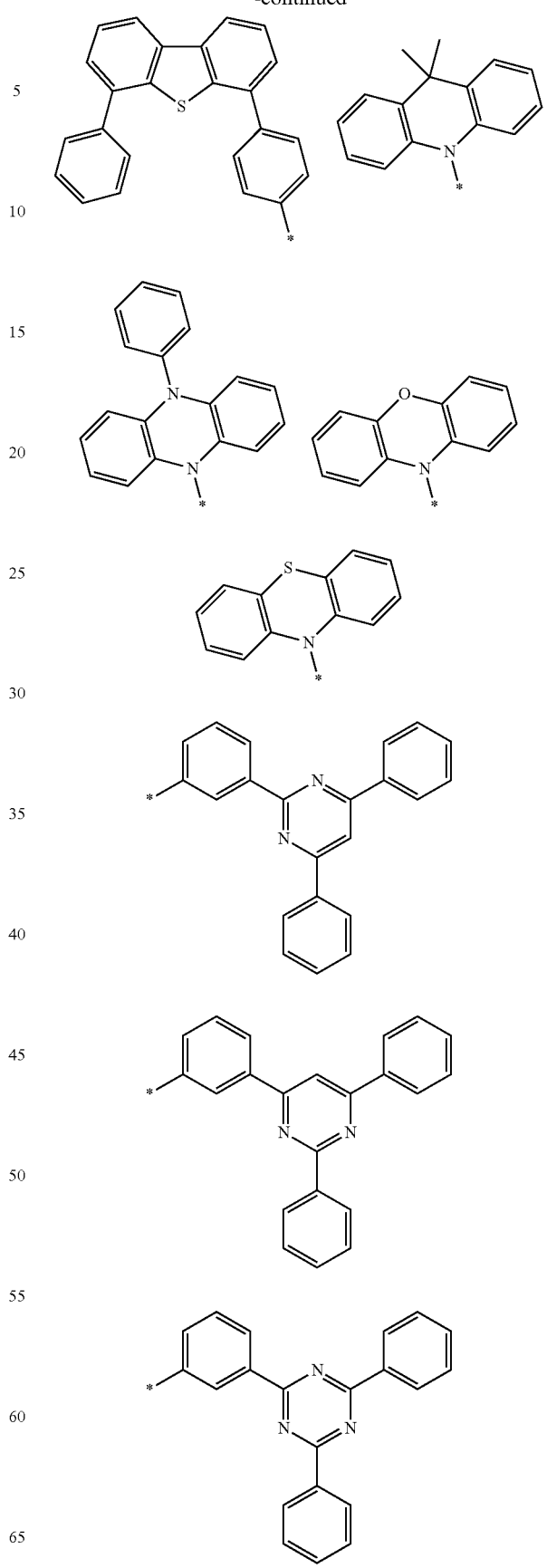

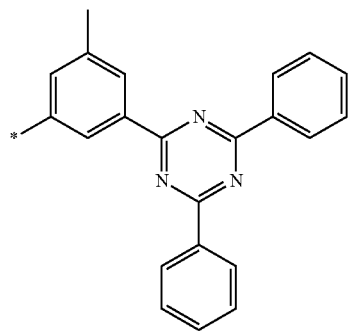

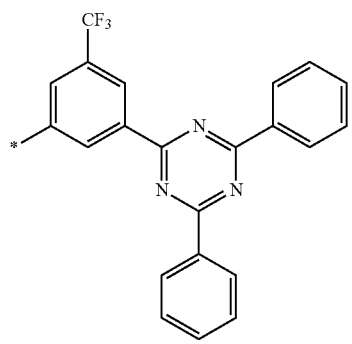

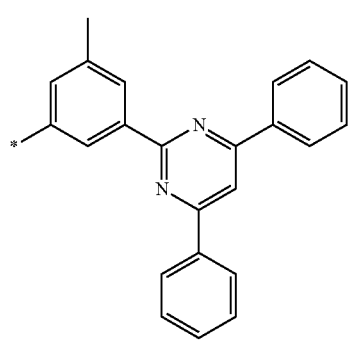

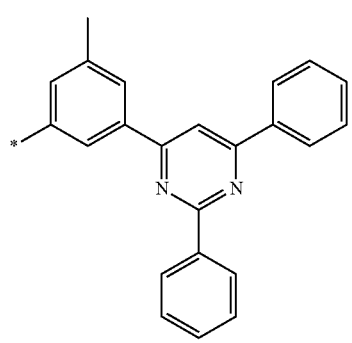

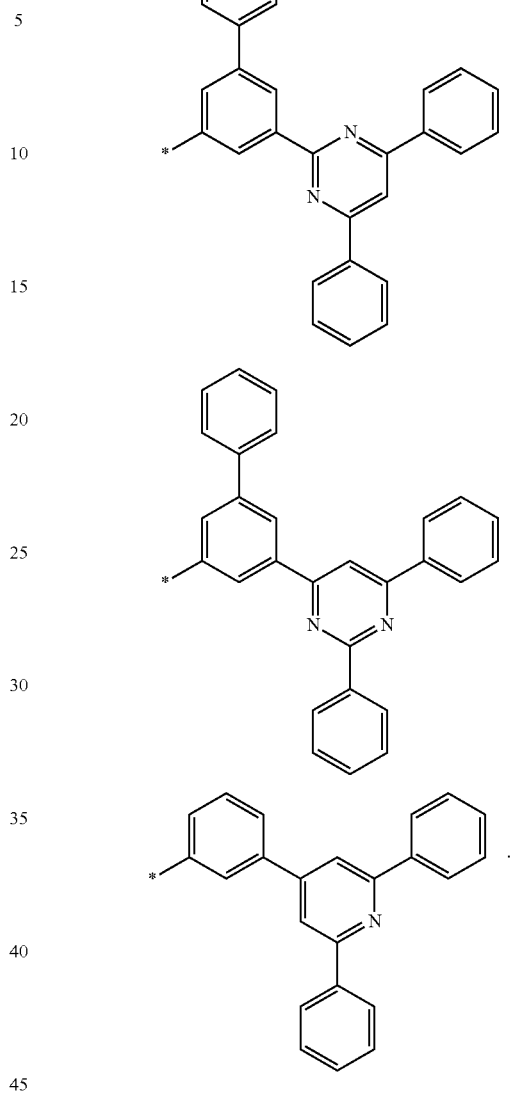

7. An organic electroluminescent device comprising:
   (i) an anode;
   (ii) a cathode; and
   (iii) an organic material layer comprising one or more layers interposed between the anode and the cathode,
   wherein at least one of the organic material layer comprises the compound of claim 1.

8. The organic electroluminescent device of claim 7, wherein the organic material layer comprising the compound is selected from the group consisting of a hole injection layer, a hole transporting layer, and a light-emitting layer.

9. The organic electroluminescent device of claim 7, wherein the compound is used as a phosphorescent host of a light-emitting layer.

10. The organic electroluminescent device of claim 7, wherein the compound is represented by any one of the following Formulae 3 to 8:

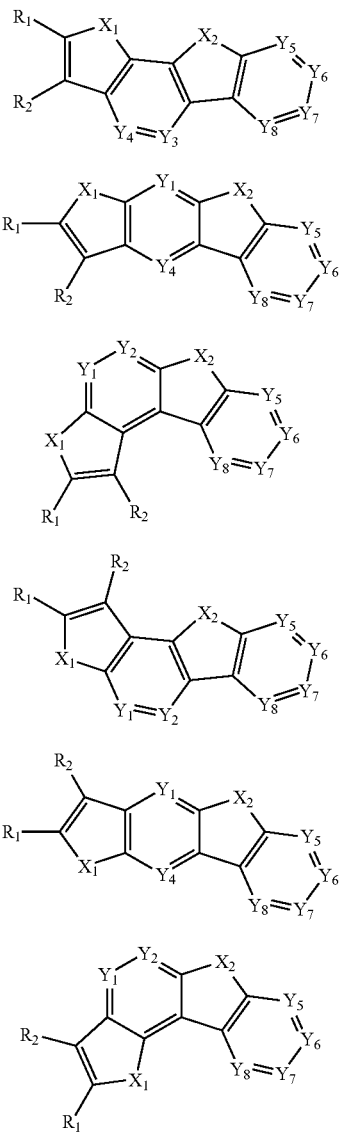

Formula 3

Formula 4

Formula 5

Formula 6

Formula 7

Formula 8 wherein $X_1$ and $X_2$ are the same as or different from each other, and are each independently selected from the group consisting of O, S, Se, $N(Ar_1)$, $C(Ar_2)(Ar_3)$, and $Si(Ar_4)(Ar_5)$, and at least one of $X_1$ and $X_2$ is $N(Ar_1)$, and $Y_1$ to $Y_4$ are the same as or different from each other, and are each independently selected from N and $CR_3$, and $Y_5$ to $Y_8$ are the same as or different from each other, and are each independently selected from N and $CR_4$, with a proviso that $Y_1$ to $Y_8$ include at least one N, and $R_1$ and $R_2$ are the same as or different from each other, and are each independently selected from the group consisting of hydrogen, a substituted or unsubstituted $C_6$ to $C_{60}$ aryl group, and a substituted or unsubstituted heteroaryl group having 5 to 60 nuclear atoms, and $R_3$ to $R_4$ are the same as or different from each other, and are each independently selected from the group consisting of hydrogen, deuterium, halogen, cyano, a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and these form or do not form a fused ring with an adjacent group;

$Ar_1$ to $Ar_5$ are the same as or different from each other, and are each independently selected from the group consisting of a substituted or unsubstituted $C_1$ to $C_{40}$ alkyl group, a substituted or unsubstituted $C_3$ to $C_{40}$ cycloalkyl group, a substituted or unsubstituted heterocycloalkyl group having 3 to 40 nuclear atoms, a substituted or unsubstituted $C_6$ to $C_{60}$ aryl group, a substituted or unsubstituted heteroaryl group having 5 to 60 nuclear atoms, a substituted or unsubstituted $C_1$ to $C_{40}$ alkyloxy group, a substituted or unsubstituted $C_6$ to $C_{60}$ aryloxy group, a substituted or unsubstituted $C_1$ to $C_{40}$ alkylsilyl group, a substituted or unsubstituted $C_6$ to $C_{60}$ arylsilyl group, a substituted or unsubstituted $C_1$ to $C_{40}$ alkyl boron group, a substituted or unsubstituted $C_6$ to $C_{60}$ aryl boron group, a substituted or unsubstituted $C_6$ to $C_{60}$ arylphosphine group, a substituted or unsubstituted $C_6$ to $C_{60}$ arylphosphine oxide group, and a substituted or unsubstituted $C_6$ to $C_{60}$ arylamine group, and the $C_1$ to $C_{40}$ alkyl group, the $C_3$ to $C_{40}$ cycloalkyl group, the heterocycloalkyl group having 3 to 40 nuclear atoms, the $C_6$ to $C_{60}$ aryl group, the heteroaryl group having 5 to 60 nuclear atoms, the $C_1$ to $C_{40}$ alkyloxy group, the $C_6$ to $C_{60}$ aryloxy group, the $C_1$ to $C_{40}$ alkylsilyl group, the $C_6$ to $C_{60}$ arylsilyl group, the $C_1$ to $C_{40}$ alkyl boron group, the $C_6$ to $C_{60}$ aryl boron group, the $C_6$ to $C_{60}$ arylphosphine group, the $C_6$ to $C_{60}$ arylphosphine oxide group, and the $C_6$ to $C_{60}$ arylamine group are optionally each independently substituted with one or more substituents selected from the group consisting of hydrogen, deuterium, halogen, cyano, a $C_1$ to $C_{40}$ alkyl group, a $C_3$ to $C_{40}$ cycloalkyl group, a heterocycloalkyl group having 3 to 40 nuclear atoms, a $C_6$ to $C_{60}$ aryl group, a heteroaryl group having 5 to 60 nuclear atoms, a $C_1$ to $C_{40}$ alkyloxy group, a $C_6$ to $C_{60}$ aryloxy group, a $C_1$ to $C_{40}$ alkylsilyl group, a $C_6$ to $C_{60}$ arylsilyl group, a $C_1$ to $C_{40}$ alkyl boron group, a $C_6$ to $C_{60}$ aryl boron group, a $C_6$ to $C_{60}$ arylphosphine group, a $C_6$ to $C_{60}$ arylphosphine oxide group, and a $C_6$ to $C_{60}$ arylamine group.

11. The organic electroluminescent device of claim 10, wherein both $X_1$ and $X_2$ are $N(Ar_1)$.

12. The organic electroluminescent device of claim 10, wherein $Y_1$ to $Y_8$ comprise one N.

13. The organic electroluminescent device of claim 7, wherein $Ar_1$ to $Ar_5$ are each independently selected from the group consisting of a $C_6$ to $C_{60}$ aryl group, a heteroaryl group having 5 to 60 nuclear atoms, and a $C_6$ to $C_{60}$ arylamine group; and the $C_6$ to $C_{60}$ aryl group, the heteroaryl group having 5 to 60 nuclear atoms, and the $C_6$ to $C_{60}$ arylamine group are each unsubstituted or substituted with one or more functional groups selected from the group consisting of a $C_1$ to $C_{40}$ alkyl group, a $C_6$ to $C_{60}$ aryl group, and a heteroaryl group having 5 to 60 nuclear atoms.
14. The organic electroluminescent device of claim 7, wherein $Ar_1$ to $Ar_5$ are selected from the group of the following substituents:
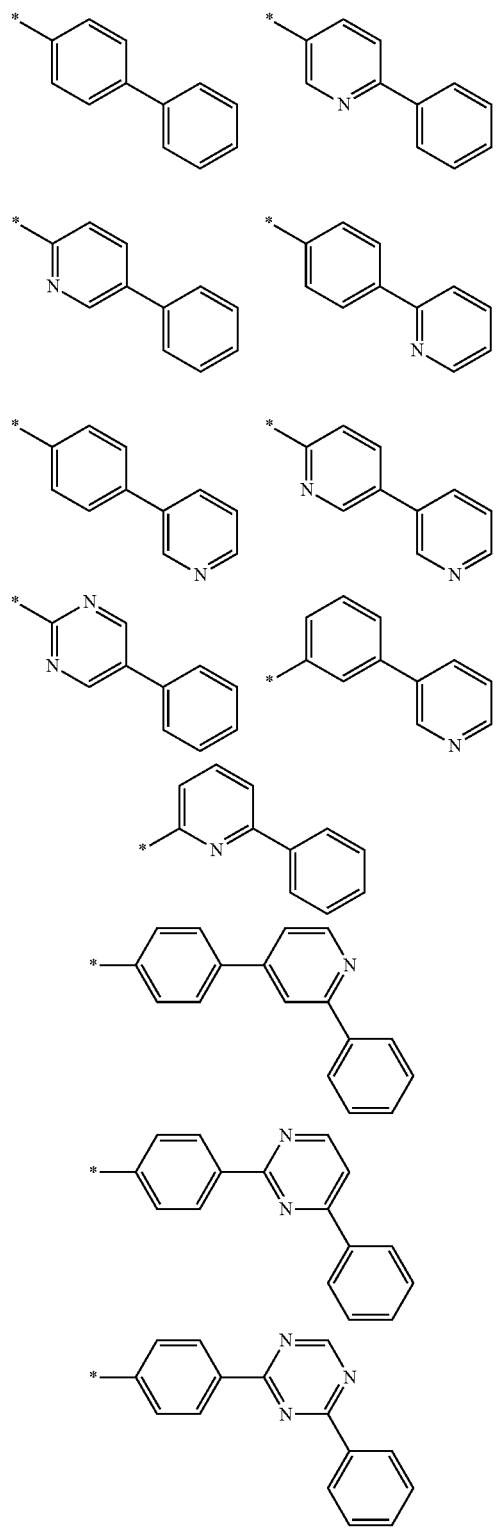
-continued
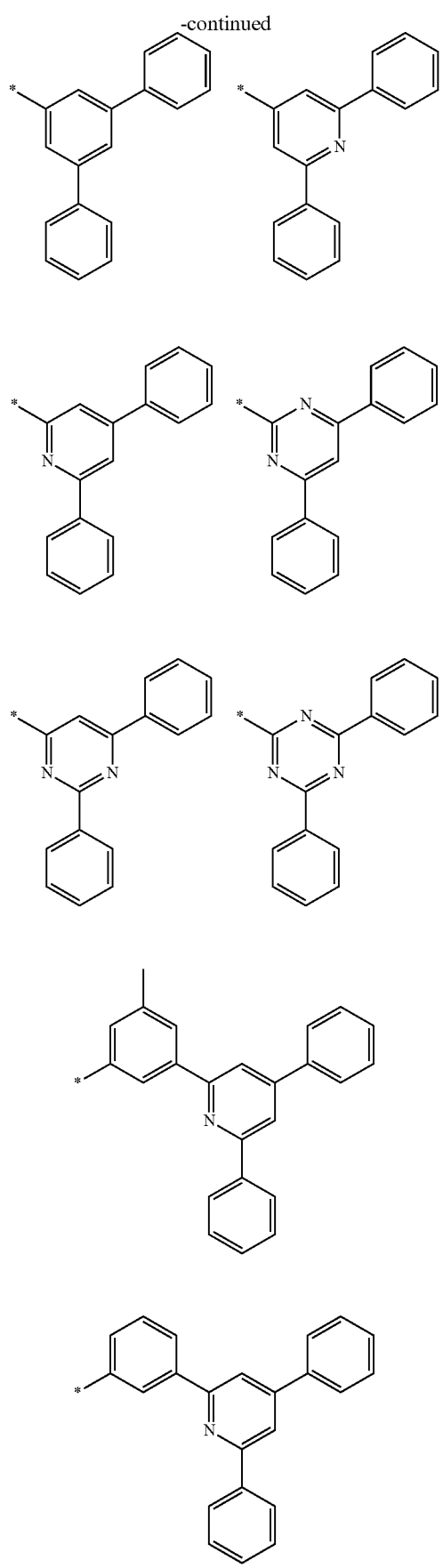

159
-continued
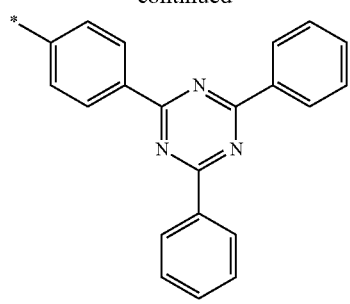
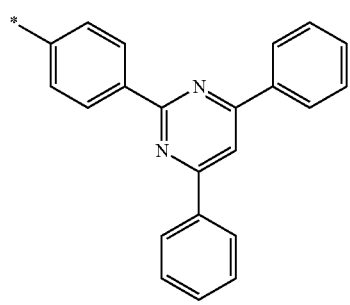
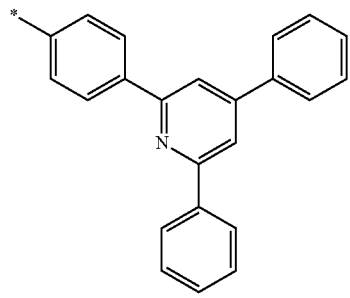
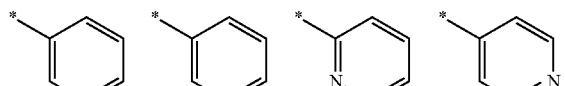
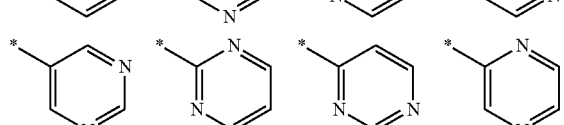
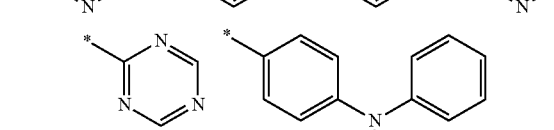
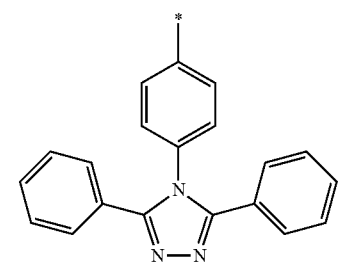
160
-continued
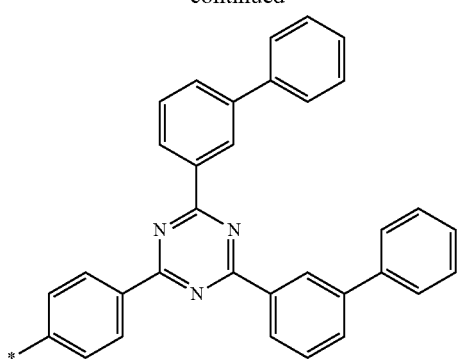
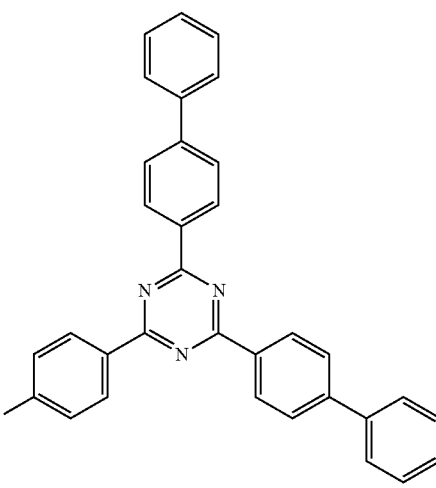
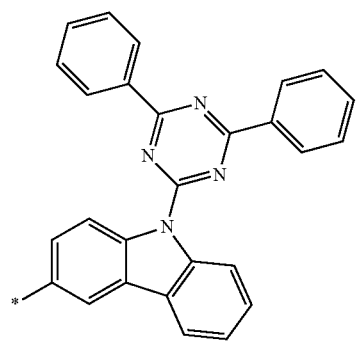
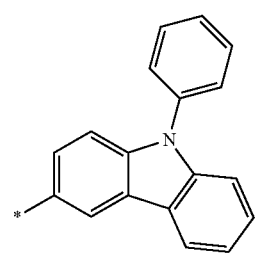

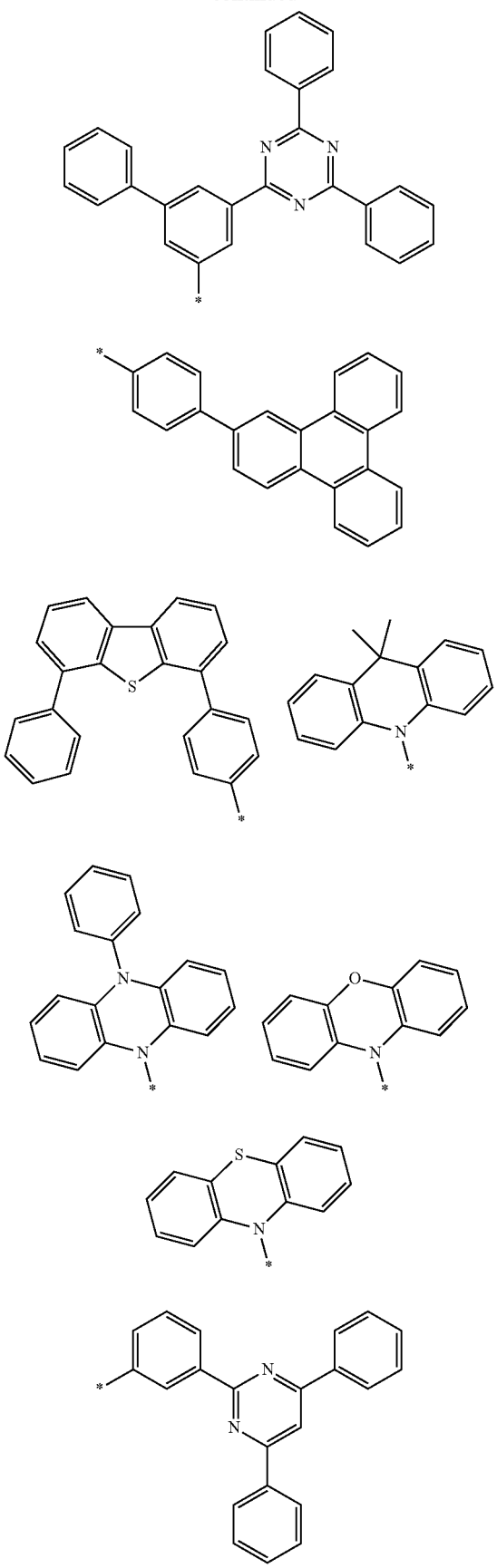
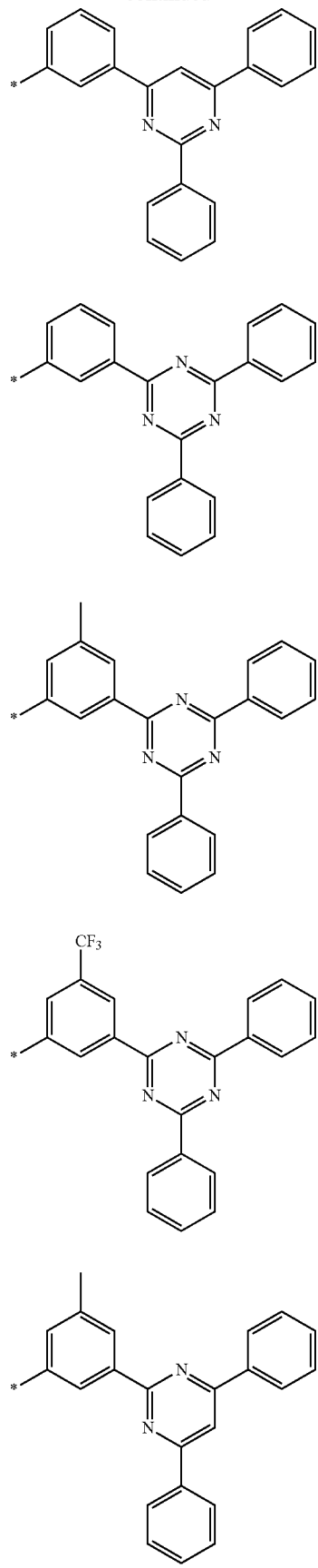

163
-continued
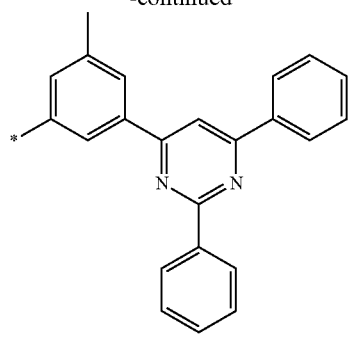
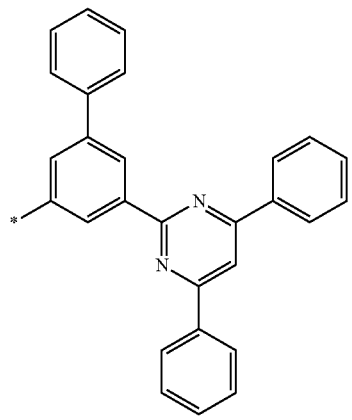
164
-continued
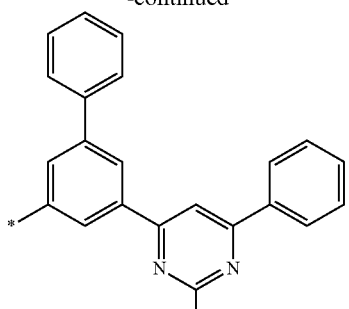
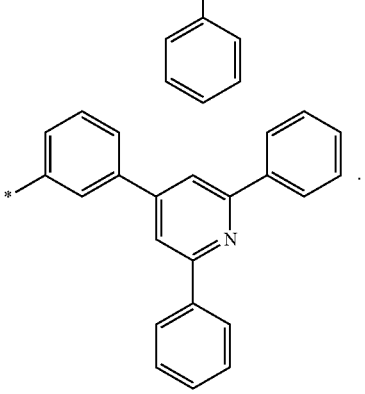
* * * * *